US010286091B2

(12) United States Patent
Desgranges et al.

(10) Patent No.: US 10,286,091 B2
(45) Date of Patent: May 14, 2019

(54) DENDRI-TAC AND THEIR USE AS THERANOSTICS

(71) Applicants: UNIVERSITE D'AVIGNON ET DES PAYS DU VAUCLUSE, Avignon (FR); CENTRE NATIONAL DE LA RECHERCHE SCIENTIFIQUE, Paris (FR)

(72) Inventors: Stéphane Desgranges, Avignon (FR); Wlodzimierz Urbach, Paris (FR); Lucie Somaglino, La Seyne-sur-mer (FR); Nicolas Taulier, Paris (FR); Christiane Pepin, Althen des Paluds (FR)

(73) Assignees: UNIVERSITE D'AVIGNON ET DES PAYS DU VAUCLUSE, Avignon (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 15/571,528

(22) PCT Filed: May 19, 2016

(86) PCT No.: PCT/IB2016/052952
§ 371 (c)(1),
(2) Date: Nov. 3, 2017

(87) PCT Pub. No.: WO2016/185425
PCT Pub. Date: Nov. 24, 2016

(65) Prior Publication Data
US 2018/0126011 A1 May 10, 2018

(30) Foreign Application Priority Data

May 19, 2015 (EP) .................................... 15305750

(51) Int. Cl.
*A61K 9/00* (2006.01)
*A61K 49/18* (2006.01)
(Continued)

(52) U.S. Cl.
CPC ...... *A61K 49/1806* (2013.01); *A61K 41/0028* (2013.01); *A61K 41/0033* (2013.01);
(Continued)

(58) Field of Classification Search
CPC .................................................. A61K 49/1806
See application file for complete search history.

(56) References Cited

FOREIGN PATENT DOCUMENTS

WO 2007112100 10/2007

OTHER PUBLICATIONS

P. Barthelemy et al., "A New Class of Sulfoxide Surfactants derived from Tris. Synthesis and Preliminary Assessments of their Properties", Bioorganic & Medicinal Chemistry Letters, Pergamon, vol. 8, No. 12, Jun. 16, 1998, p. 1559-1562.
(Continued)

*Primary Examiner* — Paul W Dickinson
(74) *Attorney, Agent, or Firm* — Lex IP Meister, PLLC

(57) ABSTRACT

The present invention relates to novel amphiphilic dendrimers, hereafter denoted Dendri-TAC. The present invention also relates to perfluorocarbon nanoemulsions stabilized by these amphiphilic dendrimers and their uses for in vivo diagnostic and/or for therapy, notably as theranostic tools, for detection and/or treatment of cancer.

25 Claims, 8 Drawing Sheets

Figure 1:
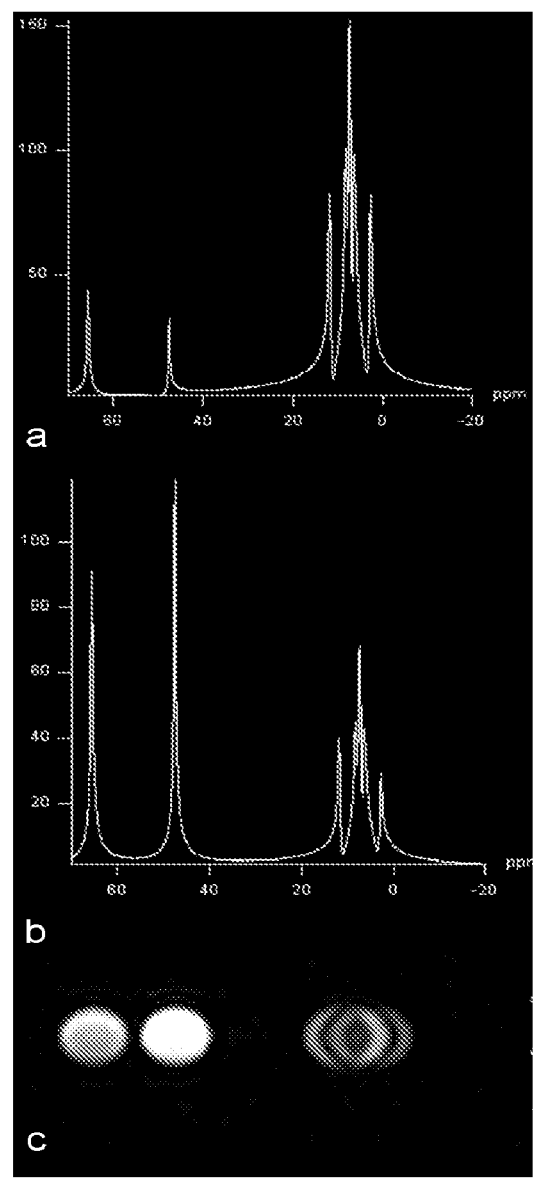

(51) Int. Cl.
*C08G 83/00* (2006.01)
*A61K 49/00* (2006.01)
*A61K 41/00* (2006.01)
*A61K 49/22* (2006.01)
*B01J 31/06* (2006.01)
*A61K 47/54* (2017.01)
*A61K 47/62* (2017.01)
*A61K 47/69* (2017.01)

(52) U.S. Cl.
CPC .......... *A61K 47/549* (2017.08); *A61K 47/62* (2017.08); *A61K 47/6907* (2017.08); *A61K 49/0028* (2013.01); *A61K 49/0036* (2013.01); *A61K 49/0078* (2013.01); *A61K 49/226* (2013.01); *B01J 31/064* (2013.01); *C08G 83/003* (2013.01); *C08G 83/004* (2013.01); *C08G 83/008* (2013.01)

(56) References Cited

OTHER PUBLICATIONS

A. Polidori et al., "Synthesis and aggregation behaviour of symmetric glycosylated bolaamphiphiles in water", Issue in Honor of Prof. Armand Lattes, ARKIVOC, Mar. 9, 2006, p. 73-89.

P. Barthelemy et al., "Synthesis and Preliminary Assessments of Ethyl-Terminated Perfluoroalkyl Nonionic Surfactants Derived from Tris(hydroxymethyl)acrylamidomethane", Organic Letters, vol. 1, No. 11, Dec. 1, 1999, p. 1689-1692.

K. Astafyeva et al., "Perfluorocarbon nanodroplets stabilized by fluorinated surfactants: characterization and potentiality as theranostic agents", Journal of Materials Chemistry B, The Royal Society of Chemistry, vol. 3, No. 14, Jan. 14, 2015, p. 2892-2907.

DENDRI-TAC AND THEIR USE AS THERANOSTICS

The present invention relates to novel amphiphilic dendrimers, hereafter denoted Dendri-TAC. The present invention also relates to perfluorocarbon nanoemulsions stabilized by these amphiphilic dendrimers and their uses for in vivo diagnostic and/or for therapy, notably as theranostic tools, for detection and/or treatment of cancer.

Even though within the last decades the pharmaceutical industry has been successful in discovering many new cytotoxic drugs that can potentially be used for the treatment of cancer, this life-threatening disease still causes near 7 million deaths every year worldwide and the number is growing. Nowadays chemotherapy still remains a major cancer treatment which effectiveness is hampered by several factors including genomic instability of tumor cells, multidrug resistance, and toxicity on healthy tissues. Thus, there is an urgent need to imagine and develop alternatives to conventional chemotherapy leading to personalized and efficient therapy with lower side effects. Among all the explored options including cancer prevention, it appears that detecting cancer earlier and monitoring changes in response to therapy are key components to improve treatment efficacy and reduce the global burden of the disease.

A particularity of tumor vessels, in contrast to normal ones, is to be permeable to large particles, with a mean pore cutoff size ranging from 400 to 800 nm, depending of the type of tumor. Moreover, the combination of high tumor interstitial pressure with a deficient lymphatic network referred as "enhanced permeability and retention effect" (EPR) results in an increased intratumoral nanoparticles accumulation after intravenous injection. This characteristic can be used to design nanoparticles (NP) that act as contrast agents (for tumor detection) or as selective drug carriers (for tumor treatment). Aside from passive targeting due to EPR effect, selectivity can also be achieved by introducing on the nanoparticle shell, hydrophilic ligands like RGD peptides or glycosidic (or saccharidic) moieties in order to specifically address the nanocarrier to molecular and cellular components of the tumor microenvironment (angiogenesis and/or inflammation).

Once accumulated in the tumor, the carrier also needs to release its drug. This release can be triggered by applying locally ultrasound waves. An attractive venue is to combine therapy with imaging in order to adjust the treatment and to monitor the drug delivery. For this purpose, the carrier needs to possess the characteristics of a contrast agent, this also offers the possibility to be used as a tool for early tumor detection. Contrast echography, near-infrared (NIR) fluorescence imaging and MRI are the best imaging modalities suited for tumor detection associated with contrast agents. Contrast echography has real-time imaging ability, offers the cheaper imaging alternative and is available in most hospitals. Whereas MRI offers the best spatial resolution but has no real-time imaging ability and is an expensive image modality. Finally, near-infrared fluorescence imaging lies in between the two previous techniques as it offers real-time imaging and a good spatial resolution but is very limited in depth penetration. Commercial Ultrasound Contrast Agents (UCA) are made of encapsulated bubbles, filled with either air or perfluorinated gas, that permits to enhance blood contrast after their intravenous injection. However, their micrometric size (1-10 µm) confines them to the vascular compartment and prevents them to take advantage of the EPR effect. In addition, they exhibit a rapid blood clearance, representing a barrier for their use as quantitative tracers or drug carriers. To the contrary, commercial MRI contrasts are small molecules, commonly based on gadolinium, that leak across even normal vessels wall. For several specific categories of patients, a known side effect of gadolinium-based agents is to increase the risk for developing a serious systemic fibrosing disease. Near-infrared fluorescence agents are also small molecules with a large variety of structures. Even if they get dispersed in the all body, their strength is to be able to target specific receptors thanks to their chemical design.

Considering the state of the art, there is a need for contrasts agents that overcome the limitations of existing ones.

Recently, perfluorocarbon (PFC) nanodroplets stabilized by fluorinated surfactants have been disclosed and their theranostic capabilities as drug carriers and $^{19}F$ MRI contrast agents studied (K. Astafyeva et al., J. Mater. Chem. B, 2015, 3, 2892-2907). More specifically, these nanocarriers consist of perfluorocarbon droplets, which are dispersed in an aqueous solvent. The stability and size of the perfluorocarbon droplets are driven by the chemical structure of the shell encapsulating the droplet, which is composed of biocompatible fluorinated surfactants called F-TACs. The chemical structure of fluorinated surfactants $F_iTAC_n$ is composed of a polar head made of n repeating Tris units (n=DPn is the average degree of polymerization) and of a hydrophobic perfluorinated tail ($F_i\text{=}C_6F_{13}C_2H_4$ or $F_i\text{=}C_8F_{17}C_2H_4$).

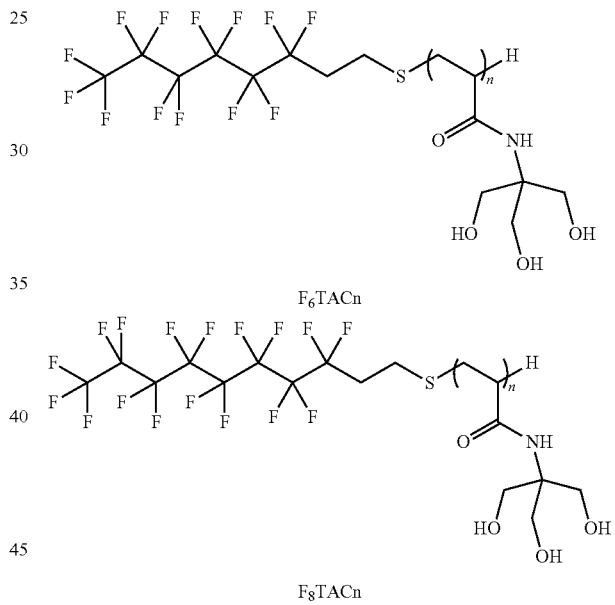

The perfluorocarbon liquid core allows them to act as contrast agents for both contrast echography and MRI. Indeed, in contrast echography, although the acoustic resonance frequency of these nanocarriers lies outside the clinical range, it has been shown that they can still enhance ultrasound contrast through various mechanisms (aggregation, proximity of a surface, coalescence . . . ). However, the best approach to significantly improve their echogenicity is to vaporize them. It is also known that nanocarriers made of a liquid perfluocarbon core can be detected using $^{19}F$ MRI.

Although the potential of F-TACs to stabilize perfluorocarbon nanoemulsions is interesting, their synthesis involves several difficulties in controlling the final macromolecules architecture from batch to batch (DPn, polydispersity). Further, the estimate of their molecular weight, and thereby their structure, is even more difficult to assess that the intended DPn is high. Furthermore, for F-TACs with bicatenar or long monocatenar fluorinated tails, high DPn, that is a polar head made of numerous n repeating Tris units, are needed to ensure the final water solubility.

Thus, there is a need for contrasts agents that overcome the limitations of existing ones and notably of F-TACs.

It now has been developed a new class of fluorinated amphiphiles, with their hydrocarbon analogues, having the main advantages of F-TACs (biocompatibility, modular structure) with a well-defined, tunable and more controlled resulting structure.

More specifically, it now has been designed novel nanocarriers consisting of perfluorcarbon droplets dispersed in an aqueous solvent, and encapsulated by a shell which is composed of novel dendronic fluorinated or hydrocarbon surfactants advantageously exhibiting a high affinity for both the PFC core and surrounding water. These dendronic surfactants constitute a new class of biocompatible branched fluorinated and hydrocarbon amphiphiles which self-assembling properties are highly tunable through both the nature of their hydrophobic tail (variable length of mono or bicatenar fluorinated or hydrocarbon chains) and the multiplication of branching hydrophilic tree-like arms. Each additional hydrophilic layer or "generation" stepwise allows reaching the optimal nanoparticles diameter for the intended biological applications. Compared to F-TACs, which are linear oligomers, the number of hydrophilic surface groups on dendriTAC increases exponentially with increasing dendrimer generation. Thus, dendriTAC can be advantageously synthesized step by step, thereby allowing to reach a well-defined and highly scalable structure for optimal self-assembly properties. Moreover, according to their architectural components, dendriTAC should offer more opportunities for drug or sonosensitizer encapsulation compared to F-TACs. Indeed, one can assume that the drug-loading capacity of dendriTACs will be improved due to the numerous cavities existing between each branching layers. These interior cavities constitute an additional compartment for drug formulation which is not available on linear oligomers.

These nanoemulsions/nanocarriers/nanoparticles advantageously enable an early detection of tumor development and a controlled and targeted therapy for limited side effects.

Indeed, these nanosystems combine the features of contrast agents for echography, near-infrared fluorescence (if a NIR dye is added), photoacoustic imaging (if an adequate chromophore is included or added in the nanoemulsion) and $^{19}$F MRI, and of drug carriers that are triggered by ultrasounds. Among the numerous hydrophobic bioactive compounds that can be selectively delivered by these nanocarriers (i.e. chemotherapeutics, biocides or any bioactive compound of interest), the nanosystems according to the invention can advantageously carry a molecule called "sonosensitizer" as antitumoral drug. The latter encapsulated chemical compound is originally an innocuous molecule that will acquire a "drug profile" only when stimulated by adequate ultrasound waves. In this respect, a model sonosensitizer such as Protoporphyrin IX (PpIX) may be used to induce tumor regression. In contrast to conventional anti-cancer drugs, the sonosensitizer is nontoxic in the absence of ultrasonic irradiation. Ultrasounds are then used not only to induce the drug release from nanoparticles but also to induce its activation into the targeted/detected tumor tissues. This therapeutic pathway is referred to as sonodynamic therapy (SDT).

It is noteworthy that PpIX, like many other sonosensitizers, can be either used as a "photo- or a sonosensitizer agent" and the involved therapeutic pathway is called "photodynamic" or "sonodynamic" therapy (PDT or SDT). The use of PpIX in PDT presents some limitations including limited light penetration into tumor tissue and potential phototoxicity in normal ones. In such conditions, ultrasounds appear to be the appropriate waves to elicit detection, controlled delivery and PpIX activation. However, a combination of sono- and photoactivation of the sensitizer could be attempted to elicit an additive or synergistic therapeutic effect.

Today, the exact mechanism of sonodynamic effect on cells still remains controversial. This is probably due to the versatility of the sonodynamically-induced antitumor effect which seems to be closely linked to the experimental conditions (intensity and frequency of the applied ultrasound wave, pulse duration, nature of the sonosensitizer, viscosity of the culture medium for in vitro assays . . . ) together with intrinsic pathophysiological properties characterizing each tumor progress (endogenous NO level, cellular antioxidant defense system outflank . . . ). Although it is frequently suggested in the literature that singlet molecular oxygen produced during the sensitizer ultrasound-activation plays a major role in the reported cytotoxicity, many studies clearly demonstrate that its implication in cell damages is not exclusive. Indeed, apart from the mechanical stress ascribable to the acoustic cavitation itself, a whole set of reactive oxygen species with variable lifetime viability is generated during both inertial cavitation and sonoactivation of the sensitizer which synergistic or additive effects induce lethal cell damages. In most of these pathways, oxygen appears to have a central role in the therapeutic outcome of SDT.

Furthermore, hypoxia is known to be implicated into the switch of cancerous cells to resistant and metastatic phenotype. Hypoxia is also a potent stimulator of VEGF expression which is one of the major signals in the initiation of tumor angiogenesis.

In such conditions, a further benefit of this invention is that the nanoparticles may be loaded with exogenous oxygen in addition of sonosensitizer to improve efficiency. This encapsulation is possible because of the well-known ability of perfluorocarbons to solubilize high concentrations of oxygen, hence their use as blood substitutes for oxygen delivery. The activation of the sonosensitizer causes the production of singlet oxygen itself leading to—or accompanied by—the formation of "reactive oxygen species" (ROS) in cells. These waterfall excitations induce apoptosis and/or necrosis of cancer cells leading to the destruction of the tumor. Thus, the concomitant delivery of a sonosensitizer and oxygen to tumor tissues represents an elegant way to improve the tumor response to SDT and to limit the angiogenesis supply necessary for continued tumor growth and dissemination beyond the primary site.

Hence, the affinity of the nanoparticles of the invention for tumor tissue, as a consequence of passive (via EPR effect) or active (via specific ligands) targeting, will ensure enhanced contrast. As the nanoparticles can be visualized by echography, $^{19}$F MRI, NIR fluorescence (if a dye is present), or photoacoustic imaging (if an adequate chromophore is included or added in the nanoemulsion) the best technique to detect tumors can be selected at their early stage of growth.

Furthermore, these nanoparticles provide a high level of targeting compared to usual drug delivery systems. Indeed, first, passive or active accumulation of nanoparticles can be achieved on the tumor site, next, the content release can be precisely triggered by focused ultrasound on this site, and finally the sonosensitizer (such as PpIX or any other encapsulated sonosensitizer) can be activated to induce cytotoxicity on cancerous cells. Then, only nanoparticles exposed to the focused ultrasound field will exhibit a controlled cytotoxic effect.

Amphiphilic Dendrimers

Thus, in one aspect, the present invention relates to an amphiphilic dendrimer of generation n comprising:
- an hydrophobic central core of valence m;
- m generation chains attached to the central core and branching around the core; and
- an hydrophilic terminal group at the end of each generation chain;

wherein, in said amphiphilic dendrimer of generation n:
m is an integer superior to 1 and notably 2 or 3;
n is an integer from 0 to 12;

the hydrophobic central core comprises a $C_4$-$C_{10}$ perfluoroalkyl group, the hydrophilic terminal group comprises:
a mono-oligo- or polysaccharide residue,
a cyclodextrin residue,
a polyethylene glycol (PEG) residue,
a peptide residue,
a tris(hydroxymethyl)aminoethane (Tris), or
a 2-amino-2-methylpropane-1,3-diol.

In another aspect, the present invention relates to an amphiphilic dendrimer of generation n comprising:
an hydrophobic central core of valence 2 or 3;
generation chains attached to the central core and branching around the core; and
an hydrophilic terminal group at the end of each generation chain;
wherein
n is an integer from 0 to 12;
the hydrophilic terminal group comprises:
a mono-, oligo- or polysaccharide residue,
a cyclodextrin residue,
a polyethylene glycol (PEG) residue,
a peptide residue,
a tris(hydroxymethyl)aminoethane (Tris), or
a 2-amino-2-methylpropane-1,3-diol;
the central core is a group of formula (Ia) or (Ib):

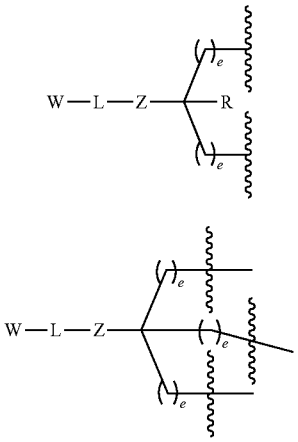

(Ia)

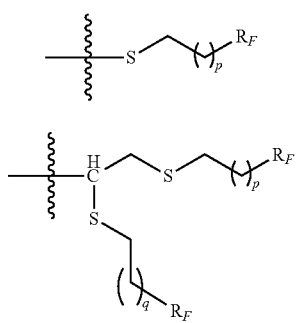

(Ib)

wherein:
W is $R_F$ or a group selected from $W_0$, $W_1$, $W_2$ or $W_3$:

$w_0$

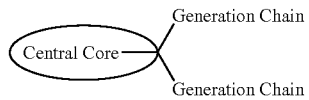

$w_1$

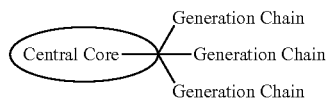

$w_2$

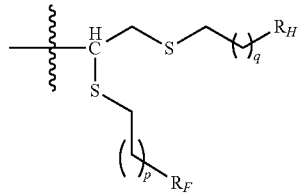

$w_3$

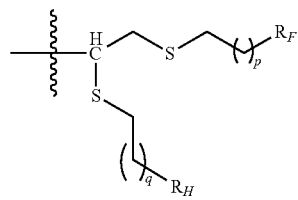

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more O—, —S—,
Z is C(=O)NH or NHC(=O),
R is a $C_1$-$C_6$ alkyl group, and
e is at each occurrence independently selected from 0, 1, 2, 3 or 4.

In one embodiment, $R_F$ is a $C_4$-$C_{10}$ perfluoroalkyl and $R_H$ is a $C_1$-$C_{24}$ alkyl group. In this case, the hydrophobic central core of the amphiphilic dendrimer does comprise a perfluoroalkyl group, and said dendrimer is herein referred to as fluorinated amphiphilic dendrimer.

In another embodiment, $R_F$ is a $C_1$-$C_{24}$ alkyl group and $R_H$ is a $C_1$-$C_{24}$ alkyl group. In this case, the hydrophobic central core of the amphiphilic dendrimer does not comprise a perfluoroalkyl group, and said dendrimer is herein referred to as hydrocarbon amphiphilic dendrimer.

As used herein, the "valence m of the central core" refers to the number of generation chains attached to the central core, as illustrated in the following scheme 1:

Scheme 1

Central Core — Generation Chain
              — Generation Chain
m = 2

Central Core — Generation Chain
              — Generation Chain
              — Generation Chain
m = 3

As used herein, a dendrimer of generation n=0, means that the m generation chains are connected to the central core through a first branching point ($G_0$), corresponding to the valence of the central core. A dendrimer of generation n=1 means that each of the m generation chains ramifies itself once, more specifically at the branching point $G_1$ (see scheme 2).

Scheme 2

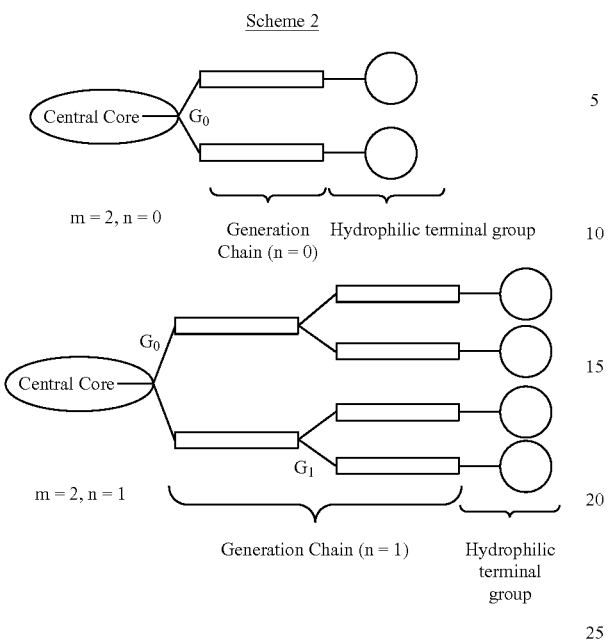

Each generation chain of the amphiphilic dendrimers according to the invention is ended by an hydrophilic terminal group.

In this respect, the mono-, oligo- or polysaccharide residue may be notably glucose, galactose, mannose, arabinose, ribose, maltose, lactose, hyaluronic acid.

The cyclodextrin residue may be selected from α, β or γ-Cyclodextrin.

The peptide residue may be chosen from linear or cyclic peptides containing the arginine-glycine-aspartic acid (RGD) sequence.

In one embodiment, there are included amphiphilic dendrimers wherein m is 2 or 3.

In another embodiment, there are included dendrimers wherein the generation chains are attached to the central core:

either via the group (a):

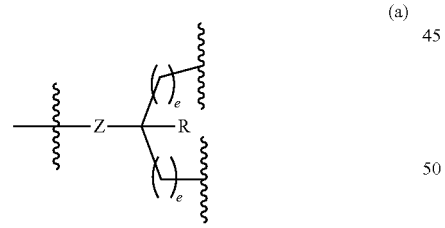

or via the group (b):

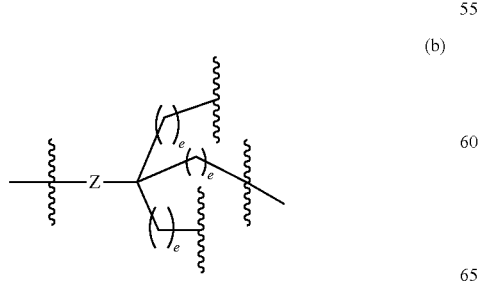

wherein
Z is C(=O)NH or NHC(=O), and is attached to the central core,
R is a $C_1$-$C_6$ alkyl group, and
e is at each occurrence independently selected from 0, 1, 2, 3 or 4;

In a further embodiment, there are included dendrimers wherein the central core is a group of formula (Ia) or (Ib):

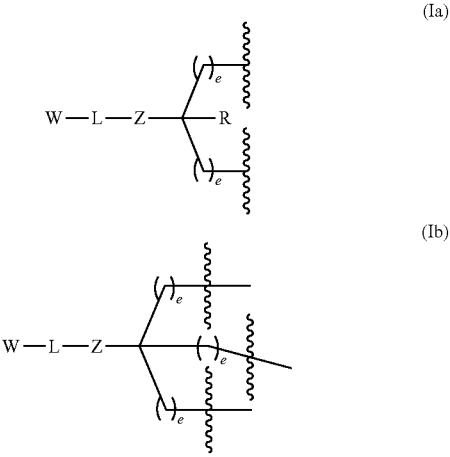

wherein:
W is $R_F$ or a group selected from $W_0$, $W_1$, $W_2$ or $W_3$:

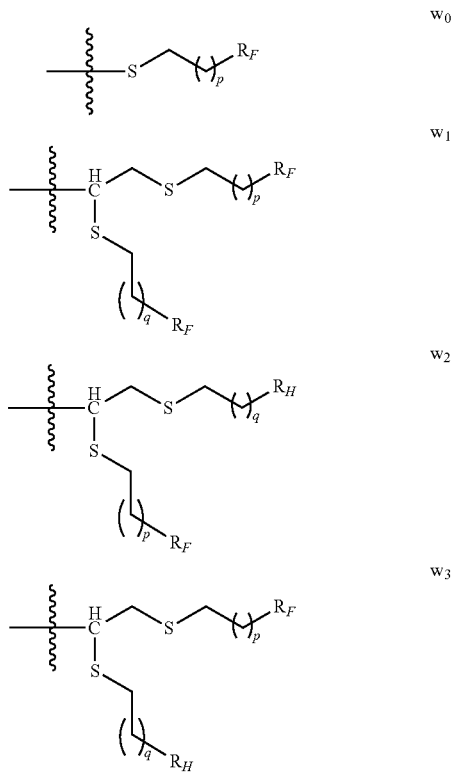

$R_F$ is a $C_4$-$C_{10}$ perfluoroalkyl,
$R_H$ is a $C_1$-$C_{24}$ alkyl group,
p is 0, 1, 2, 3 or 4;
q is 0, 1, 2, 3 or 4;

L is a linear or branched $C_1$-$C_{12}$ alkylene group, optionally interrupted by one or more —O—, —S—.

In still a further embodiment, there are included dendrimers wherein WL is a group selected from:

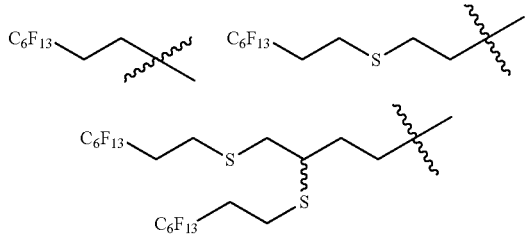

In still a further embodiment, there are included dendrimers wherein WL is a group selected from:

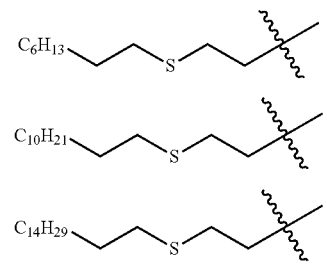

In yet another embodiment, there are included dendrimers wherein each generation chain (n) branches n times via a group (a) or a group (b) as defined above.

In another embodiment, there are included dendrimers wherein the terminal group comprises the following hydrophilic moieties:

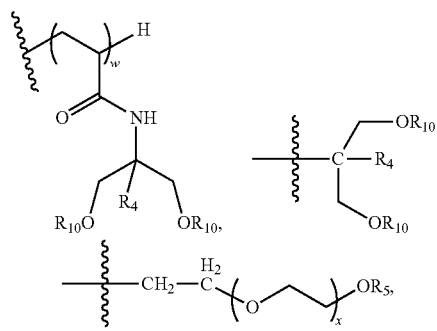

In a particular embodiment, there are included dendrimers having the following formula:

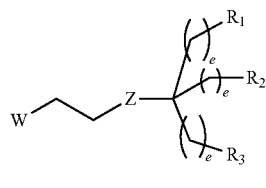

wherein:
W is $R_F$ or a group selected from:

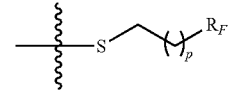
$w_0$

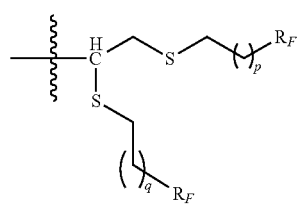
$w_1$

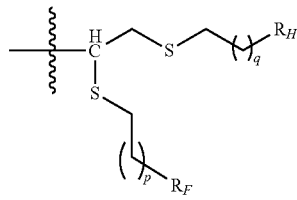
$w_2$

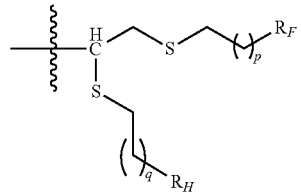
$w_3$ $R_F$ being a $C_4$-$C_{10}$ perfluoroalkyl and $R_H$ being a $C_1$-$C_{24}$ alkyl group,
p is 0, 1, 2, 3 or 4;
q is 0, 1, 2, 3 or 4;
Z is (CO)NH or NH(CO);
$R_1$, $R_2$, $R_3$ are H, or a group selected from (c) or (d):

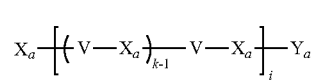
(c)

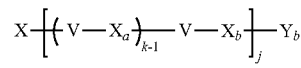
(d)

provided that:
$R_1$, $R_2$, $R_3$ are the same and selected from either group (c) or (d)
or:
one of $R_1$, $R_2$, $R_3$ is H, the two others being the same and selected from either group (c) or (d);
X is $X_a$ when j is 1 and $X_b$ when j is 0;
$X_a$ is at each occurrence independently selected from —OC(=O) $CH_2$—NH—, —OC(=O)$CH_2$—O—$CH_2$—, —O($CH_2$)$_r$C(=O)—NH—, —O($CH_2$)$_r$C(=O)—O—$CH_2$, OC(=O)NH—, —C(=O)—, —NH—, and —O$CH_2$—;
$Y_a$ is independently selected from:

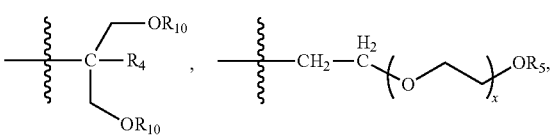

$X_b$ is

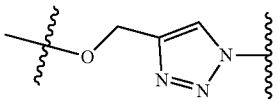 [SMILES: *OCc1cn(*)nn1]

$Y_b$ is independently selected from:

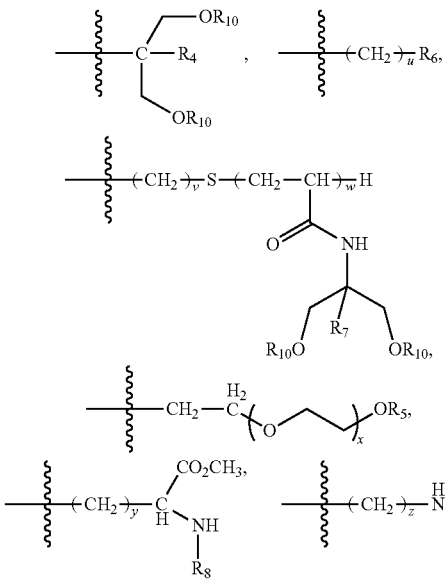

V is:

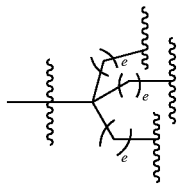

$R_4$, $R_7$ are each independently selected from H, $C_1$-$C_6$ alkyl or $CH_2OR_{10}$;
$R_5$ is selected from H and $C_1$-$C_6$ alkyl;
$R_6$ is a mono-, oligo-, polysaccharide or a cyclodextrin residue;
$R_8$, $R_9$ are each independently a peptide residue;
$R_{10}$ is H or a monosaccharide selected from glucose, galactose or mannose;
i is 0 or 1;
j is 0 or 1;
e is 0, 1, 2, 3 or 4;
k is an integer from 1 to 12, preferably from 1 to 5;
r is an integer from 1 to 10;
u is 0, 1, 2, 3 or 4;
v is 1, 2, or 3;
w is an integer from 1 to 20, preferably from 1 to 10;
x is an integer from 1 to 30;
y, z are each independently an integer from 1 to 6.

In a particular embodiment, there are included dendrimers having the following formula:

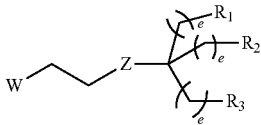

wherein:
W is $R_F$ or a group selected from:

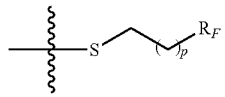   $W_0$

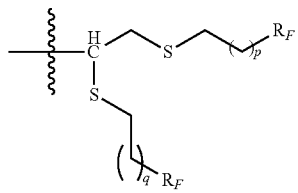   $W_1$

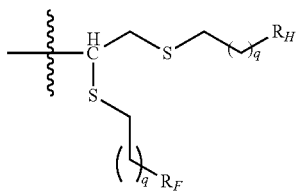   $W_2$

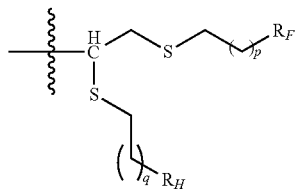   $W_3$ $R_F$ being a $C_1$-$C_{24}$ alkyl group, and $R_H$ being a $C_1$-$C_{24}$ alkyl group,
p is 0, 1, 2, 3 or 4;
q is 0, 1, 2, 3 or 4;
Z is (CO)NH or NH(CO);
$R_1$, $R_2$, $R_3$ are H, or a group selected from (c) or (d):

$$X_a \!\!-\!\!(\!\!-V\!\!-\!\!X_a\!\!-\!\!)_{k-1}\!\!-\!\!V\!\!-\!\!X_a\!\!-\!\!)_i\!\!-\!\!Y_a \quad (c)$$

$$X\!\!-\!\!(\!\!-V\!\!-\!\!X_a\!\!-\!\!)_{k-1}\!\!-\!\!V\!\!-\!\!X_b\!\!-\!\!)_j\!\!-\!\!Y_b \quad (d)$$

provided that:
$R_1$, $R_2$, $R_3$ are the same and selected from either group (c) or (d)
or:
one of $R_1$, $R_2$, $R_3$ is H, the two others being the same and selected from either group (c) or (d);

X is $X_a$ when j is 1 and $X_b$ when j is 0;

$X_a$ is at each occurrence independently selected from —OC(=O)CH$_2$—NH—, —OC(=O)CH$_2$—O—CH$_2$—, —O(CH$_2$)$_r$C(=O)—NH—, —O(CH$_2$)$_r$C(=O)—O—CH$_2$, OC(=O)NH—, —C(=O)—, —NH—, and —OCH$_2$—;

$Y_a$ is independently selected from:

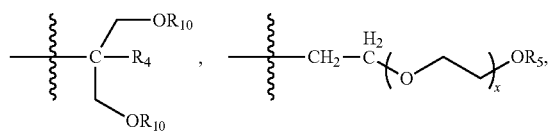

$X_b$ is

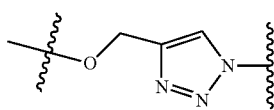

$Y_b$ is independently selected from:

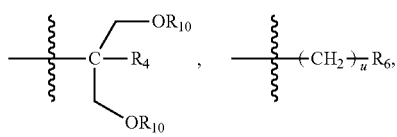

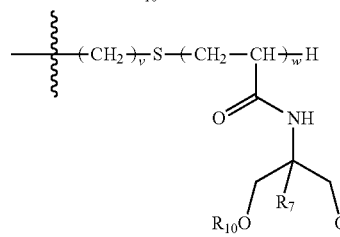

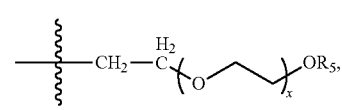

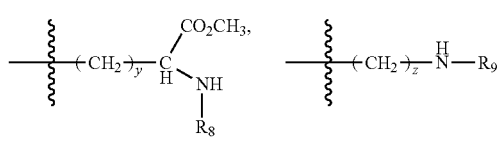

V is:

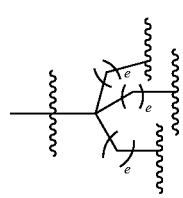

$R_4$, $R_7$ are each independently selected from H, $C_1$-$C_6$ alkyl or CH$_2$OR$_{10}$;

$R_5$ is selected from H and $C_1$-$C_6$ alkyl;

$R_6$ is a mono-, oligo-, polysaccharide or a cyclodextrin residue;

$R_8$, $R_9$ are each independently a peptide residue;

$R_{10}$ is H or a monosaccharide selected from glucose, galactose or mannose;

i is 0 or 1;

j is 0 or 1;

e is 0, 1, 2, 3 or 4;

k is an integer from 1 to 12, preferably from 1 to 5;

r is an integer from 1 to 10;

u is 0, 1, 2, 3 or 4;

v is 1, 2, or 3;

w is an integer from 1 to 20, preferably from 1 to 10;

x is an integer from 1 to 30;

y, z are each independently an integer from 1 to 6.

In another particular embodiment, $R_F$ is a $C_4$-$C_{10}$ alkyl group.

In a particular embodiment, the hydrophilic terminal group of the surfactants defined above is of following formula:

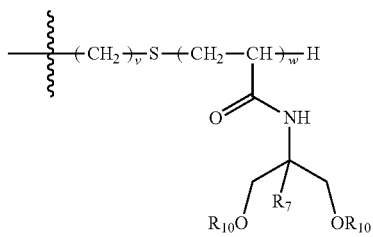

wherein $R_7$, $R_{10}$, v and w are as defined above, v being in particular equal to 3.

In a particular embodiment, the hydrophilic terminal group of the surfactants defined above is of following formula:

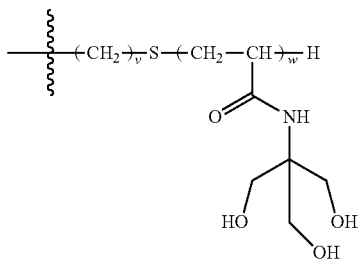

wherein v and w are as defined above, v being in particular equal to 3.

In another particular embodiment, there are included dendrimers which are selected from the following structures:

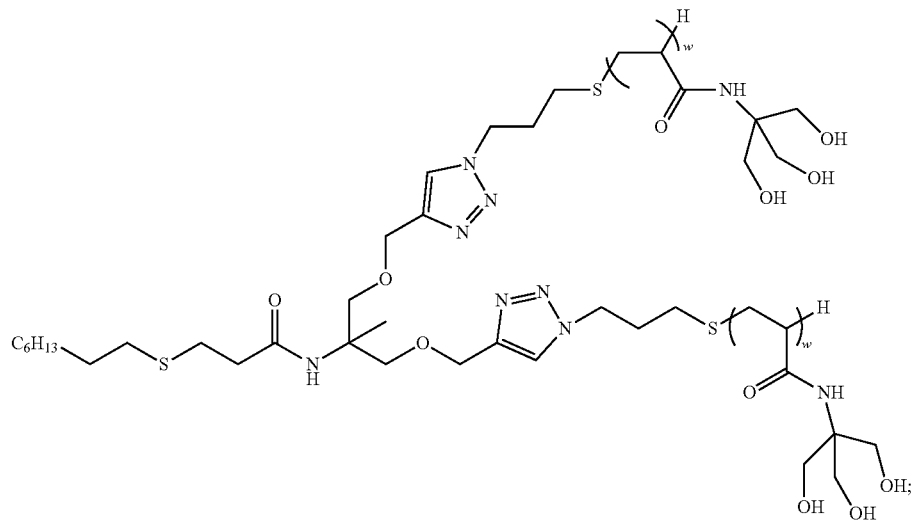
F6 G0diTAC (w*2)
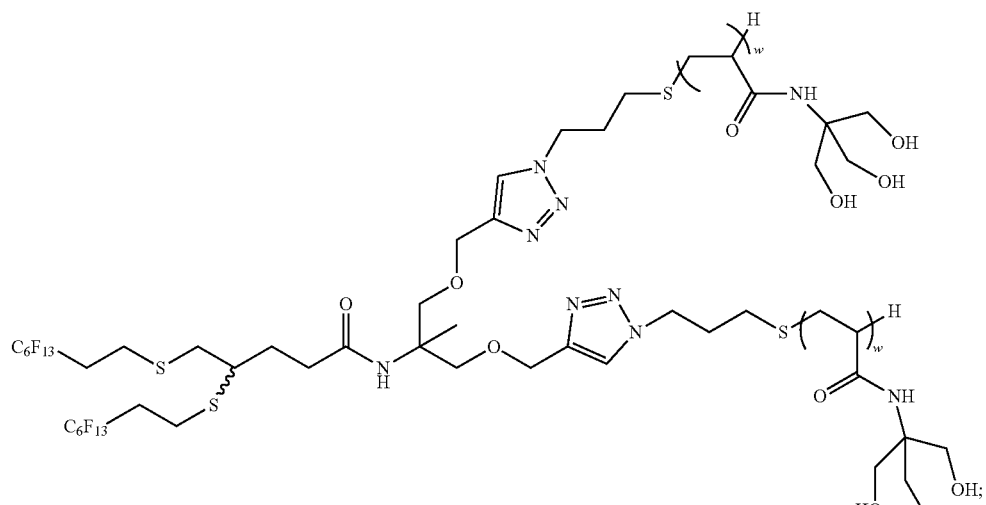
DiF6 G0diTAC (w*2)
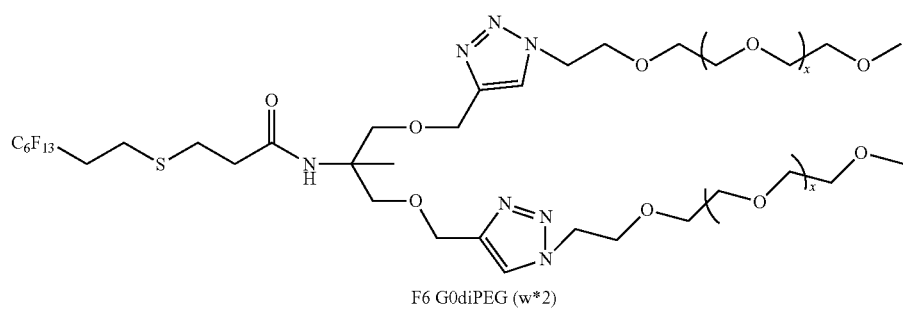
F6 G0diPEG (w*2)

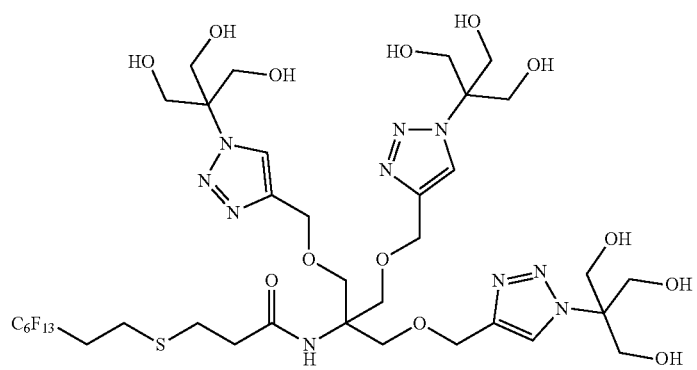
F6 G0triTRIS
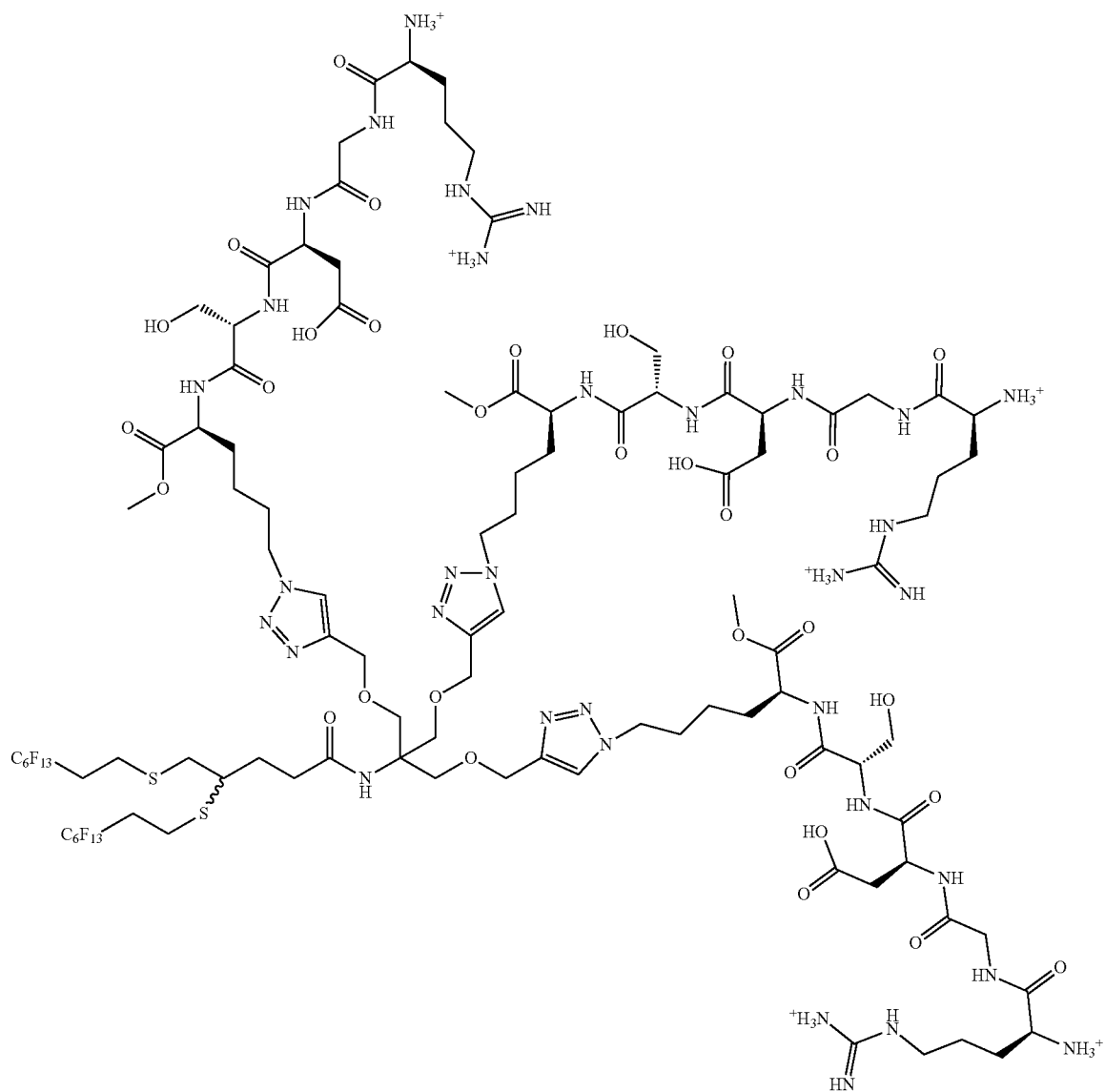
DiF6 G0triSDGR

-continued
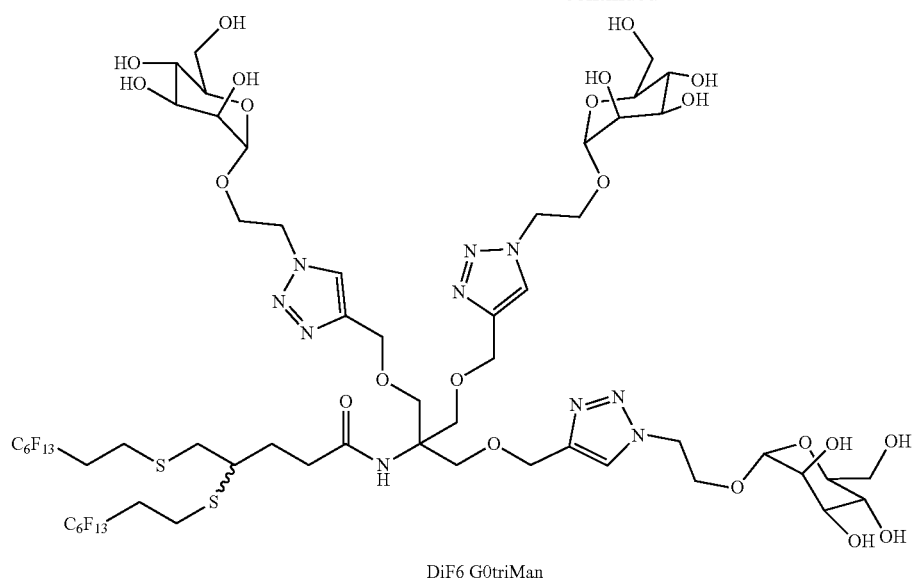
DiF6 G0triMan
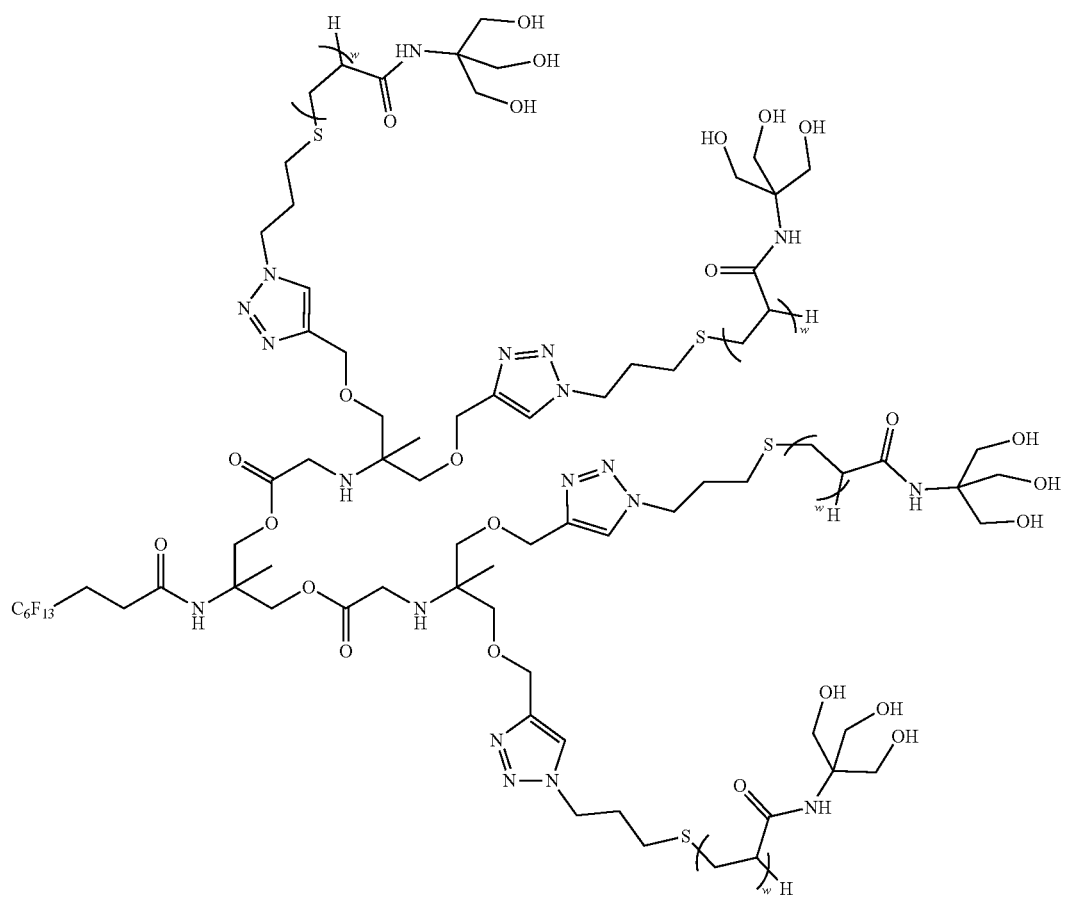
F6G1(ester)tetraTAC

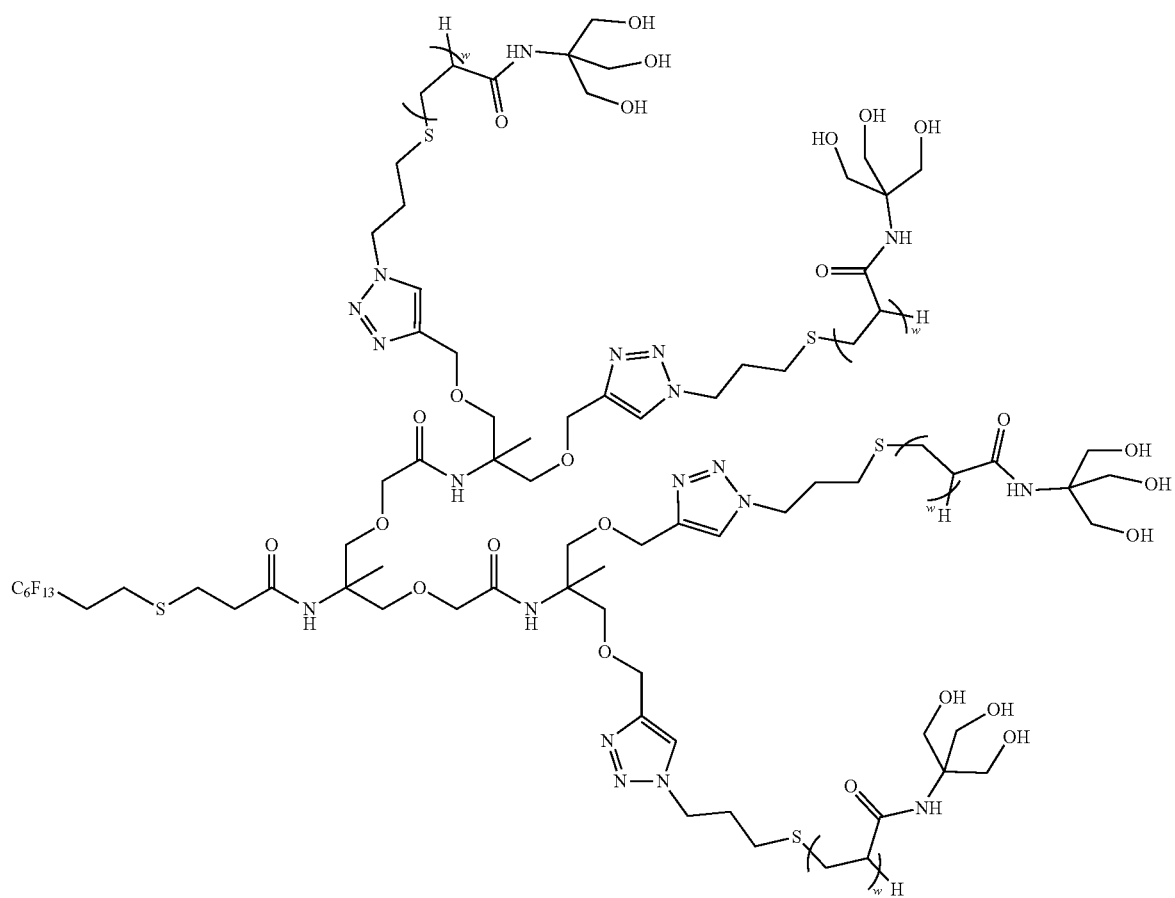
F6G1(amide)tetraTAC

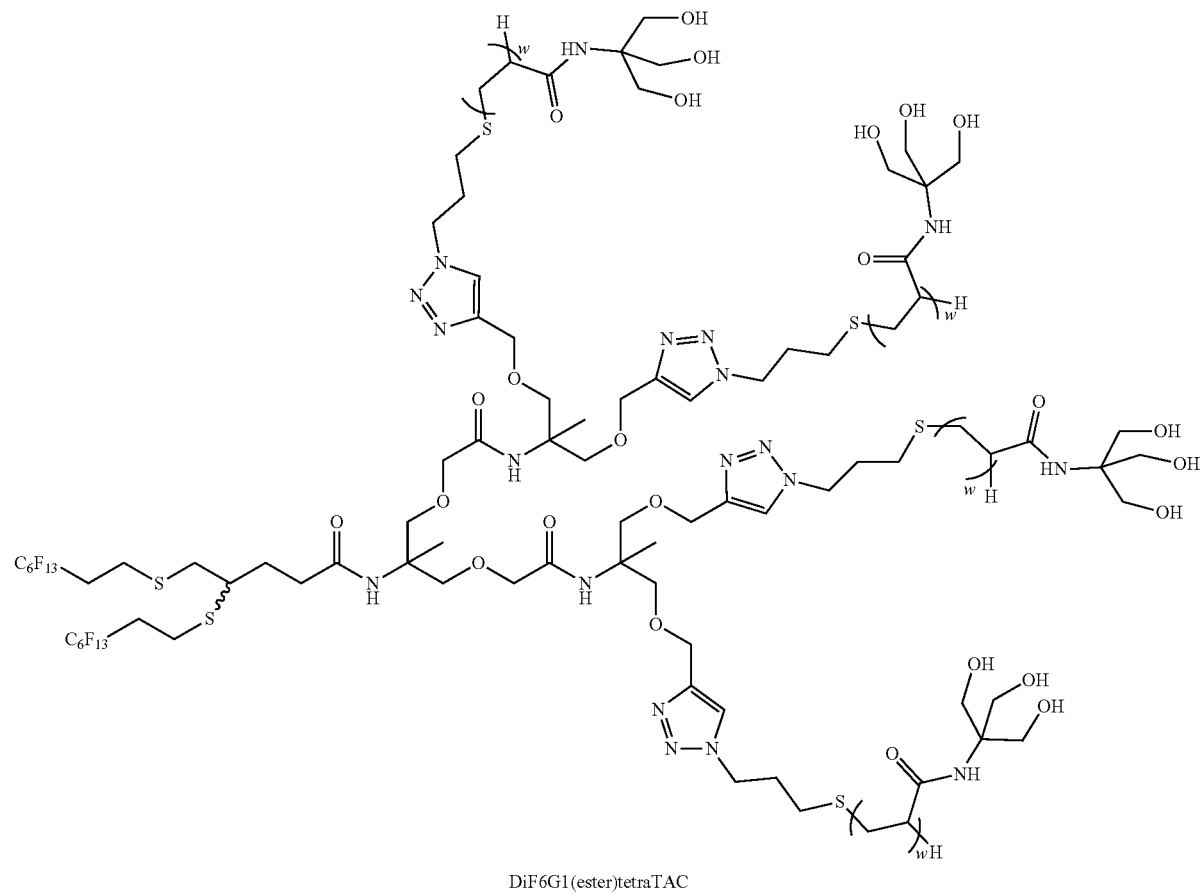
DiF6G1(ester)tetraTAC

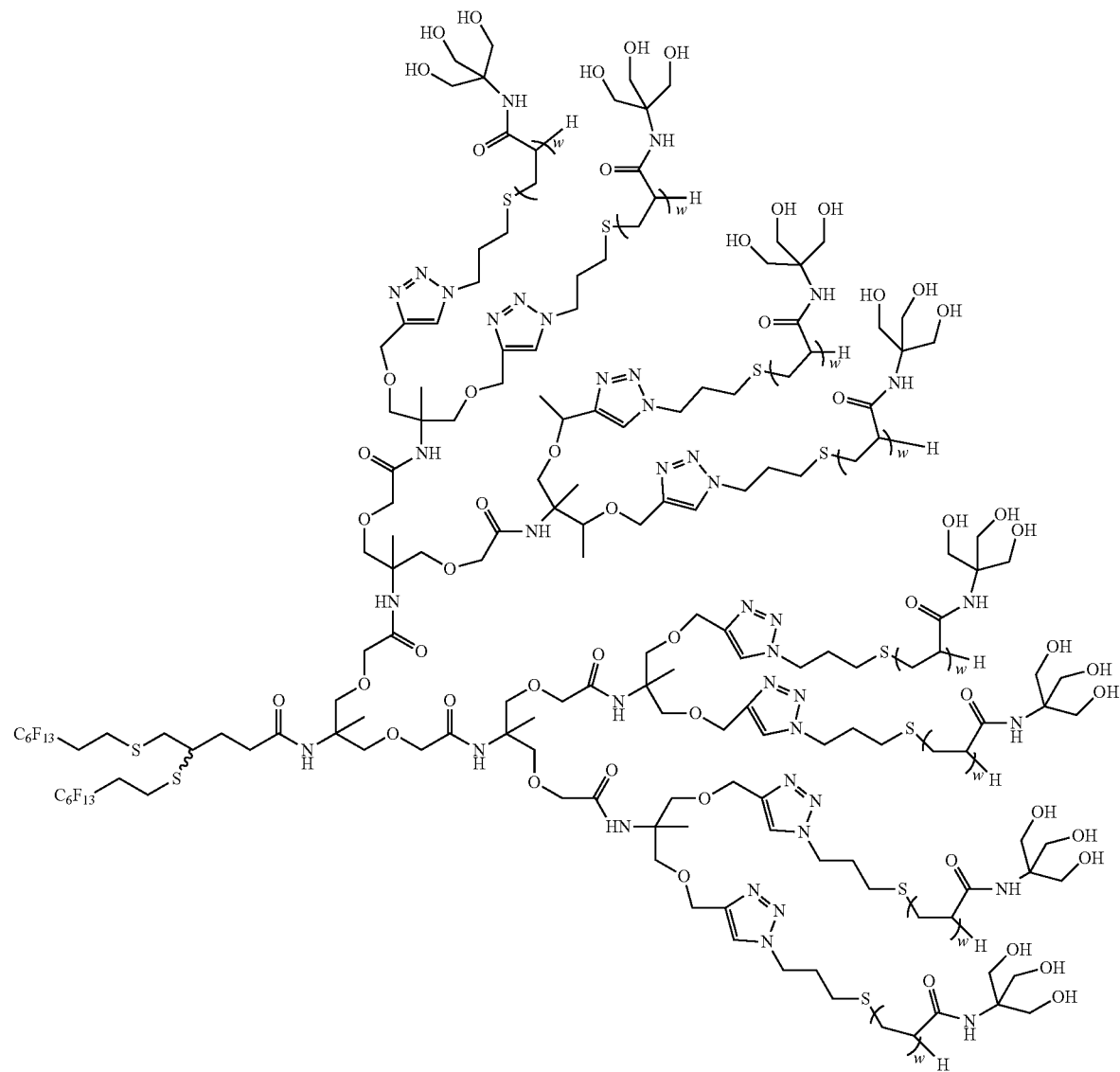
DiF6 G2(amide)octaTAC
wherein x and w are as defined above.
In another particular embodiment, there are included dendrimers which are selected from the following structures:

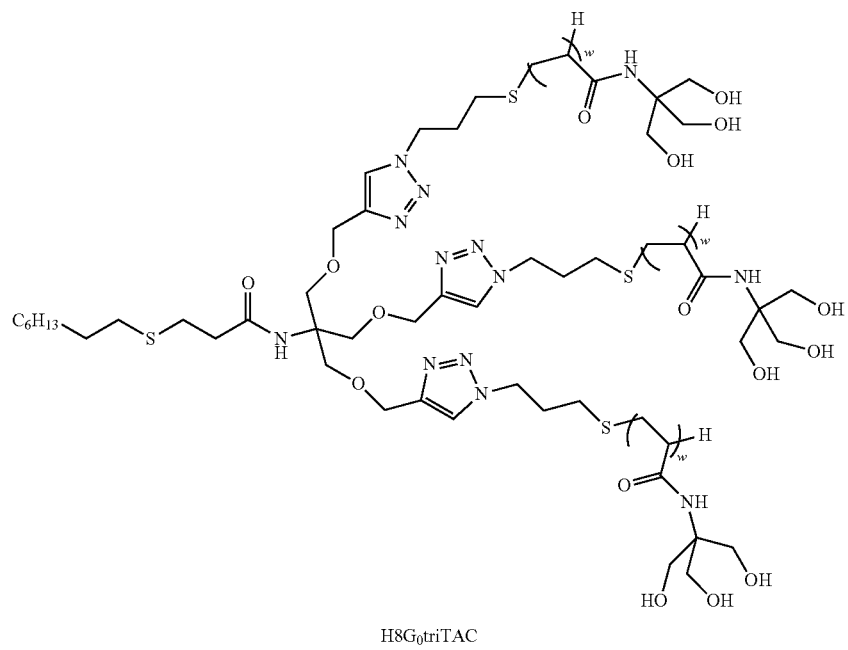
H8G₀triTAC
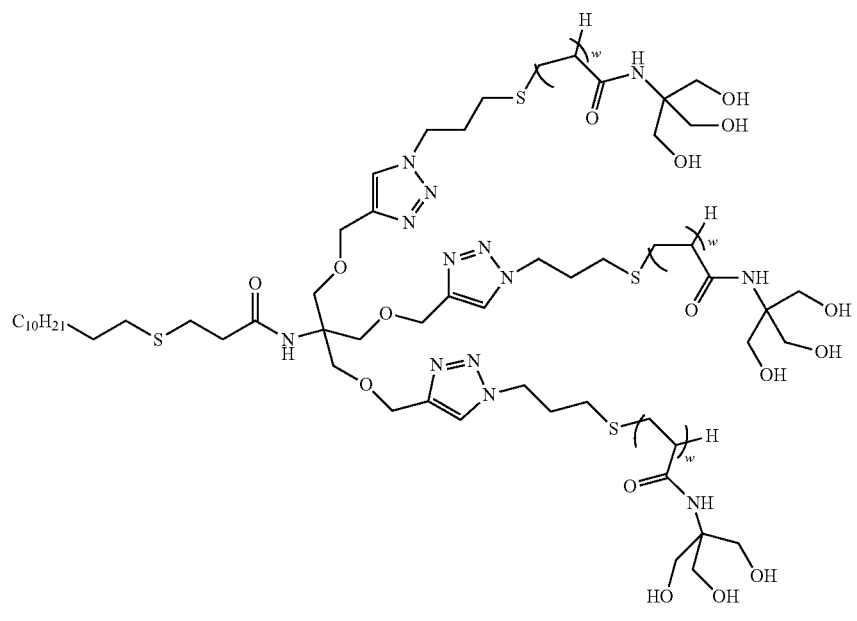
H12G₀triTAC

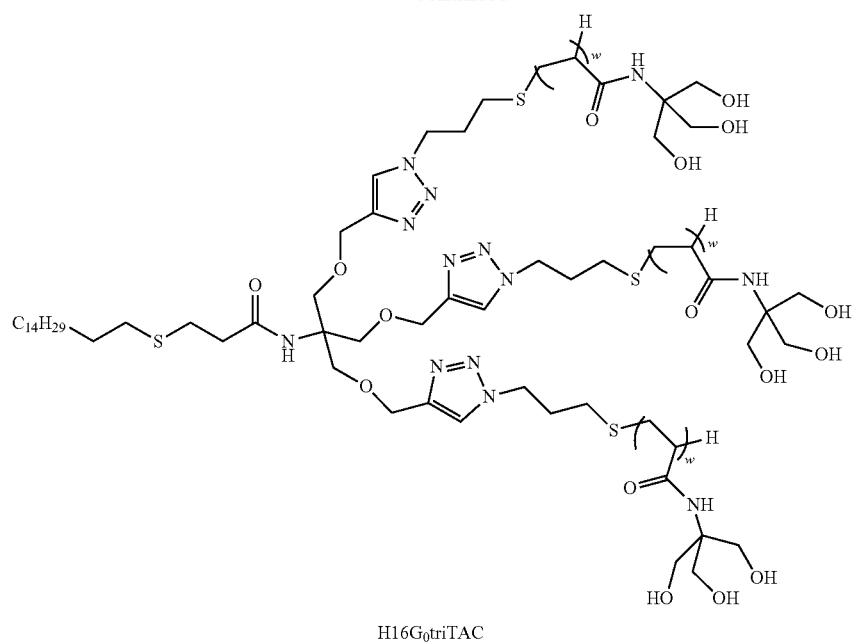
H16G₀triTAC
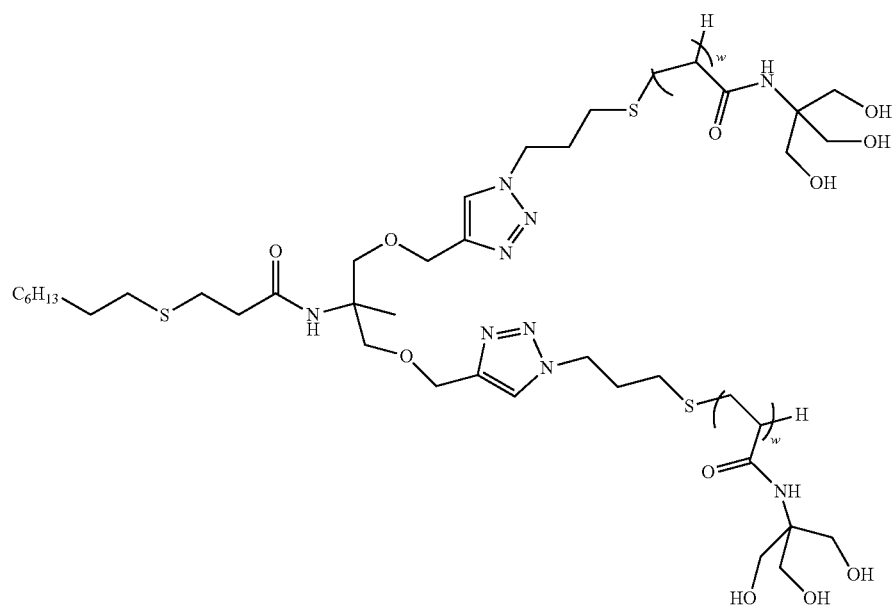
H8G₀diTAC

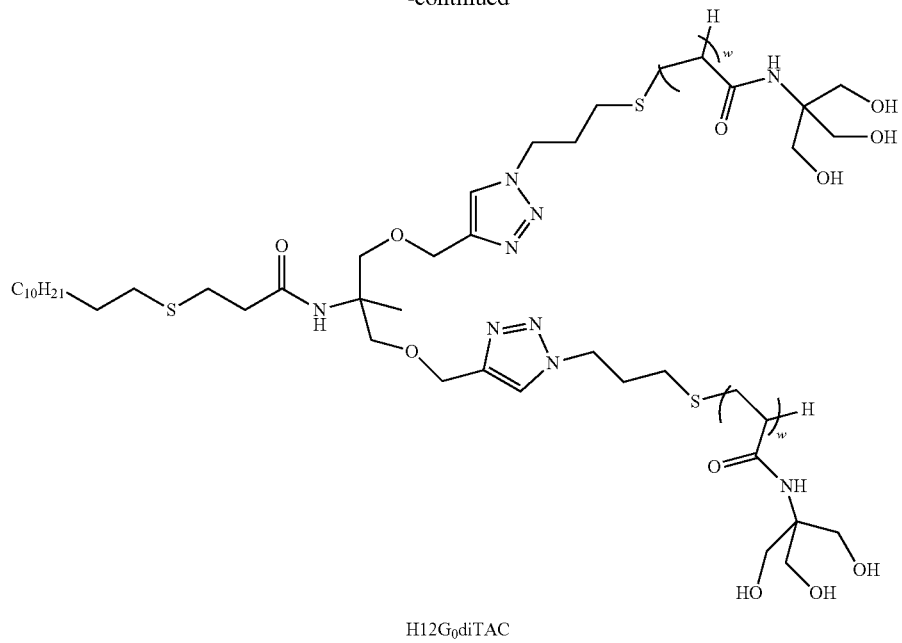

H12G₀diTAC

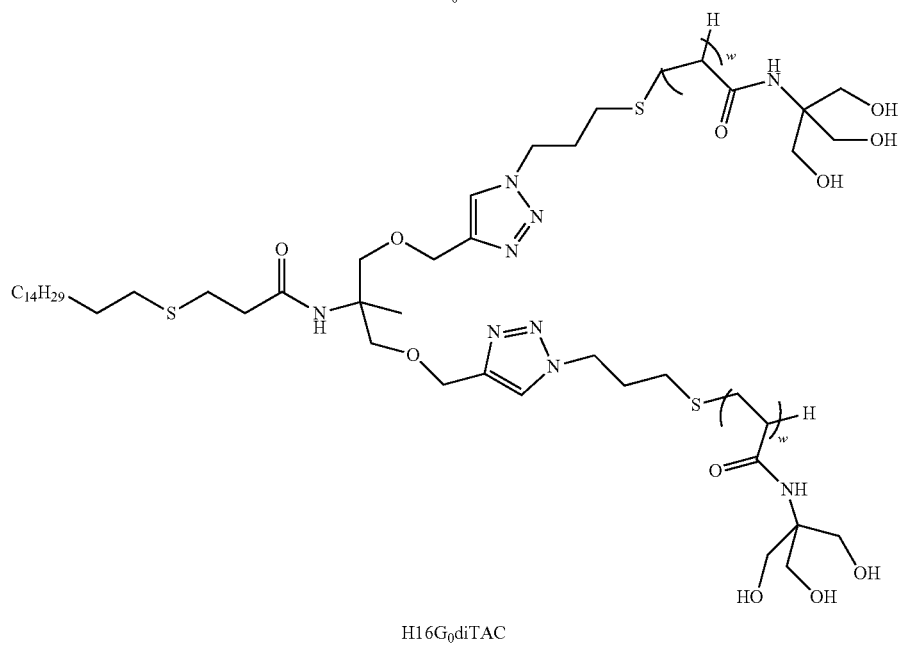

H16G₀diTAC wherein w is as defined above.

Nanoemulsions

In a second aspect, the invention provides a nanoemulsion comprising:
- as a discontinuous phase, a perfluorocarbon compound,
- as a continuous phase, an aqueous phase,
- an amphiphilic dendrimer as defined above.

In one embodiment, the invention provides a nanoemulsion comprising:
- as a discontinuous phase, a perfluorocarbon compound,
- as a continuous phase, an aqueous phase,
- a fluorinated amphiphilic dendrimer, as defined above.

In another embodiment, the invention provides a nanoemulsion comprising:
- as a discontinuous phase, a perfluorocarbon compound,
- as a continuous phase, an aqueous phase,
- a hydrocarbon amphiphilic dendrimer, as defined above.

In one embodiment, there is included a nanoemulsion wherein the discontinuous phase is loaded with solubilized oxygen.

In a particular embodiment, the solubilized oxygen in the droplet has a concentration at least 10 times, notably from 10 to 50 times higher than that of oxygen solubilized in the continuous aqueous phase.

In a particular embodiment, the invention provides a nanoemulsion comprising:
- as a discontinuous phase, a perfluorocarbon compound,
- as a continuous phase, an aqueous phase,
- an amphiphilic dendrimer, as defined above,
- a biocompatible hydrocarbon oil.

Said amphiphilic dendrimer is a fluorinated or a hydrocarbon amphiphilic dendrimer, as defined above.

In an advantageous embodiment, the invention provides a nanoemulsion comprising:
- as a discontinuous phase, a perfluorocarbon compound,
- as a continuous phase, an aqueous phase,
- a hydrocarbon amphiphilic dendrimer, as defined above,
- a biocompatible hydrocarbon oil.

By "biocompatible hydrocarbon oil" is meant an oil that is not toxic to the human body, being in particular acceptable in the pharmaceutic, cosmetic or food industry, and that does comprise at least one hydrocarbon group but no fluorocarbon or perfluorocarbon groups. The biocompatible oil is in particular chosen among pure or mixture of biocompatible long-(composed of C13 to C18 chain fatty acids), medium- (composed of C6 to C12 chain fatty acids) or short-(composed of C<6 chain fatty acids) chain triglycerides, biocompatible fatty acids, biocompatible fatty acids esters or biocompatible hydrocarbons.

More particularly, the biocompatible hydrocarbon oil is chosen from triacetin, tripropionin, tributyrin, coconut oil, soybean oil, castor oil, isopropyl palmitate, isopropyl myristate, squalene or squalane.

In still another embodiment, there is included a nanoemulsion, wherein the discontinuous phase further comprises a sonosensitive agent and/or an active ingredient.

In still another embodiment, there is included a nanoemulsion, wherein the discontinuous phase further comprises a sonosensitive and/or photosensitive agent and/or an active ingredient.

In still another embodiment, there is included a nanoemulsion, wherein the discontinuous phase further comprises a sonosensitive and/or photosensitive agent and/or an active ingredient, said nanoemulsion further comprising a biocompatible hydrocarbon oil.

Figure 4:
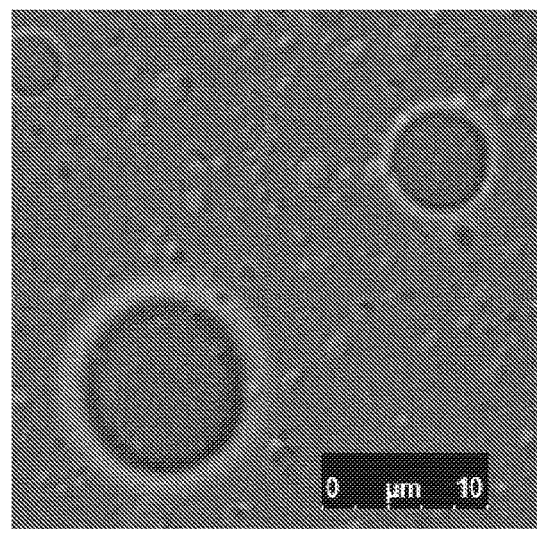

Drug encapsulation into the droplets forming the discontinuous phase of the nanoemulsion is for example achieved by:
- adding a biocompatible hydrocarbon oil as defined above, for example triacetin, tripropionin, tributyrin, coconut oil, soybean oil, castor oil, isopropyl palmitate, isopropyl myristate, squalene or squalane. The oil may be added to the emulsion during its preparation after obtention of a two-phases solution and before using the ultrasonic homogenizer or microfluidizer. It may be observed that the oil forms a corona around the perfluorocarbon droplet, and the surfactant forms a shell around this oily corona (see FIG. 4); The use of a hydrocarbon amphiphilic dendrimer as defined above may, in that case, be particularly relevant to increase the concentration of encapsulated drug in the nanoemulsion;
- adding a fluor moiety to the drug which can be encapsulated inside the perfluorocarbon core or in the shell.

In yet another embodiment, there is included a nanoemulsion, wherein the sonosensitive agent is selected from protoporphyrin IX (PpIX), hematoporphyrin (Hp), photofrin II, hematoporphyrin monomethyl ether (HMME), ATX-70, chlorin e6, ATX-S10, sinoporphyrin sodium (called DVDMS) (Chen et al. Drug Discovery Today, 19, 2014, 502-509).

In yet another embodiment, there is included a nanoemulsion, wherein the sonosensitive and/or photosensitive agent is selected from protoporphyrin IX (PpIX), hematoporphyrin (Hp), photofrin II, hematoporphyrin monomethyl ether (HMME), ATX-70, chlorin e6, chlorin family (dihydroporphyrin), bacteriochlorin family (tetrahydroporphyrin), ATX-S10, sinoporphyrin sodium (called DVDMS) or a chlorophyll-derived porphyrin analogue (Chen et al. Drug Discovery Today, 19, 2014, 502-509).

In yet another embodiment, there is included a nanoemulsion, wherein the sonosensitive and/or photosensitive agent is a PPIX derivative of the following formula:

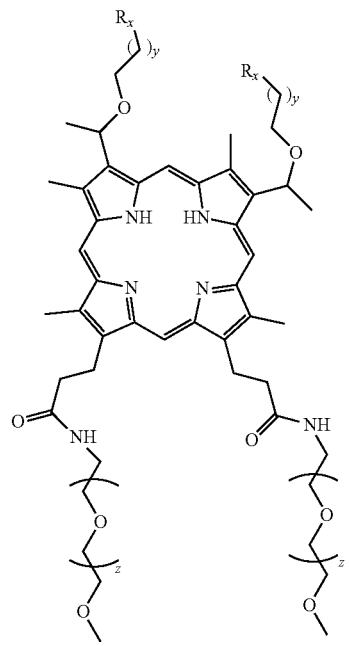

wherein
$R_x$ is a $C_1$-$C_{10}$ perfluoroalkyl or a $C_1$-$C_{24}$ alkyl group,
y is 0, 1, 2, 3 or 4,
z is 1 to 200.

In particular, z is 6, 7, 8, 9, 10, 11, 12, 13, 14, 15, 16, 17 or 18.

In another aspect, the invention provides the PPIX derivative as defined above.

Nanoemulsions for Use in In Vivo Diagnosis and/or for its Therapeutical Use

In a third aspect, the invention provides a nanoemulsion for its use in in vivo diagnosis and/or for its therapeutical use.

In one embodiment, there is included a nanoemulsion for use in tumor imaging. The tumor imaging may notably be selected from contrast echography, photoacoustic imaging, near-infrared fluorescence (NIR) and Magnetic Resonance Imaging (MRI), in particular from ultrasound echography and fluorine Nuclear Magnetic Resonance.

In another embodiment, there is included a nanoemulsion for use in the treatment of cancer.

In still another embodiment, there is included a nanoemulsion for use in sonodynamic therapy (Rosenthal et al, Ultrasonics Sonochemistry, 11, 2004, 349-363) and/or for photodynamic therapy.

In yet another embodiment, there is included a nanoemulsion for its use as defined above, wherein the terminal group of the dendrimer comprises or is attached to a targeting ligand, for instance, notably a tumor targeting peptide such as a RGD peptide (H. Kessler et al, Anti-Cancer Agents in Medicinal Chemistry, 10, 2010, 753-768).

Nanoparticles

In a fourth aspect, the invention provides a nanoparticle comprising:
- a core containing a perfluorocarbon compound,
- a shell composed of amphiphilic dendrimers as defined above.

In a particular embodiment, the invention provides a nanoparticle comprising:
- a core containing a perfluorocarbon compound, said core being surrounded by a layer of biocompatible hydrocarbon oil,
- a shell composed of amphiphilic dendrimers as defined above.

Said amphiphilic dendrimer is a fluorinated or a hydrocarbon amphiphilic dendrimer, as defined above.

Process of Preparation

In another aspect, the invention provides a process of preparation of a nanoemulsion comprising:
- as a discontinuous phase, a perfluorocarbon compound,
- as a continuous phase, an aqueous phase,
- an amphiphilic dendrimer as defined above,
- optionally a biocompatible hydrocarbon oil, said process comprising:
- a step of emulsifying a system comprising:
  - an aqueous phase comprising an amphiphilic dendrimer as defined above,
  - a perfluorocarbon compound,
  - optionally a biocompatible hydrocarbon oil,
- to obtain said nanoemulsion.

The emulsifying step can be conducted thanks to the techniques known by the man skilled in the art, in particular by using an ultrasonic homogenizer or a microfluidizer.

In an embodiment, the step of emulsifying is followed by a step of storage of the obtained nanoemulsion, in particular by freezing or freeze-drying, to obtain a stored nanoemulsion, and then a step of obtaining a ready-to-use nanoemulsion from the stored nanoemulsion, in particular by defrosting or by resuspending the nanoemulsion in water.

In a particular embodiment, said process comprises:
- a step of emulsifying a system comprising:
  - an aqueous phase comprising an amphiphilic dendrimer as defined above,
  - a perfluorocarbon compound,
  - optionally a biocompatible hydrocarbon oil,
- to obtain said nanoemulsion;
- a step of freezing said nanoemulsion to obtain a freezed nanoemulsion;
- a step of defrosting said freezed nanoemulsion to obtain a nanoemulsion, ready for use.

In another particular embodiment, said process comprises:
- a step of emulsifying a system comprising:
  - an aqueous phase comprising an amphiphilic dendrimer as defined above,
  - a perfluorocarbon compound,
  - optionally a biocompatible hydrocarbon oil,
- to obtain said nanoemulsion;
- a step of freeze-drying said nanoemulsion to obtain a freeze-dryed nanoemulsion;
- a step of suspending said freeze-dryed nanoemulsion in water to obtain a nanoemulsion, ready for use.

DEFINITIONS

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkylene" refers to a branched or straight chained hydrocarbon of 1 to 6 carbon atoms, which is formed by the removal of two hydrogen atoms. A designation such as "C1-C4 alkylene" refers to an alkylene radical containing from 1 to 4 carbon atoms. Examples include methylene (—CH2-), 1,2-ethandiyl (—CH2CH2-), etc.

As used herein, the term "perfluoroalkyl" refers to a branched or straight chained hydrocarbon of 1 to 6 carbon atoms, in which the hydrogen atoms are replaced with fluorine atoms.

FIGURES

FIG. 1. MRI spectra of emulsion made of DendriTAC surfactant and PFOB. a) and b): Relative magnitude spectra, using low (20°) and respectively high (90°) flip angle. TR=205 ms. c): non-selective excitation heavily T1-weighted image of the same sample (TR=10 ms, FA=45°)

Figure 2:
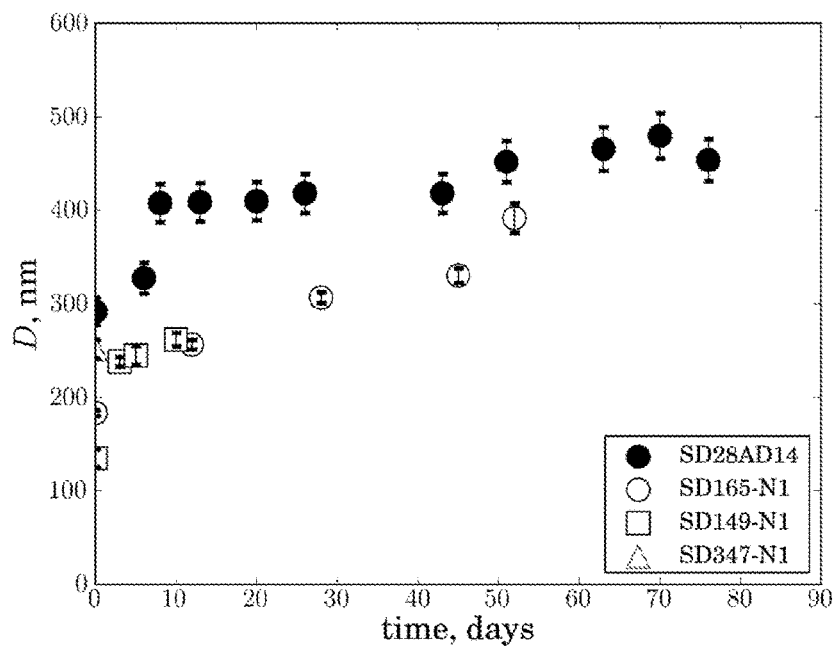

FIG. 2. Variation of the mean diameter, D, of doplets made of DentriTAC and PFOB. The black dot (●) are variation when using the SD28AD14 surfactant with an ultrasonic homogenizer to prepare the emulsion. Circles (○), squares (□), and (Δ) are respectively for the SD165, SD149, and SD347 surfactants when using high-pressure microfluidizer. The use of a high-pressure microfluidizer allows to decrease by a factor two the droplet mean size as compared to an ultrasonic homogenizer. The black dot and square were determined by qNano and the circles by DLS.

Figure 3:
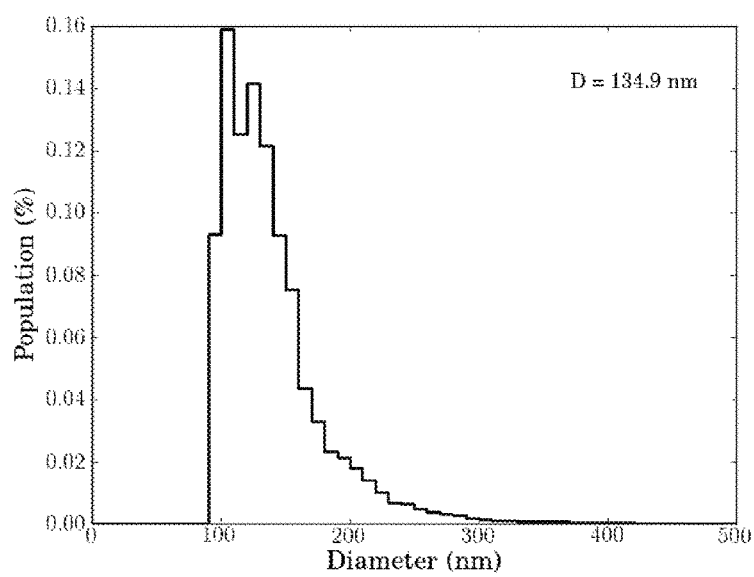

FIG. 3. Size distribution of an emulsion prepared with SD149 and PFOB using high-pressure microfluidizer and measured by qNano at the day of preparation. The mean diameter equals to 134.9 nm FIG. 4. Micrometric droplets containing a volume of triacetin where FITC has been solubilized. It can be observed that the triacetin forms a corona around the PFOB core.

Figure 5:
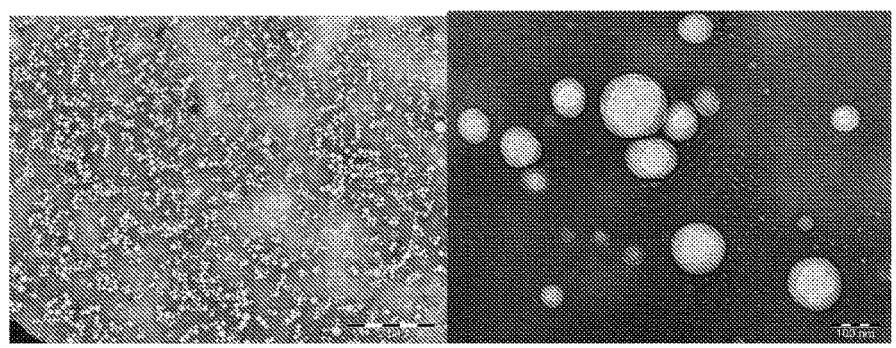

FIG. 5. TEM images (two different magnifications) of perfluorocarbon-nanoemulsions with DiF6diTAC6 as surfactant, performed after centrifugation of the nanoemulsion at 900 g for 1 min, according to example 11.

Figure 6:
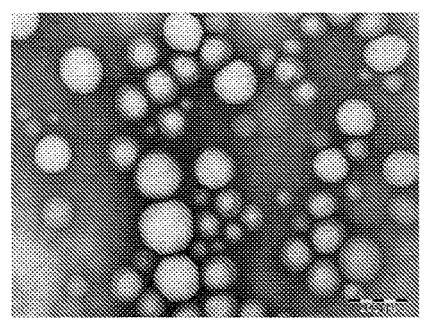

FIG. 6. TEM image of perfluorocarbon-nanoemulsions with F6diTAC10 as surfactant, performed after centrifugation of the nanoemulsion at 900 g for 1 min, according to example 11.

Figure 7:
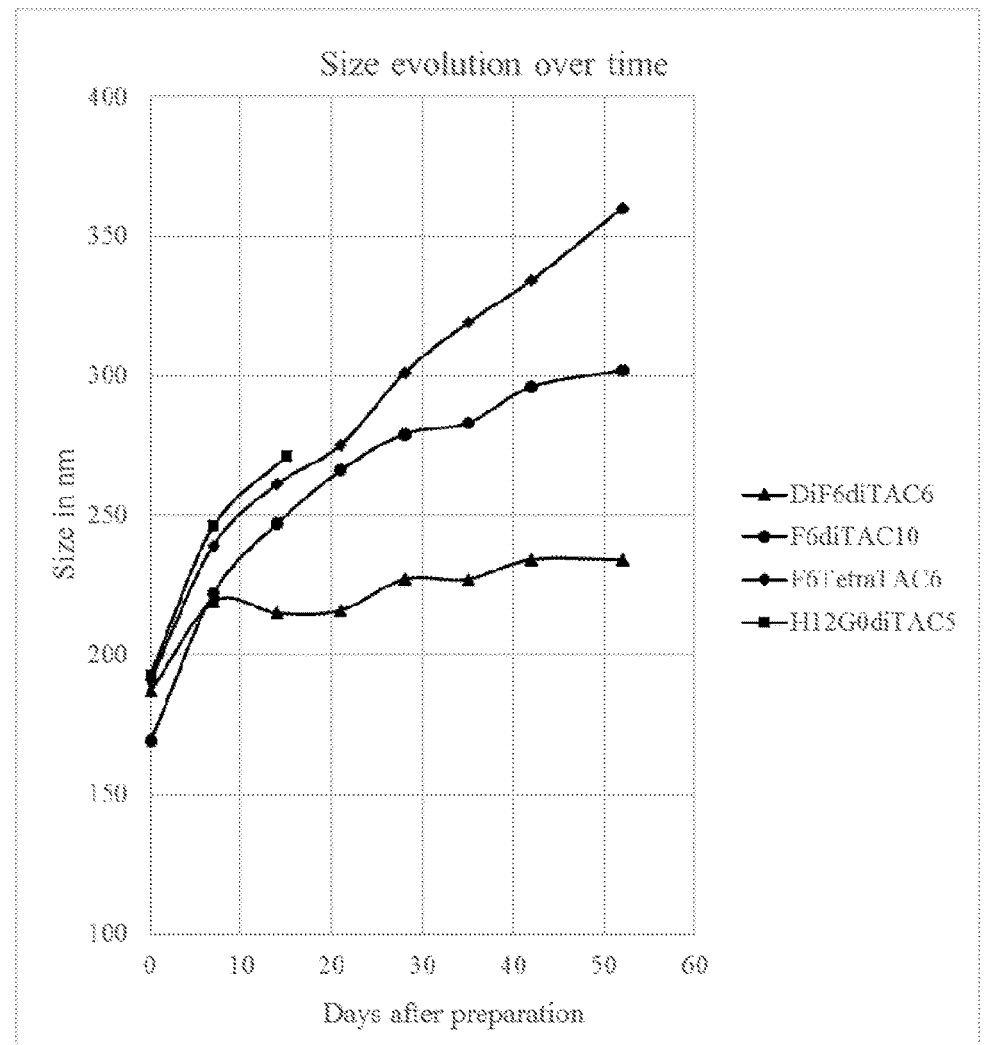

FIG. 7. Nanodroplets hydrodynamic diameter (measured by dynamic light scattering (DLS)) evolution over time, in the case of four different surfactants.

Figure 8:
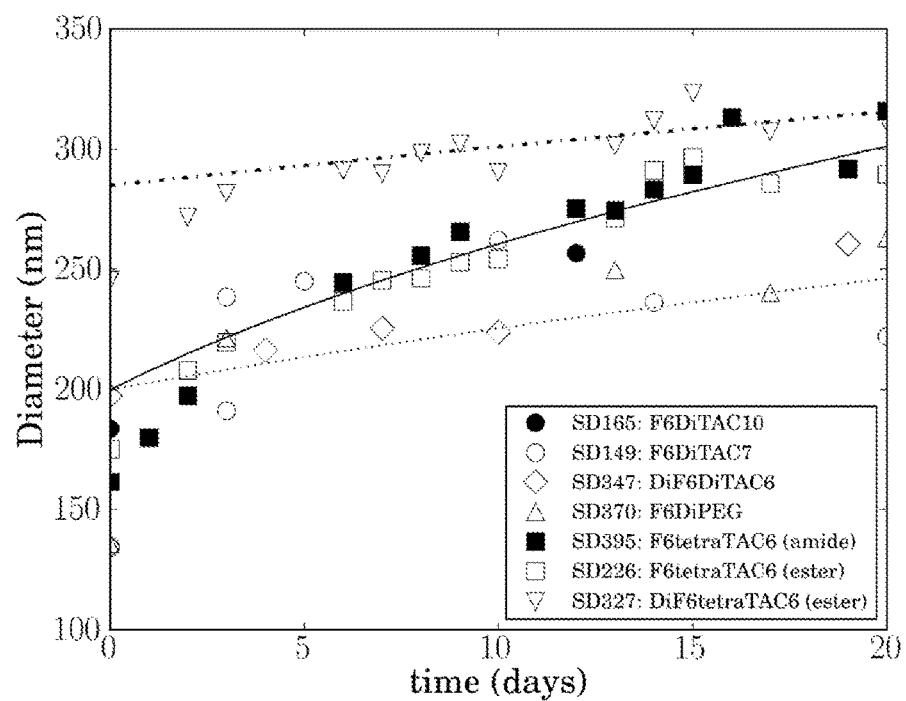

FIG. 8. Size evolution of NE prepared with a high pressure homogenizer (microfluidizer).

Figure 9:
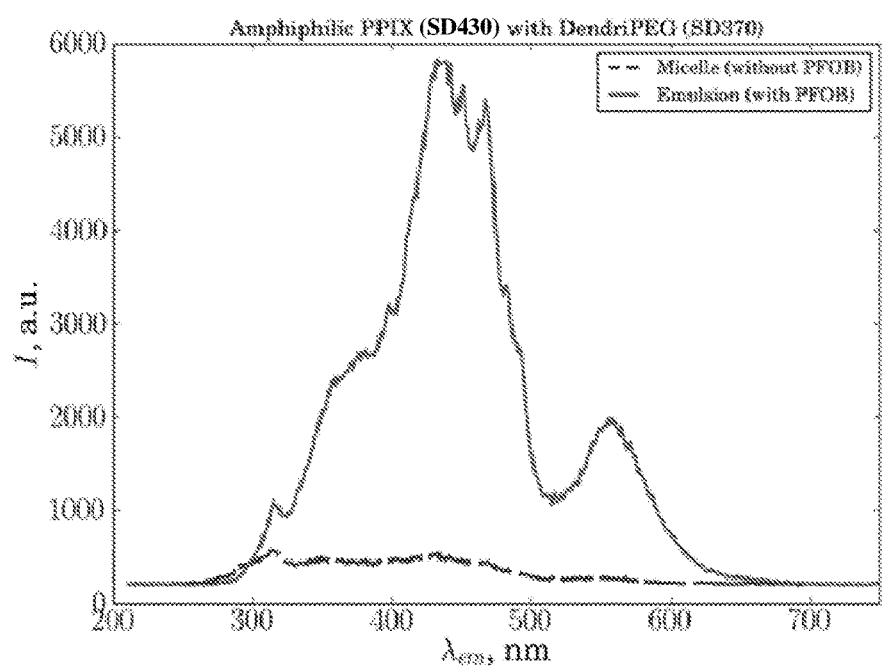

FIG. 9. Fluorescent spectrum of a solution of micelles made of SD430 (amphiphilic PPIX) and SD370 (Dentri-TAC) prepared before emulsification (dotted line), and of the solution after emulsification in the presence of PFOB (plain line). For both samples the molar ratio [SD370]/[SD430]=40,000.

Figure 10:
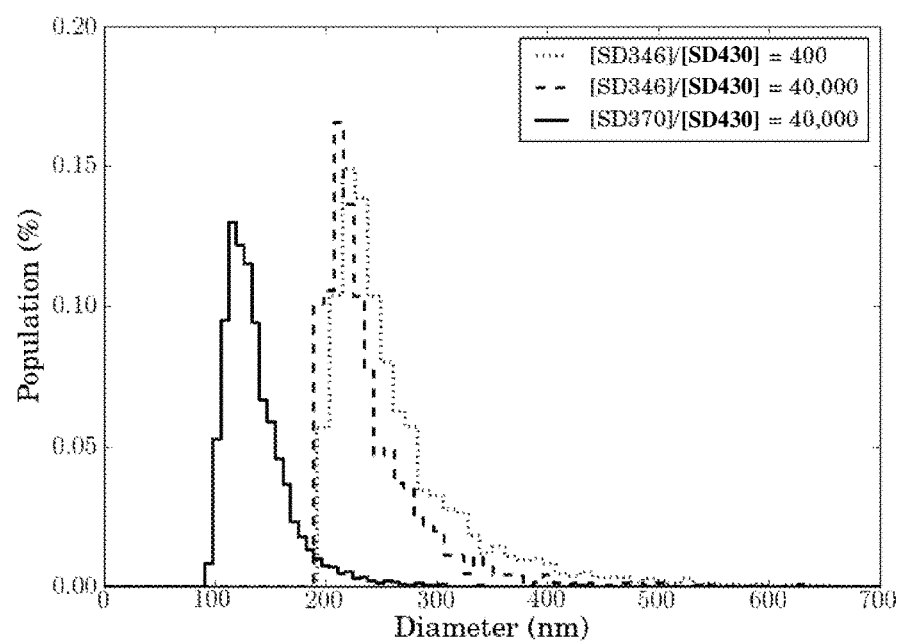

FIG. 10. Size distribution of NE for different [DentriTAC or F-TAC]/[Amphiphilic PPIX] ratio.

Figure 11:
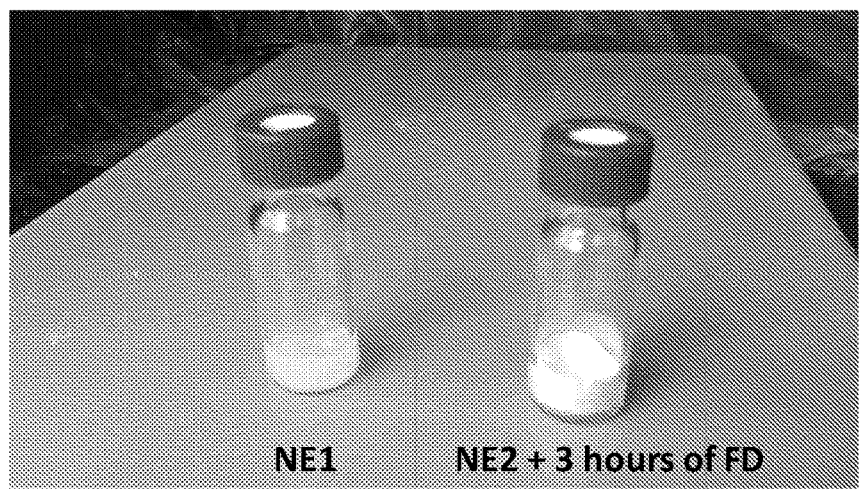

FIG. 11. Pictures of the NE1 and NE1 samples according to example 11.

EXAMPLES

1. General Procedure

All reagents were from commercial sources and were used as received. All solvents were distilled and dried according to standard procedures. Reactions were checked for completions by TLC (EM Science, silica gel 60 F 254) which were visualized by quenching of u.v. fluorescence ($\lambda_{max}$=254 nm) or by spraying a 5% sulfuric acid solution in ethanol or a 2% ninhydrin solution in ethanol, and then by heating at ~150° C. Flash chromatography were performed using silica gel 60 (40-63 μm, 230-400 mesh) or on combiflash Rf 200 apparatus from Teledyne Isco equipped with a UV detector. Size exclusion chromatography was carried out on hydroxypropylated cross-linked dextran (LH 20) from GE Healthcare. Fluorous solid-phase extractions were performed on Fluorochrom columns from SiliCycle®.

HR-MS spectra were recorded on a mass spectrometer equipped with a TOF analyzer for ESI+experiments at the Laboratoire de Mesures Physiques of University Montpellier 2 (IBMM instrument platform).

NMR spectra were recorded on BRUCKER Avance 400 spectrometerr. Samples were prepared in $CDCL_3$ (referenced to 7.26 ppm for $^1H$ and 77.16 for $^{13}C$), DMSO-d6 (referenced to 2.51 ppm for $^1H$ and 39.52 ppm for $^{13}C$), MeOD (referenced to 3.31 ppm for $^1H$ and 49.00 for $^{13}C$), $D_2O$ (referenced to 4.79 ppm for $^1H$). Coupling constant (J) are in Hertz and corrected to the nearest 0.5 Hz. Multiplicities are reported as follows: s, singlet, d, doublet, dd, doublets of doublets, t, triplet, q, quartet, m multiplet, c, complex, and br broad pic. $^1H$ NMR spectral assignments are supported by $^1H$-$^1H$ COSY and $^{13}C$-$^1H$ HSQC. Carbon spectra are supported by $^{13}C$-$^1H$ HSQC analysis where necessary.

2. Synthesis of Oligomeric Hydrosoluble polyTRIS Moieties

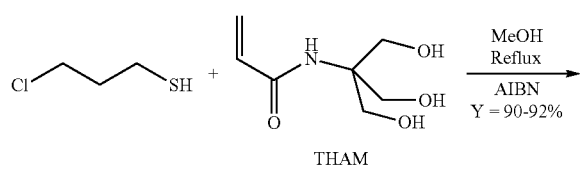

THAM

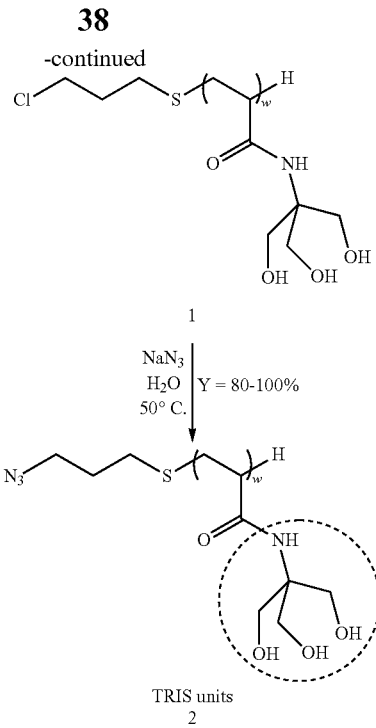

2.1. Synthesis of Chloro-polyTRIS Oligomer

Synthesis of Chloro-polyTRIS Oligomer 1a with DPn=9.4 (SD117)

To a solution of Tris(hydroxymethyl)acrylamidomethane (THAM) (8 g, 45.7 mmol, 12.5 eq) in dry and degassed MeOH under reflux, are added AIBN as radical initiator (60 mg, 0.365 mmol, 0.1 eq) and Chloropropanethiol as transfer reagent (354 μl, 3.65 mmol, 1 eq). The mixture is heated at reflux under nitrogen atmosphere until the total disappearance of the starting monomer THAM (monitored by TLC). Then the solution is filtered, concentrated and precipitated twice in $Et_2O$ to give 1a (7.8 g) as a pure white compound (yield=92.8%). The DPn is assessed by 1H-NMR in MeOD, where the integral of the peak at 2.04 ppm is set for 2 protons (middle $CH_2$ of the CTA (chain transfer agent)), and by dividing the integral of the $CH_2$ protons of Tris(hydroxymethyl)aminomethane (TRIS) units at 3.80 ppm by six. DPn= ($\int$CH2 at 3.80 ppm)/6.

$^1H$ NMR (MeOD, 400 MHz) δ, 3.80 (56H, br, $CH_2$—OH), 3.70 (2H, br, $CH_2$—Cl), 2.72-2.50 (4H, c, $CH_2$—$CH_2$—$CH_2$—S, S—$CH_2$), 2.48-2.11 (5H, c, $CH_{OLIGOMER}$), 2.00 (2H, m, $CH_2$—$CH_2$—$CH_2$—S), 1.93-1.39 (8H, c, $CH_2$ $_{OLIGOMER}$).

Synthesis of Chloro-polyTRIS Oligomer 1b with DPn=5.2 (SD151)

To a solution of THAM (5 g, 28.6 mmol, 5 eq) in dry and degassed MeOH under reflux are added AIBN (374 mg, 0.228 mmol, 0.4 eq) and Chloropropanethiol (551 μl, 5.7 mmol, 1 eq). The mixture is heated at reflux under a nitrogen atmosphere until total disappearance of the starting monomer THAM (monitored by TLC). Then the solution is filtered, concentrated and precipitated twice in $Et_2O$ to give 1b (5.24 g) as a pure white powder (yield=93.1%). The DPn is assessed by 1H-NMR in MeOD or $D_2O$, where the integral of the peak at 2.04 ppm is set for 2 Protons (middle CH$_2$ of the CTA (chain transfer agent)), and by dividing the integral of the CH$_2$ protons of TRIS at 3.80 ppm by six. DPn=(∫CH2 at 3.80 ppm)/6.

$^1$H NMR (D$_2$O, 400 MHz) δ, 4.02-3.71 (31H, br, CH$_2$—OH), 3.68 (2H, m, CH$_2$—Cl), 2.79-2.58 (4H, c, CH$_2$—CH$_2$—CH$_2$—S, S—CH$_2$), 2.56-2.11 (11H, c, CH$_{OLIGOMER}$), 2.04 (2H, br, CH$_2$—CH$_2$—CH$_2$—S), 1.93-1.39 (17H, c, CH$_2$ $_{OLIGOMER}$).

2.2. Synthesis of Azido-polyTRIS Oligomer

Synthesis of Azido-polyTRIS Oligomer 2a (SD150)

To a solution of oligomer 1a (4 g, 2.1 mmol, 1 eq) in water (30 ml), is added NaN$_3$ (419 mg, 6.41 mmol, 3 eq). The reaction mixture is heated at 55° C., after 12H another 3 eq of NaN$_3$ is added and the solution is heated for another 12H. The solvent is removed under vacuum and the crude is purified over LH20 with pure MeOH. 3.77 g of 2a are recovered as a white powder (yield=94%). (D$_2$O, 400 MHz) δ, 3.90-3.59 (CH$_2$—OH), 3.44 (CH$_2$—N$_3$), 2.71-2.48 (CH$_2$—S—CH$_2$), 2.46-2.00 (CH$_{OLIGOMER}$), 1.84-1.25 (25H, c, CH$_2$—CH$_2$—CH$_2$—S, CH$_2$ $_{OLIGOMER}$).

Synthesis of Azido-polyTRIS Oligomer 2b (SD144)

To a solution of oligomer 1b (4.23 g, 4 mmol, 1 eq) in water (30 ml), is added NaN$_3$ (780 mg, 12 mmol, 3 eq). The reaction mixture is heated at 55° C., after 12H another 3 eq of NaN$_3$ are added and the solution is heated for another 12H. The solvent is removed under vacuum and the crude is purified over LH20 with pure MeOH. 3.4 g of 2b are recovered (yield=80%). (D$_2$O, 400 MHz) δ, 3.91-3.74 (CH$_2$—OH), 3.44 (CH$_2$—N$_3$), 2.77-2.58 (—CH$_2$—S—CH$_2$), 2.56-2.11 (CH$_{OLIGOMER}$), 1.93-1.44 (CH$_2$—CH$_2$—CH$_2$—S, CH$_2$ $_{OLIGOMER}$).

3. Synthesis of PEG Hydrosoluble Moieties 3.1 Synthesis of Compound 1-O-Mesyl-ω-Methoxy-PEG550 (3) (SD214)

To a solution of monomethylPEG 550 (5 g, 9.0 mmol, 1 eq.) in 130 mL of DCM and 11 mL of DIEA (63 mmol, 7 eq.), cooled to 0° C., was slowly added 3.5 mL of mesyl-chloride (45 mmol, 5 eq.). The solution was stirred for 16 h at room temperature under dry N$_2$ blanket. The mesyl chloride remaining was neutralized with MeOH, then the solution was concentrated under reduced pressure and the residue was purified by column chromatography over SiO$_2$ (AcOEt/methanol 95:5) to give 3.5 g of compound 3 as slightly orange oil (yield 62%). TLC Rf=0.31 (Dichloromethane/Methanol 9.5/0.5).

$^1$H NMR (400 MHz, CDCl$_3$) δ 4.37 (m, 2H), 3.75 (m, 2H), 3.64 (m, 49H), 3.54 (m, 2H), 3.69 (s, 3H, OMe), 3.08 (s, 3H, mesyl). $^{13}$C NMR (100 MHz, CDCl$_3$) δ 72.04, 70.75-70.62 (m), 69.43, 69.14, 59.16 (OMe), 37.86 (mesyl).

3.2 Synthesis of Compound 1-azide-ω-methoxy-PEG550 (4) (SD363)

To a solution of 3 (1.8 g, 2.86 mmol, 1 eq.) in 20 mL of DMF was added 558 mg of sodium azide (8.60 mmol, 3 eq.). The solution was stirred for 72 h at room temperature; then the reaction is concentrated under reduced pressure, dissolved in 20 ml of AcOEt and subsequently filtrated. The filtrate is concentrated under high vacuum to give 1.64 g of compound 4 as slightly orange oil (quantitative yield).

$^1$H NMR (400 MHz, CDCl$_3$) δ 3.65-3.62 (m, 48H), 3.54 (m, 2H), 3.39-3.37 (m, 5H, CH$_2$, OMe). $^{13}$C NMR (100 MHz, CDCl$_3$) δ 72.26, 70.65, 70.13, 59.13 (OMe), 50.79 (CH$_2$—N$_3$).

4. Amphiphilic Dendrimers Functionalized with polyTris Moieties-Generation 0 (G$_0$)

4.1. Monocatenar Amphiphilic Dendrimers with AB$_2$ Building Blocks: F6G$_0$diTAC 4.1.1. Synthesis of the Monocatenar Scaffold (Mickaël Addition) F6G$_0$ (AB2)

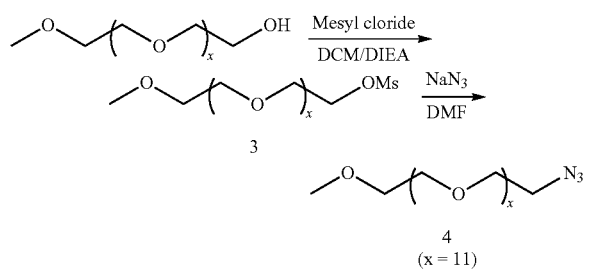

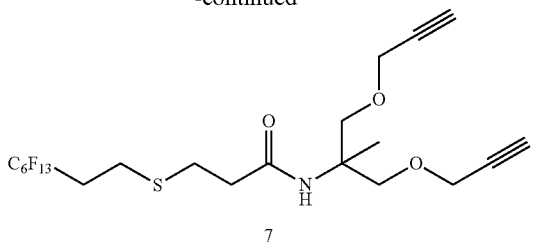

Synthesis of Compound N-(1,3-dihydroxy-2-methylpropan-2-yl)acrylamide (5)

This synthesis was already described in Journal of fluorine chemistry by M. Abla, G. Durand, C. Breyton, S. Raynal, C. Ebel, B. Pucci, J. Fluor. Chem. 134, 63 (2012).

Synthesis of Compound N-(2-methyl-1,3-bis(prop-2-yn-1-yloxy)propan-2-yl)acrylamide (6) (SD145)

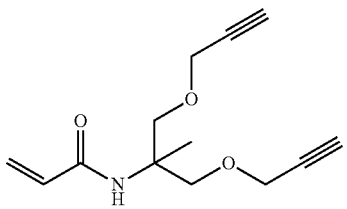 [SMILES: C#CCOCC(C)(COCC#C)NC(=O)C=C]

To a solution of 5 (1 eq, 2.00 g, 13 mmol) and propargyl bromide (2.3 eq, 3.27 ml, 30 mmol) dissolved in 40 ml of dry DMF and cooled at 0° C., is added finely grinded KOH (2.1 eq, 1.50 g, 26 mmol) in portions over a period of one hour. The reaction mixture is left to warm and stirred overnight at room temperature. The mixture is diluted with 200 ml of EtOAc and washed 4 times with water. All organic phases are pooled, dried over $Na_2SO_4$ and concentrated in vacuo to dryness. The crude product is purified by silica gel column chromatography (cyclohexane/EtOAc 9:1-7:3 as eluent) to afford 1.48 g of pure white powder (yield=50%). TLC Rf=0.3 (Cyclohexane/Ethyl acetate 7/3).

$^1$H NMR (CDCl$_3$, 400 MHz) δ 6.24-6.11 (3H, m, CH$_2$=CH, NH), 5.58 5.58 (1H, dd, J=4.0, 2.0 Hz CH 4.16 (3H, s, CH$_2$), 4.24-4.27 (1H, t, J=6.2 Hz), 2.53 (2H, t, J=4.0 Hz), 1.43 (3H, s, CH$_3$); $^{13}$C NMR (CDCl$_3$, 100 MHz) δ 165.10 (C=O), 131.78.67 (CH$_2$=CH), 125.72 (CH$_2$=CH), 79.44 (CH), 74.76 (CH), 71.70 (CH$_2$—O), 58.38 (CH$_2$—C), 56.28 (C), 18.96 (CH$_3$) ESI Calcd for C$_{13}$H$_{18}$NO$_3$: 236.13 [M+H$^+$], found m/z 236.13 [M+H$^+$]. HRMS Calcd for C$_{13}$H$_{18}$NO$_3$: 236.1287 [M+H$^+$], found m/z 236.1293 [M+H$^+$].

Synthesis of Compound N-(2-methyl-1,3-bis(prop-2-yn-1-yloxy)propan-2-yl)-3-((3,3,4,4,5,5,6,6,7,7,8,8,8-tridecafluorooctyl)thio)propanamide (7) (SD148)

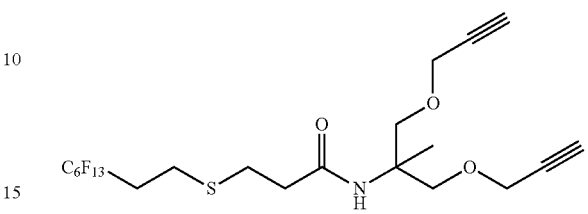

NaBH$_4$ (396 mg, 10.6 mmol, 2.5 eq) is added by portion to a cold solution of 1H, 1H, 2H, 2H perfluorooctanethiol (1.70 g, 4.46 mmol, 1.05 eq) in dry methanol (10 ml). The reaction mixture is stirred for 30 mn at 0° C. Then this solution is carefully added to a solution of 6 (1 g, 4.25 mmol, 1 eq) in dry methanol (90 ml) and the resulting mixture is stirred for 24 h. After 24 h another 0.5 eq of 1H, 1H, 2H, 2H perfluorooctanethiol and NaBH$_4$ are added in the same way as previously and the mixture is stirred for another 24 h. The solvent is evaporated in vacuo to dryness, the crude is purified over silica gel (cyclohexane/EtOAc 9:1-7:3 as eluent) to afford compound 7 (1.50 g, yield=57%) as a pure product. TLC Rf=0.42 (Cyclohexane/Ethyl acetate 7/3).

$^1$H NMR (CDCl$_3$, 400 MHz) δ (5.81 (1H, NH, s), 4.16 (4H, d, J=2.5 Hz CH$_2$-Alkyne), 3.62 (2H, d, J=9 Hz, CH$_2$—O), 3.50 (2H, d, J=9.0 Hz, CH$_2$—O), 2.82 (2H, t, J=7.0 Hz), 2.74 (2H, t, J=9.0 Hz (CH$_2$—S), 2.38-2.20 (6H, m, CF$_2$—CH$_2$, CH, CH$_2$—C=O), 1.29 (3H, s, CH$_3$); $^{13}$C NMR (CDCl$_3$, 100 MHz) δ 170.63 (C=O), 79.48 (CH), 74.63 (CH), 71.91 (CH$_2$—O), 58.52 (CH$_2$—C), 56.22 (C), 37.17 (CH$_2$—C=O), 31.99 (CH$_2$—CF$_2$), 27.60 (CH$_2$—S), 22.80 (CF$_2$—CH$_2$), 19.04 (CH$_3$); $^{19}$F NMR (CDCl$_3$, 100 MHz) −81.44 (3H, t, J=10.0 Hz), −114.70 (2H, q, J=15.0 Hz), −122.32 (2H, br s, J=12.0 Hz), −123.32 (2H, br s), −123.76 (2H, br s), −126.66 (2H, br s). ESI Calcd for C$_{21}$H$_{23}$F$_{13}$NO$_3$S: 616.12 [M+H$^+$], found m/z: 616.12 [M+H$^+$]. HRMS Calcd for C$_{21}$H$_{23}$F$_{13}$NO$_3$S: 616.1191 [M+H$^+$], found m/z 616.1191 [M+H$^+$].

4.1.2. Functionalization with Hydrophilic PolyTris Moieties

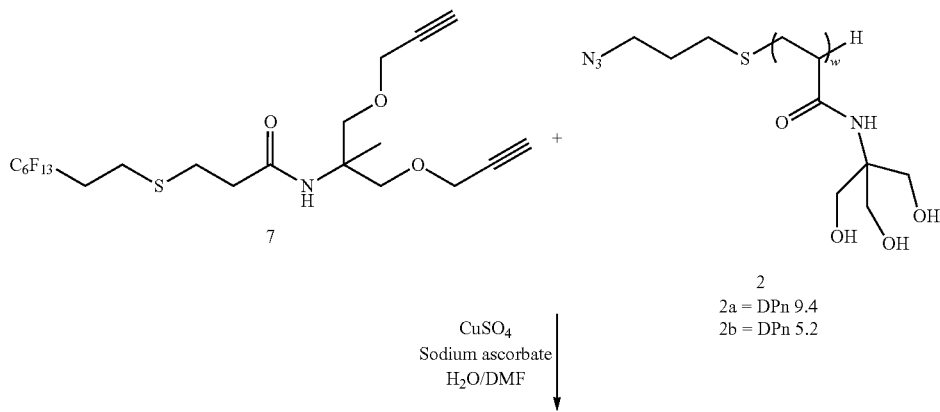

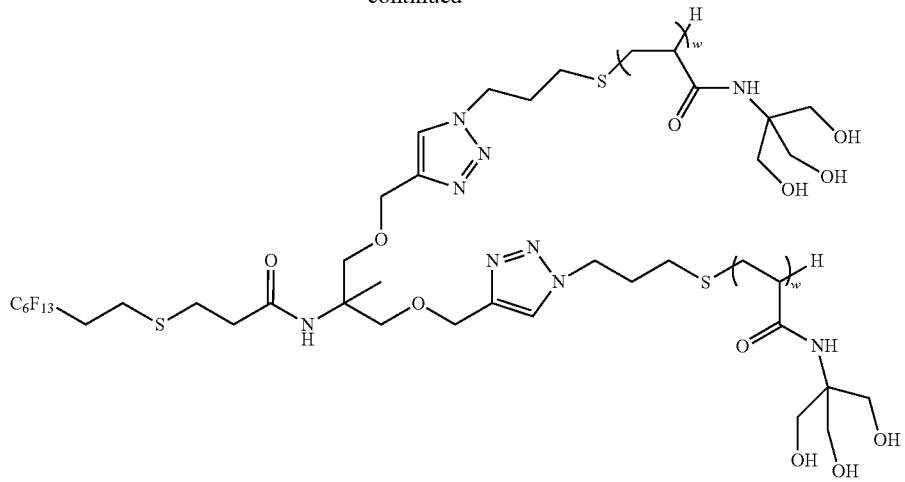

Y = 72.5% for F6 G0 diTAC (10*2)
Y = 19.8% for F6 G0 diTAC (7*2)

a—Synthesis of F6 G$_0$diTAC (10*2) (SD165)

Sodium ascorbate (169 mg, 0.85 mmol, 1.2 eq), compounds 7 (438 mg, 0.732 mmol, 1 eq) and 2a (3.71 g, 2 mmol, 2.8 eq) (DPn=9.4) are dissolved in DMF (40 ml), the reaction mixture is heated at 50° C., and after 5 minutes copper sulfate pentahydrate (71 mg, 0.28, 0.2 eq) is added. The solution is heated overnight. The solution is filtered and passed through chelex beads, and then the solvent is evaporated under vacuum. The crude is dissolved in a mixture of MeOH/water 9/1, filtered and purified over LH20 MeOH/H$_2$O 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature out of the water bath, then diluted with water and freeze dried. The product is further purified by fluorous solid-phase extraction (FSPE). Briefly, the column is equilibrated with 25 ml of a mixture of water and DMF (9/1), then between 100 mg and 400 mg of product are dissolved in 1 ml of this mixture and deposit onto the column, after 25 ml of this eluent is pass through the column to get rid of non-fluorous compounds, then 25 ml of water, followed by 25 ml of a mixture of MeOH and Water (9/1) and finally 25 ml of pure methanol in order to rinse the column. Eluents containing methanol are concentrated in vacuo, dilute with water and freeze dried in order to obtain a fluffy white powder. We obtain 2.25 g of compound SD165 with a DPn of 10; yield=72.5%.

The DPn is assessed by 1H-NMR in DMSO, where integrals of peaks at 4.40 and 4.49 ppm are set for 8 Protons (Two CH$_2$ in α position of the triazole ring), and by dividing the integral of the CH$_2$ protons of TRIS at 3.80 ppm by six or dividing the integral of the OH protons, between 5.48 and 4.64 ppm, by three.

$^1$H NMR (DMSO-d6, 400 MHz) δ (8.07 (2H, s, CH triazole), 7.75-6.85 (25H, c, NH), 5.48-4.64 (70H, c, OH), 4.49 (4H, s, C$_{TRIAZOLE}$—CH$_2$—O), 4.40 (4H, s, CH$_2$—CH$_2$—N$_{TRIAZOLE}$), 3.94-3.40 (143H, br, CH$_2$—OH, CH$_2$—O—), 2.71 (4H, c, CF$_2$—CH$_2$—CH$_2$—S, S—CH$_2$—CH$_2$—C=O), 2.50 (2H, c, CF$_2$—CH$_2$), 2.45 (2H, br, CH$_2$—CH$_2$—CH$_2$—S), 2.36 (2H, t, J=7.54 Hz, CH$_2$—C=O), 2.29-1.84 (29H, c, CH$_2$—CH$_2$—CH$_2$—S, CH$_2$—S, CH, CH$_2$—C=O, CH—C=O$_{OLIGOMER}$), 1.80-1.28 (38H, m, CH$_{2\,OLIGOMER}$), 1.18 (3H, s, CH$_3$); $^{13}$C NMR (DMSO-d6, 100 MHz) δ 175.68 (C=O oligomer), 170.46 (C=O), 144.01 (C-triazole), 123.79 (CH-triazole), 71.54 (CH$_2$—O), 64.01 (C$_{TRIAZOLE}$—CH$_2$—O), 62.35 (C), 60.53 (CH$_2$—OH) 56.36 (C), 48.16 (CH$_2$—Ntriazole), 42.16 (C-oligomer), 41.59 (C-oligomer), 36.06 (CH$_2$—C=O), 31.13 (CH$_2$—CF$_2$), 28.27 (CH$_2$—CH$_2$—CH$_2$—S), 26.97 (CF$_2$—CH$_2$—CH$_2$—S), 21.77 (S—CH$_2$—CH$_2$—C=O), 19.23 (CH$_3$); $^{19}$F NMR (DMSO-d6, 100 MHz) −80.19 (3H, t, J=8.68 Hz), −113.22 (2H, br), −121.73 (2H, br), −122.65 (2H, br), 122.65 (2H, br) −125.74 (2H, br).

b—Synthesis of F6 G$_0$diTAC (7*2) (SD149)

Sodium ascorbate (285 mg, 1.44 mmol, 1.2 eq), compounds 7 (742 mg, 1.2 mmol, 1 eq) and 2 (3.82 g, 3.62 mmol, 3 eq) (DPn-5) are dissolved in mixture of DMF (100 ml) and water (100 ml), the reaction mixture is heated at 60° C., and after 5 minute copper sulfate pentahydrate (120 mg, 0.48, 0.2 eq) is added. The solution is heated at 60° C. during 3 hours and stirred at room temperature overnight. The solution is filtered and passed through chelex beads, and then the solvent is evaporated under high vacuum. The crude is dissolved in a mixture of MeOH/water 9/1 and filtered and then purified over LH20 MeOH/Water 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature without the water bath. The mixture is diluted with water, freeze dried and further purified by FSPE as previously described to give 650 mg of compound SD149 with a DPn of 7; y=19.8%.

The DPn was assessed by 1H-NMR as previously described for SD165.

$^1$H NMR (DMSO-d6, 400 MHz) δ (8.06 (2H, s, CH triazole), 7.75-6.81 (20H, c, NH), 5.48-4.62 (58H, c, OH), 4.50 (4H, s, C$_{TRIAZOLE}$—CH$_2$—O), 4.41 (4H, s, CH$_2$—CH$_2$—N$_{TRIAZOLE}$), 3.77-3.47 (122H, br, CH$_2$—OH), 2.29-1.84 (28H, c, CH$_2$—S, CF$_2$—CH$_2$, CH, CH$_2$—C=O, CH—C=O$_{OLIGOMER}$), 1.80-1.28 (36H, m, S—CH$_{2\,OLIGOMER}$), 1.24 (3H, s, CH$_3$); $^{19}$F NMR (DMSO-d6, 100 MHz) −80.44 (3H, br), −113.34 (2H, q, J=15.0 Hz), −121.92 (2H, br), −122.88 (4H, br), −125.97 (2H, br).

4.2. Bicatenar Amphiphilic Dendrimers with AB2 Building Blocks: diF6G0diTAC

4.2.1. Synthesis of the Bicatenar Scaffold DiF6G$_0$ (AB2)

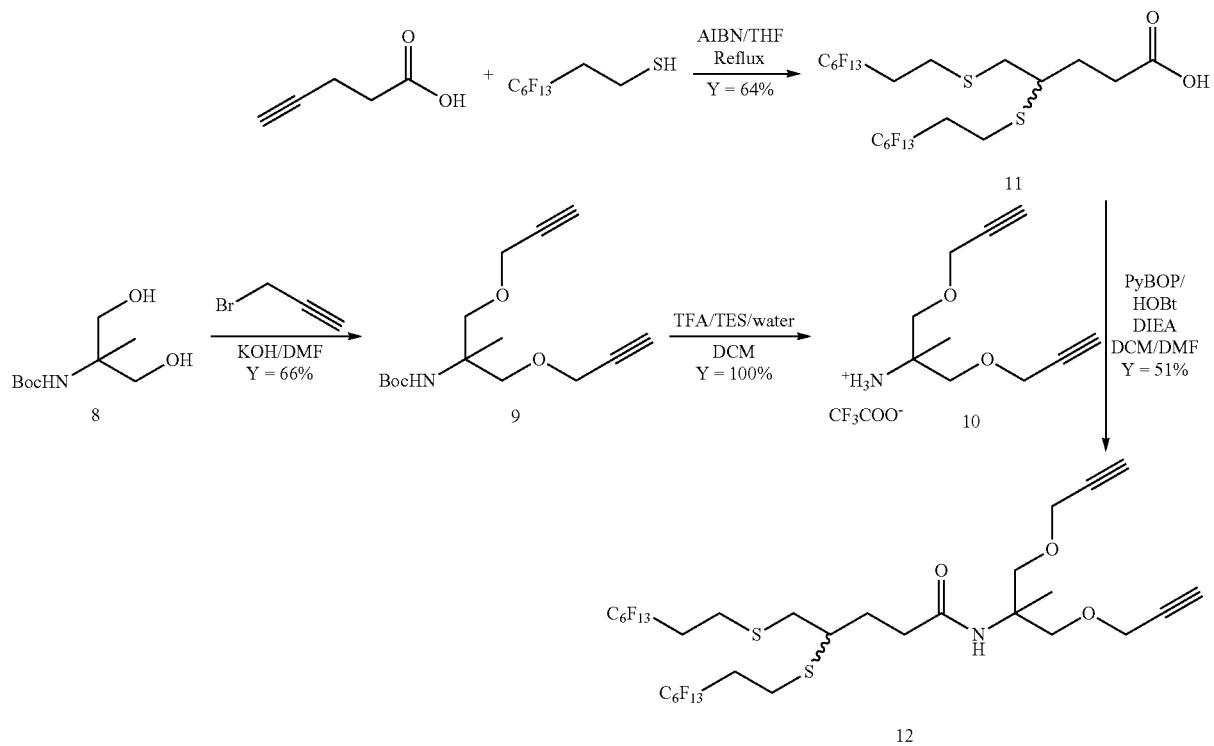

Synthesis of Compound tert-butyl (1,3-dihydroxy-2-methylpropan-2-yl)carbamate (8) (sd168)

2-amino-2-methyl-1,3 propanediol (5 g, 48 mmol, 1 eq), NaHCO$_3$ (8 g, 96 mmol, 2 eq), BOC$_2$O (17.7 g, 0.072 mmol, 1.5 eq) are dissolved in a mixture of MeOH (120 ml) and THF (30 ml) at 0° C. The reaction mixture is stirred overnight at room temperature, and then the solution is filtered and concentrated in vacuo. The crude is dissolved in EtOAc (300 ml) and the solution is washed three times with water (3×150 ml) and dried over Na$_2$SO$_4$. The solvent is removed in vacuo to give 8 as a white solid in quantitative yield (9.84 g). No purification is necessary.

$^1$H NMR (CDCl$_3$, 400 MHz) δ 5.05 (1H, NH, s), 3.79 (2H, OH), 3.74 (2H, dd, J=5.41, 11.46 Hz, CH$_2$—O), 3.61 (2H, dd, J=6.70, 11.46 Hz, CH$_2$—O), 1.43 (9H, s, CH$_3$ (Boc)), 1.16 (3H, s, CH$_3$); $^{13}$C NMR (CDCl$_3$, 100 MHz) δ 156.63 (C=O), 80.28 (C), 67.84 (CH$_2$—O), 57.24 (C), 28.46 (CH$_3$Boc), 20.52 (CH$_3$)—

Synthesis of compound tert-butyl (2-methyl-1,3-bis(prop-2-yn-1-yloxy)propan-2-yl)carbamate (9) (sd140)

To a solution of compound 8 (1 eq, 2.05 g, 10 mmol) and propargyl bromide (2.3 eq, 2.06 ml, 23 mmol) dissolved in 40 ml of dry DMF cooled to 0° C., was added finely grinded KOH (2.1 eq, 1.18 g, 21 mmol) by portions over a period of one hour. The resulting mixture was left to warm and stirred overnight at room temperature. The mixture was diluted with 200 ml of ethyl acetate, washed 4 times with water (4×100 ml and dried over Na$_2$SO$_4$. The crude product was purified by silica gel column chromatography (cyclohexane/ethyl acetate 9:1 as eluent) to afford 1.85 g of pure white compound (yield=66%). TLC Rf=0.66 (cyclohexane/ethyl acetate 7/3).

$^1$H NMR (CDCl$_3$, 400 MHz) δ 4.88 (1H, NH, s), 4.15 (4H, d, J=2.5 Hz CH$_2$—C), 3.65 (2H, d, J=9.06 Hz, CH$_2$—

O), 3.54 (2H, d, J=9.06 Hz, CH$_2$—O), 2.42 (2H, t, J=2.5 Hz), 1.42 (9H, s, CH$_3$ (Boc)), 1.34 (3H, s, CH$_3$); $^{13}$C NMR (CDCl$_3$, 100 MHz) δ 154.97 (C=O), 79.78 (CH×2), 74.64 (C), 72.45 (CH$_2$—O), 58.73 (CH$_2$-ALCYNE), 55.30 (C), 28.53 (CH$_3$Boc), 19.45 (CH$_3$). ESI Calcd for C$_{15}$H$_{24}$NO$_4$Na: 304.15 [M+H$^+$], found m/z 304.15 [M+H$^+$] HRMS Calcd for C$_{15}$H$_{23}$NO$_4$Na: 304.1525 [M+Na$^+$], found m/z 304.1524 [M+H$^+$].

Synthesis of Compound 2-methyl-1,3-bis(prop-2-yn-1-yloxy)propan-2-yl-ammonium-trifluoro-acetate (10) (sd141)

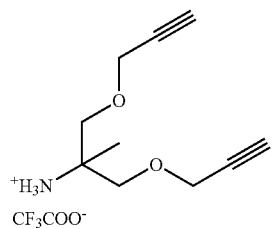

1.85 g (1 eq, 6.5 mmol) of compound 9 is dissolved in 20 ml of DCM at 0° C., with 1 ml (1 eq, 6.5 mmol) of triethylsilane and 117 μl (1 eq, 6.5 mmol) of water. Then 20 ml of cold TFA is added and the reaction is stirred at 0° C. for 45 min and at room temperature for another 75 min. The solvent is removed under high vacuum. The crude is dissolved in DCM and the solvent removed in vacuo, this procedure is repeated 3 times. The mixture is dried under high vacuum in order to obtain compound 10 as a pure product in quantitative yield. No purification is necessary.

$^1$H NMR (CDCl$_3$, 400 MHz) δ 7.90 (3H, br s, NH$_3^+$), 4.20 (4H, d, J=2.5 Hz, CH$_2$-Alkyne), 3.60 (4H, dd, J=26 Hz and 10 Hz, CH$_2$—O), 2.47 (2H, t, J=2.5 Hz, CH), 1.37 (3H, s, CH$_3$); $^{13}$C NMR (CDCl$_3$, 100 MHz) δ 78.69 (CAlcyne), 75.67 (CH), 70.59 (CH$_2$—O), 58.80 (CH$_2$—C), 57.17 (C), 18.54 (CH$_3$). ESI Calcd for C$_{10}$H$_{16}$NO$_2$: 182.1 [M+H$^+$], found m/z 182.1 [M+H$^+$]. HRMS Calcd for C$_{10}$H$_{16}$NO$_2$: 182.1181 [M+H$^+$], found m/z 182.1183 [M+H$^+$].

Synthesis of Compound 4,5-bis((3,3,4,4,5,5,6,6,7,7,8,8,8-tridecafluorooctyl)thio)pentanoic acid (11) (CN37)

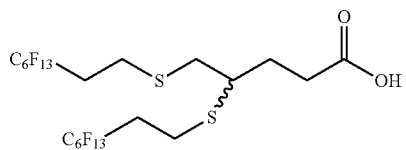

Pent-4-ynoic acid (500 mg, 55 mmol, 1 eq) and 1H, 1H, 2H, 2H perfluorooctanethiol (4.26 g, 110 mmol, 2.2 eq) are dissolved in 25 ml of dry THF. The middle is degassed under flowing argon for 30 minutes and then heated under reflux. After 5 min AIBN (210 mg, 13 mmol, 0.24 eq), is added. The reaction mixture is heated under reflux overnight. Then the solvent is removed in vacuo and the crude purified over silica gel (cyclohexane/EtOAc 9:1-8.5:2.5 as eluent) to afford 2.80 g of 11 as a white powder (yield=64%). TLC Rf=0.22 (Cyclohexane/Ethyl acetate 9/1).

$^1$H NMR (CDCl$_3$, 400 MHz) δ 2.92-2.70 (7H, m, CH, CH$_2$—S), 2.60 (2H, t, J=8.0 Hz CH$_2$—C=O), 2.45-2.32 (4H, m, CF$_2$—CH$_2$), 2.26-2.18 (1H, m, —CH$_2$—CH$_2$—C=O), 1.82-1.72 (1H, m, —CH$_2$—CH$_2$—C=O; $^{13}$C NMR (CDCl$_3$, 100 MHz) δ 178.37 (C=O), 45.62 (CH), 38.61 (CH$_2$—S), 32.21 (CF$_2$—CH$_2$), 30.98 (CH$_2$—C=O), 28.42 (—CH$_2$—CH$_2$—C=O), 23.67 (CH$_2$—S), 22.83 (CH$_2$—S); $^{19}$F NMR (CDCl$_3$, 100 MHz) −80.92 (3H, t, J=10.0 Hz), −114.38 (2H, q, J=15.0 Hz), −122.00 (2H, s), −122.97 (2H, s), −123.47 (2H, s), −126.25 (2H, m). ESI Calcd for C$_{21}$H$_{15}$F$_{26}$O$_2$S$_2$: 857.01 [M−H$^+$], found m/z 857.01 [M−H$^+$]. HRMS Calcd for C$_{21}$H$_{15}$F$_{26}$O$_2$S$_2$: 857.0098 [M−H$^+$], found m/z 857.0105 [M−H$^+$].

Synthesis of Compound N-(2-methyl-1,3-bis(prop-2-yn-1-yloxy)propan-2-yl)-4,5-bis((3,3,4,4,5,5,6,6,7,7,8,8,8-tridecafluorooctyl)thio)pentanamide 12 (SD115)

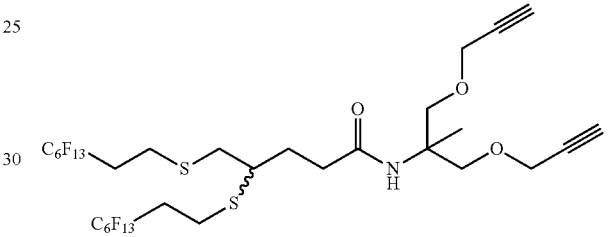

PyBOP (381 mg, 0.734 mmol, 1 eq), HOBt (99 mg, 0.734 mmol, 1 eq), compounds 11 (627 mg, 0.734, 1 eq) and 10 (133 mg, 0.734, 1 eq) are dissolved in a mixture of DCM (25 ml) and DMF (2 ml). After 5 min of stirring, DIEA is added (255 μl, 1.46 mmol, 2 eq). The reaction mixture is stirred overnight at room temperature. Then the solvent is removed under vacuum and the crude purified over silica gel (Cyclohexane/EtOAc 9:1-7.5:2.5 as eluent), to afford 378 mg of compound 12 as a colorless oil (yield=51%). TLC Rf=0.45 (Cyclohexane/Ethyl acetate 7/3).

$^1$H NMR (CDCl$_3$, 400 MHz) δ 5.75 (1H, s, NH), 4.16 (4H, m, CH$_2$-Alkyne), 3.72 (2H, t, J=9 Hz, CH$_2$—O), 3.61 (2H, t, J=9 Hz, CH$_2$—O), 2.91-2.85 (2H, m, CH, Ha CH$_2$—S) (2.81-2.75 (5H, m, Hb CH$_2$—S), 2.46-2.33 (8H, m, CH$_2$Alcyne, CF$_2$—CH$_2$, —CH$_2$—C=O), 2.25-2.16 (1Ha, m, —CH$_2$—CH$_2$—C=O) 1.78-1.69 (1Hb, m, —CH$_2$—CH$_2$—C=O), 1.39 (3H, s, CH$_3$); $^{13}$C NMR (CDCl$_3$, 100 MHz) δ 171.71 (C=O), 79.46 (C Alcyne), 74.59 (CH Alcyne), 72.03 (CH$_2$—O), 58.57 (CH$_2$—C), 56.37 (C), 45.89 (CH), 38.65 (CH$_2$—S), 33.90 (CH$_2$—C=O), 32.06 (t, J=22 Hz, CF$_2$—CH$_2$), 29.21 (—CH$_2$—CH$_2$—C=O), 23.70 (CH$_2$—S), 21.70 (CH$_2$—S) 18.54 (CH$_3$); $^{19}$F NMR (CDCl$_3$, 100 MHz) −80.92 (3H, t, J=10.0 Hz), −114.32 (2H, q, J=19.0 Hz), −121.99 (2H, s), −122.98 (2H, s), −123.44 (2H, m), −126.25 (2H, m) ESI Calcd for C$_{31}$H$_{30}$F$_{26}$NO$_3$S$_2$: 1022.13 [M+H$^+$], found m/z 1022.13 [M+H$^+$]; HRMS Calcd for C$_{31}$H$_{30}$F$_{26}$NO$_3$S$_2$: 1022.1252 [M+H$^{30}$], found m/z 1022.1244 [M+H$^+$].

4.2.2. Functionalization with Hydrophilic PolyTris Moieties

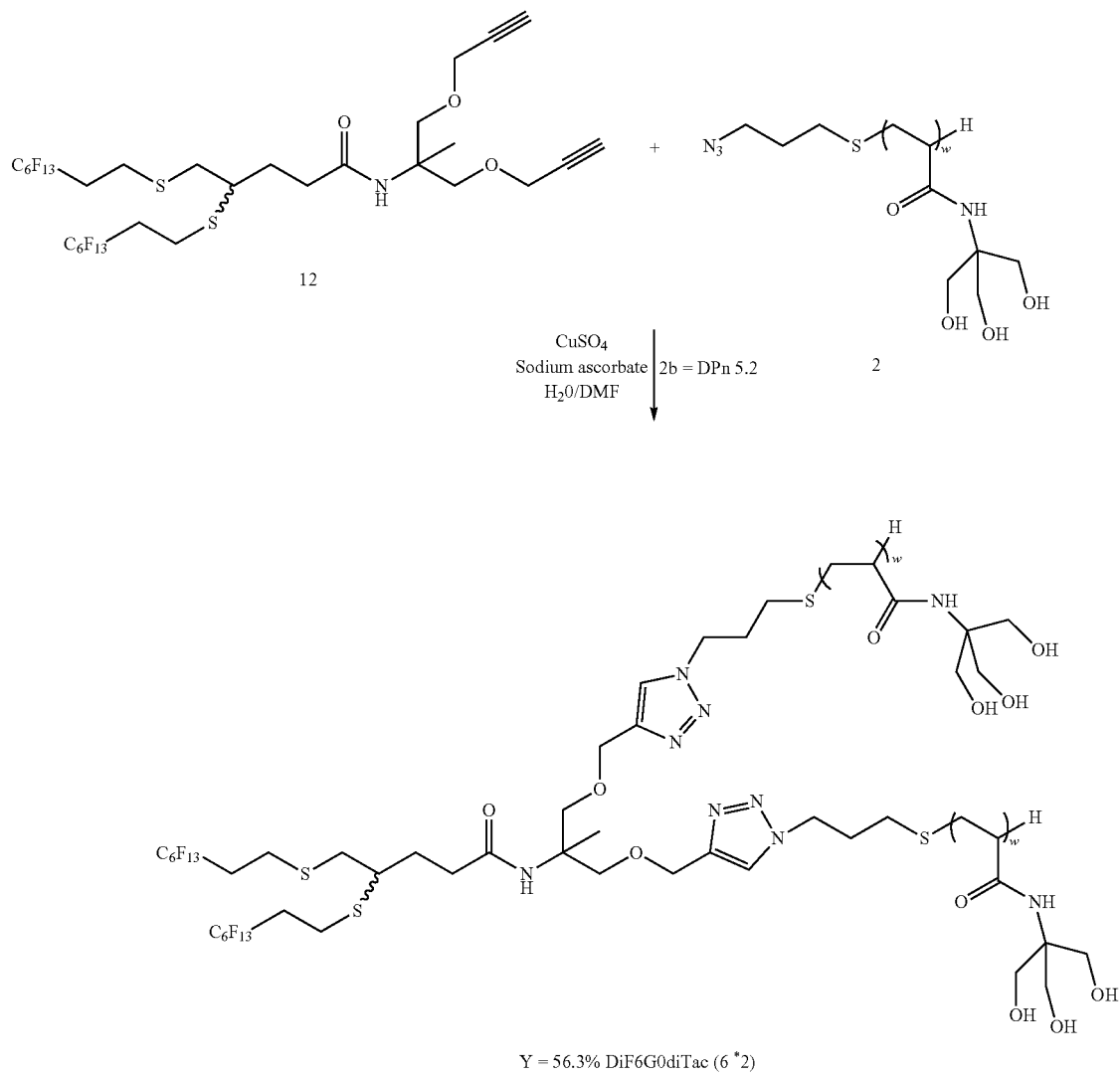

Y = 56.3% DiF6G0diTac (6 *2)

Synthesis of DiF6Tac5*2 (SD160)

Sodium ascorbate (57 mg, 0.288 mmol, 1.2 eq), compound 12 (250 mg, 0.24 mmol, 1 eq) and 2b (750 mg, 0.97 mmol, 4 eq) (DPn=5.2) are dissolved in a mixture of DMF (25 ml) and EtOH (25 ml), the reaction mixture is heated to 60° C., and after 5 minutes copper sulfate pentahydrate (24 mg, 0.096, 0.2 eq) is added. The solution is stirred at 60° C. during 3 hours and then at room temperature overnight. The solution is filtered and passed through chelex beads, and then the solvent is carefully removed under high vacuum. The crude is dissolved in a mixture of MeOH/water 9/1, filtered and then purified over LH20 MeOH/Water 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature without the water bath. The mixture is diluted with water, freeze dried and further purified by FSPE to obtain 150 mg of white compound with a DPn of 6 (yield=56.3%).

The DPn is assessed by 1H-NMR in DMSO, where the total integral of peaks at 4.40 ppm and 4.49 ppm is set for 8 Protons (Two $CH_2$ in α position of the triazole ring), and by dividing either the integral of the 6 CH2 protons of TRIS at 3.80 ppm by 12 or by dividing the integral of the OH protons, between 5.48 and 4.64 ppm, by 6.

$^1$H NMR (DMSO-d6, 400 MHz) δ (8.06 (2H, s, CH triazole), 7.75-6.85 (11H, c, NH), 5.48-4.64 (29H, c, OH), 4.49 (4H, s, $C_{TRIAZOLE}$—$CH_2$—O), 4.41 (4H, s, $CH_2$—$CH_2$—$N_{TRIAZOLE}$), 3.94-3.40 (104H, br, $CH_2$—OH, $CH_2$—O—), 2.98-2.86 (2H, m, CH, Ha $CH_2$—S), 2.85-2.70 (4H, c, $CF_2$—$CH_2$—$CH_2$—S, S—$CH_2$—$CH_2$—C=O), 2.59-1.84 (24H, c, $CF_2$—$CH_2$, —$CH_2$—C=O, $CH_2$—$CH_2$—$CH_2$—S, $CH_2$—C=O), 2.29-1.84 (29H, c, $CH_2$—$CH_2$—$CH_2$—S, $CH_2$—S, CH, $CH_2$—C=O, 1Ha —$CH_2$—$CH_2$—C=OCH—C=$O_{OLIGOMER}$), 1.80-1.28 (20H, c, 1 Hb —$CH_2$—$CH_2$—C=O $CH_2$ $_{OLIGOMER}$), 1.17 (3H, s, $CH_3$).

5. Amphiphilic Dendrimers Functionalized with polyTris Moieties-Generation 1 ($G_1$)

5.1. Monocatenar Amphiphilic Dendrimers with AB2 Building Blocks: F6G$_1$tetraTAC

5.1.1. Synthesis of the Monocatenar Scaffold, with Ester Junction, F6G$_1$ (AB2)

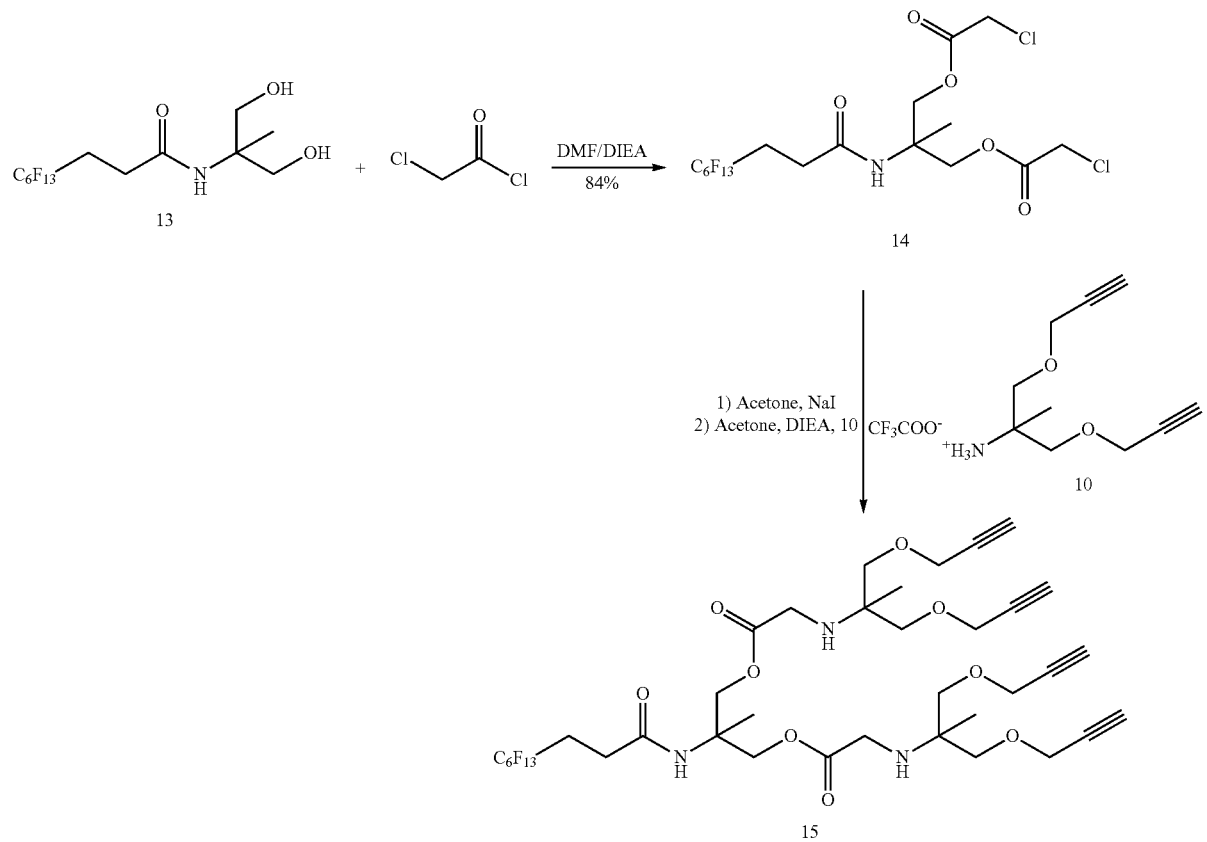

Synthesis of Compound N-(1,3-dihydroxy-2-methylpropan-2-yl)-4,4,5,5,6,6,7,7,8,8,9,9,9-tridecafluorononanamide 13 (SD216)

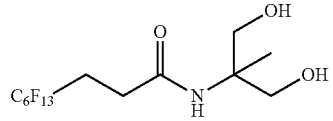

2-amino-2-methyl-1,3 propanediol (400 mg, 2.81 mmol, 1.5 eq), and 1H, 1H, 2H, 2H Perfluorononanoic acid (1 g, 2.55 mmol, 1 eq) are dissolved in 20 ml of EtOH, and then EEDQ (1.21 g, 5.1 mmol, 2 eq) is added. The reaction mixture is heated overnight at reflux. Then, the solvent is removed in vacuo and the crude is purified over silica gel (Cyclohexane/EtOAc 8.5:1.5-5:5 as eluent) to afford 800 mg of compound 13 as a white powder (yield=63%). TLC Rf=0.43 (Cyclohexane/Ethyl acetate 5/5).

$^1$H NMR (MeOD, 400 MHz) δ 3.67 (4H, dd, J=11.60, 26.64 Hz CH$_2$—O), 2.58-2.41 (4H, m, CH$_2$—CH$_2$CF$_2$—CH$_2$), 1.24 (3H, s, CH$_3$); $^{13}$C NMR (CDCl$_3$, 100 MHz) δ 173.12 (C=O), 65.73 (CH$_2$—O), 60.23 (C), 27.81 (t, 21.72 Hz CF$_2$—CH$_2$), 19.37 (CH$_3$); $^{19}$F NMR (CDCl$_3$, 100 MHz) −83.98 (3H, t, J=9.19 Hz), −117.23 (2H, m), −124.49 (2H, br), −125.49 (2H, br), −126.19 (2H, br), −128.91 (2H, m). ESI Calcd for C$_{13}$H$_{14}$F$_{13}$NO$_3$: 480.08 [M+H$^+$], found m/z 480.09 [M+H$^+$]; HRMS Calcd for C$_{13}$H$_{14}$F$_{13}$NO$_3$: 480.0844 [M+H$^+$], found m/z 480.0850 [M+H$^+$].

Synthesis of Compound 2-methyl-2-(4,4,5,5,6,6,7,7,8,8,9,9,9-tridecafluorononanamido)propane-1,3-diyl bis(2-chloroacetate) 14 (SD205)

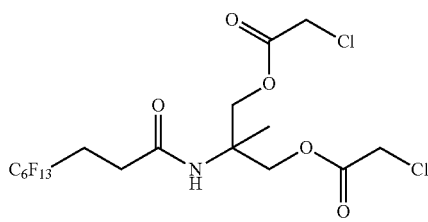

To a solution of compound 13 (412 mg, 0.86 mmol, 1 eq) in 5 ml of dry DMF, cooled to 0° C. under argon, were subsequently added DIEA (320 μl, 1.89 mmol, 2.2 eq) and chloroacetyl chloride (149 μl, 1.89 mmol, 2.2 eq). The reaction mixture is stirred overnight at room temperature. The solution is diluted with AcOEt (100 ml) and washed three times with water (3×50 ml) and dried over $Na_2SO_4$. The crude is purified over silica gel (Cyclohexane/EtOAc 9.5:0.5-7:3 as eluent) to afford 486 mg of compound 14 as a white powder (yield=84%). TLC Rf=0.27 (Cyclohexane/Ethyl acetate 7/3).

$^1$H NMR ($CDCl_3$, 400 MHz) δ 6.0 (1H, s, NH), 4.40 (4H, dd, J=11.26, 30.00 Hz $CH_2$—O), 4.07 (8H, s, $CH_2Cl$), 2.48-2.34 (4H, m, $CH_2$—$CH_2CF_2$—$CH_2$), 1.40 (3H, s, $CH_3$); $^{13}$C NMR ($CDCl_3$, 100 MHz) δ 170.19 (C=O amide), 167.14 (C=O ester), 66.82 ($CH_2$-O), 55.81 (C), 40.54 (—$CH_2$—Cl), 27.48 ($CH_2$—C=O), 26.44 (t, 21.72 Hz $CF_2$—$CH_2$), 19.20 ($CH_3$); $^{19}$F NMR ($CDCl_3$, 100 MHz) −80.91 (3H, t, J=10.0 Hz), −114.76 (2H, m), −122.09 (2H, s), −123.09 (2H, s), −123.73 (2H, m), −126.40 (2H, m). ESI Calcd for $C_{17}H_{16}Cl_2F_{13}NO_5$: 632.02 [M+H$^+$], found m/z 632.03 [M+H$^+$]; HRMS Calcd for $C_{17}H_{16}Cl_2F_{13}NO_5$: 632.0276 [M+H$^+$], found m/z 632.0278 [M+H$^+$].

Synthesis of Compound 2-methyl-2-(4,4,5,5,6,6,7,7,8,8,9,9,9-tridecafluorononanamido)propane-1,3-diyl bis(2-((2-methyl-1,3-bis(prop-2-yn-1-yloxy)propan-2-yl)amino)acetate)15 (SD206)

Compound 14 (200 mg, 0.316 mmol, 1 eq) is dissolved in 3 ml of acetone and then NaI (94 mg, 0.63 mmol, 3 eq) is added. The reaction mixture is stirred for one hour and the solution is filtered through sintered glass filter. The filtrate is concentrated, and a solution of 10 (205 mg, 0.695 mmol, 2.2 eq) in 2 ml of acetone is added along with DIEA (245 μl, 1.90 mmol, 4.4 eq). The reaction mixture is stirred during 48 hours. Then the solvent is evaporated and the crude is dissolved in EtOAc (50 ml), and the solution is filtered (to get rid of DIEA salt) and washed 3 times with a solution of 0.1N HCl and $NaHCO_3$ saturated. The crude is purified over silica gel (Cyclohexane/EtOAc 5:5-0:10 as eluent), to afford 200 mg of yellowish oil (yield=69%) (Note: wash not necessary). TLC Rf=0.65 (Ethyl acetate).

$^1$H NMR ($CDCl_3$, 400 MHz) δ 6.06 (1H, s, NH amide), 4.27 (4H, d, J=11.26, 35.75 Hz $CH_2$—O), 4.09 (8H, d, J=2.45 Hz $CH_2$Alcyne), 3.46 (4H, s, —$CH_2$—NH), 3.38 (8H, dd, J=9.35, 14.00 Hz —$CH_2$—O), 2.53-2.33 (8H, m, $CH_2$—$CH_2CF_2$—$CH_2$H-Alcyne), 2.23 (2H, br, NH amine), 1.38 (3H, s, $CH_3$), 1.04 (6H, m, s, $CH_3$); $^{13}$C NMR ($CDCl_3$, 100 MHz) δ 172.59 (C=O ester), 169.79 (C=O amide), 79.46 (C Alcyne), 79.60 (C alcyne) 74.50 (CH alcyne), 73.32 ($CH_2$—O), 65.98 ($CH_2$—O), 58.46 ($CH_2$—Calcyne), 55.61 (C), 44.39 (—$CH_2$—NH), 27.48 ($CH_2$—C=O), 26.43 (t, 21.72 Hz $CF_2$—$CH_2$), 19.29 ($CH_3$), 18.92 (—$CH_3$); $^{19}$F NMR ($CDCl_3$, 100 MHz) −80.91 (3H, t, J=10.0 Hz), −114.59 (2H, m), −121.97 (2H, s), −122.97 (2H, s), −123.65 (2H, m), −126.26 (2H, m). ESI Calcd for $C_{37}H_{44}F_{13}N_3O_9$: 922.29 [M+H$^+$], found m/z 922.30 [M+H$^+$]; HRMS Calcd for $C_{37}H_{44}F_{13}N_3O_9$: 922.2948 [M+H$^+$], found m/z 922.2946 [M+H$^+$].

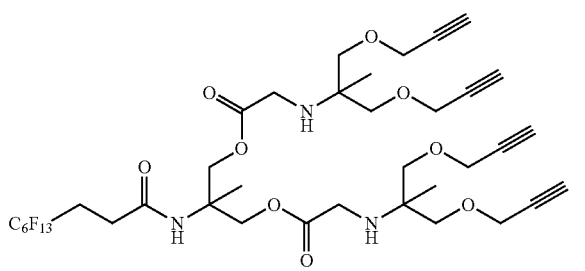

15

5.1.2. Functionalization with Hydrophilic PolyTris Moieties

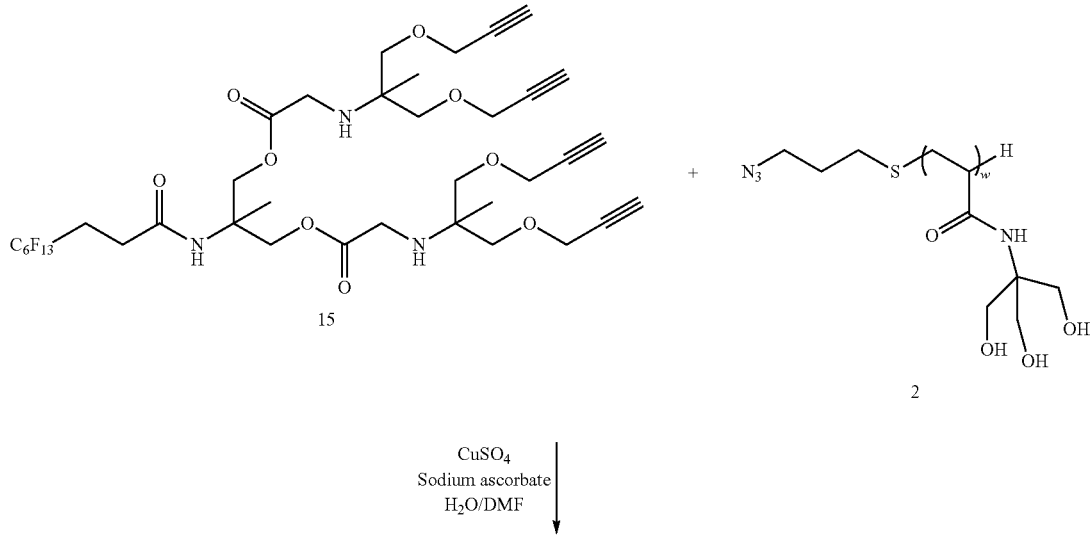

CuSO$_4$
Sodium ascorbate
H$_2$O/DMF

-continued

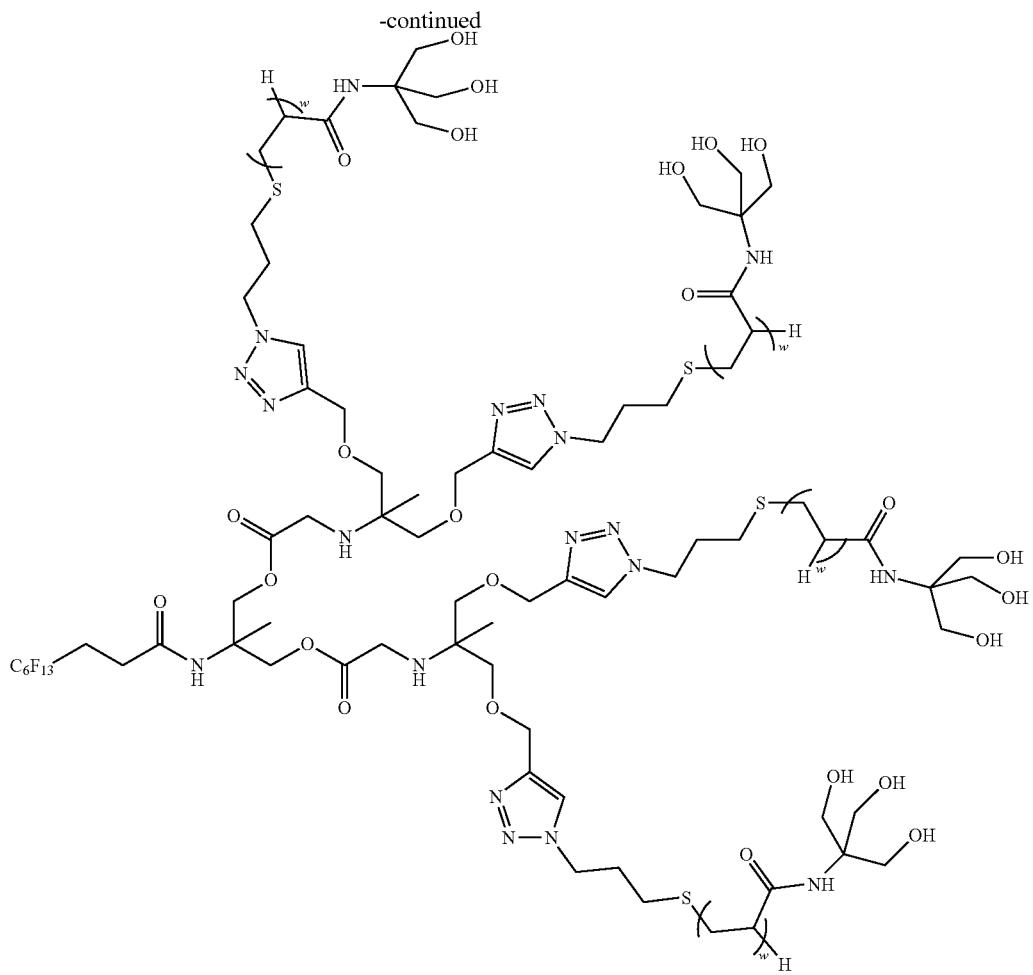

Sodium ascorbate (62.37 mg, 0.315 mmol, 1.2 eq), compound 15 (200 mg, 0.21 mmol, 1 eq) and compound 2b (1125 mg, 1.06 mmol, 5 eq) (DPn=5.2) are dissolved in a mixture of DMF (15 ml) and Water (8 ml), the mixture is heated at 50° C., and after 5 minutes copper sulfate pentahydrate (31.5 mg, 0.096 mmol, 0.2 eq) is added. The solution is heated at 50° C. during 3 hours, and then stirred at room temperature overnight. The solution is filtered and passed through chelex beads, and then the solvent is carefully removed in vacuo. The crude is dissolved in a mixture of MeOH/water 9/1, filtered and purified over LH20 MeOH/Water 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature without the water bath. The mixture is diluted with water, freeze dried and further purified by FSPE to recover 335 mg of desired compound as a white powder with a DPn of 6 (yield=30.5%).

The DPn is assessed by 1H-NMR in DMSO, where the integral of peaks at 4.40 ppm and 4.49 is set for 16 Protons (Two $CH_2$ in α position of the triazole ring), and by dividing the integral of the $CH_2$ protons of TRIS at 3.80 ppm by six or dividing the integral of the OH protons, between 5.38 and 4.61 ppm, by three.

$^1$H NMR (DMSO-d6, 400 MHz) δ (8.10 (4H, s, CH triazole), 7.66-6.85 (32H, c, NH), 5.38-4.61 (92H, c, OH), 4.51 (8H, s, $C_{TRIAZOLE}$—$CH_2$—O), 4.41 (8H, s, $CH_2$—$CH_2$—$N_{TRIAZOLE}$), 3.80-3.46 (192H, br, $CH_2$—OH, $CH_2$—O—), 2.69-2.36 (12H, c, $CF_2$—$CH_2$—$CH_2$—S, S—$CH_2$—$CH_2$—C=O, $CF_2$—$CH_2$, $CH_2$—$CH_2$—$CH_2$—$CH_2$—C=O), 2.32-1.89 (57H, c, $CH_2$—$CH_2$—$CH_2$—S, $CH_2$—S, CH, $CH_2$—C=O, CH—C=$O_{OLIGOMER}$), 1.80-0.88 (122H, m, $CH_{2OLIGOMER}$, $CH_3$). $^{19}$F NMR (CDCl$_3$, 100 MHz) −80.91 (3H, m), −113.55 (2H, m), −121.72 (2H, br), −122.66 (2H, br), −123.18 (2H, br), −125.78 (2H, br).

5.1.3. Synthesis of the Monocatenar Scaffold, with Amide Junction, (Mickaël Addition) F6G$_1$ (AB2)
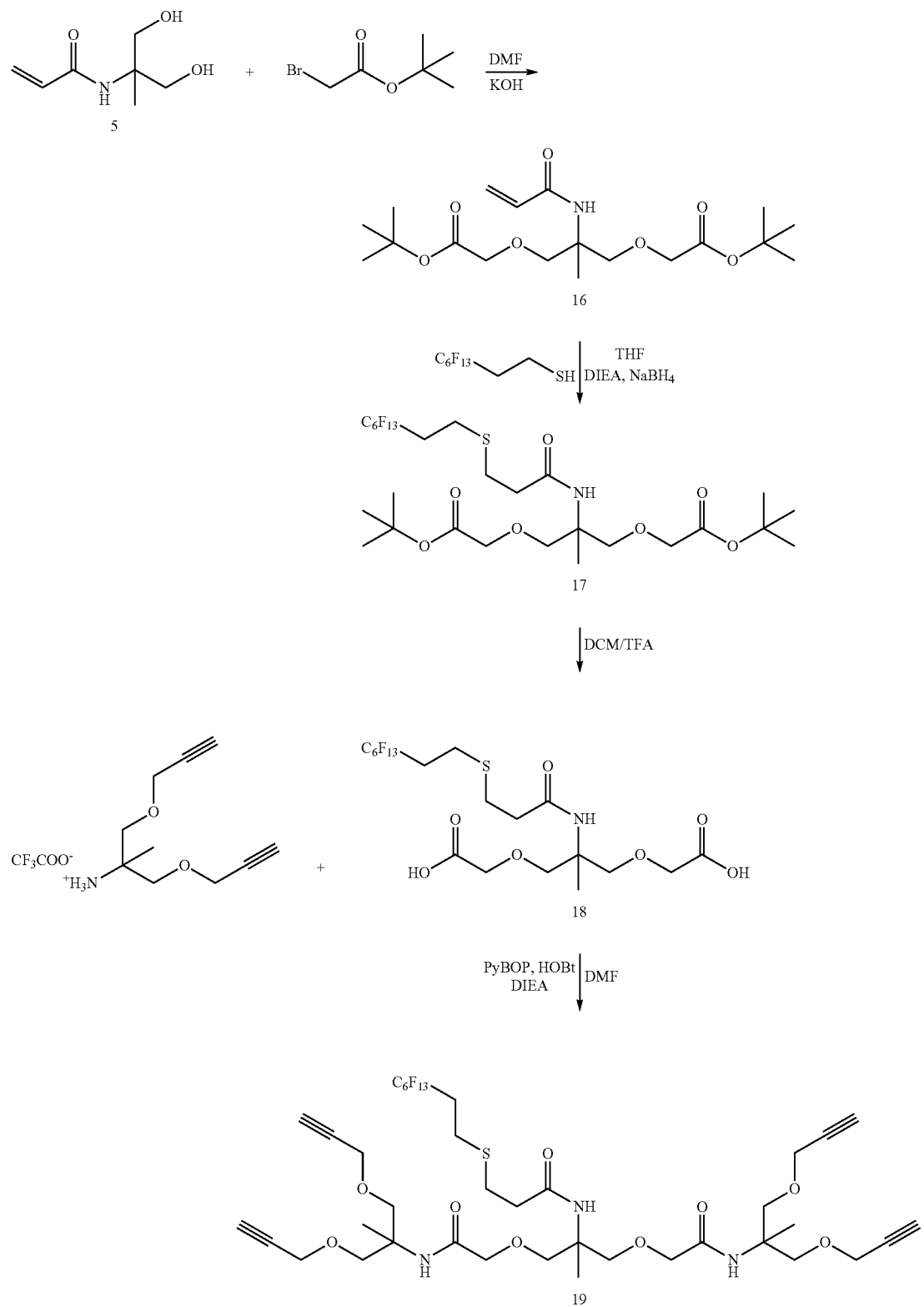

Synthesis of Compound 16 (SD385)

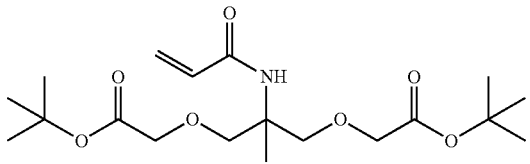 [SMILES: C=CC(=O)NC(C)(COCC(=O)OC(C)(C)C)COCC(=O)OC(C)(C)C]

Compound 5 (4 g, 25 mmol, 1 eq), tert-butyl 2-bromo-acetate (10.23 g, 52.5 mmol, 2.1 eq) are dissolved in DMF. The resulting mixture is cooled down to 0° C., then fine grinded KOH (2.94, 52.5 mmol, 2.1 eq) is slowly added by portion during two hours. The mixture is left to warm to room temperature and stirred during 16 hours. The solution is filtered and the solvent is removed under high vacuum. The crude is purified over $SiO_2$ (Cyclohexane/EtOAc 2:8-5.5:4.5 as eluent) to afford 800 mg of 16 as a colorless oil (yield=8.2%). TLC Rf=0.75 (Cyclohexane/EtOAc 5:5).

$^1$H NMR (CDCl$_3$, 400 MHz) δ 7.49 (1H, s, NH), 6.13 (1H, dd, J=2.7, 17.2 Hz, Ha CH$_2$=CH), 6.07 (1H, dd, J=9.4, 17.2 Hz, Ha CH$_2$=CH), 5.45 (1H, dd, J=2.7, 9.4 Hz), 3.85 (4H, dd, J=17.0, 18.6 Hz, CH$_2$—C=O), 3.68 (2H, d, J=9.16 Hz, CH$_2$—O), 3.54 (2H, d, J=9.16 Hz, CH$_2$—O), 1.35 (18H, s, tBu), 1.33 (3H, s, CH$_3$); $^{13}$C NMR (CDCl$_3$, 100 MHz) δ 170.37 (C=O ester), 165.35 (C=O amide), 132.15 (CH$_2$=CH), 125.02 (CH$_2$=CH), 81.79 (C), 73.72 (CH$_2$—O), 68.48 (CH$_2$—C=O), 56.44 (C), 28.00 (tBu), 17.99 (CH$_3$).

Synthesis of Compound 17 (SD396)

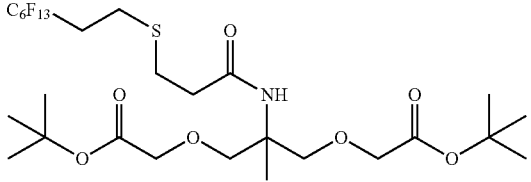

To a cold solution of compound 16 (216 mg, 0.56 mmol, 1 eq) and 1H, 1H, 2H, 2H perfluorooctanethiol (318 mg, 0.84 mmol, 1.5 eq) in 5 ml of THF, is added DIEA (10 μl, 0.056 mol, 0.1 eq) and NaBH$_4$ (22 mg, 0.61 mmol, 1.1 eq). The resulting mixture is stirred overnight, then the solution is filtered and purified over $SiO_2$ (Cyclohexane/EtOAc 9:1-7:3 as eluent) to afford 216 mg of 17 as colorless oil (yield=50.4%). TLC Rf=0.49 (Cyclohexane/EtOAc 7:3).

$^1$H NMR (CDCl$_3$, 400 MHz) δ 7.49 (1H, s, NH), 3.94 (4H, dd, J=16.8, 18.8 Hz, CH$_2$—C=O), 3.72 (2H, d, J=9.10 Hz, CH$_2$—O), 3.59 (2H, d, J=9.10 Hz, CH$_2$—O), 2.83 (2H, t, J=7.4 Hz, S—CH$_2$ $_{AMIDE}$), 2.73 (2H, m, S—CH$_{2FLUOR}$), 2.48 (2H, t, J=7.4 Hz, S—CH$_2$—CH$_2$ $_{AMIDE}$), 2.36 (2H, m, S—CH$_2$—CH$_2$—CF$_2$), 1.43 (18H, s, tBu), 1.38 (3H, s, CH$_3$); $^{13}$C NMR (CDCl$_3$, 100 MHz) δ 170.91 (C=O amide), 170.67 (C=O ester), 82.16 (CtBu), 74.03 (CH$_2$—O), 68.76 (CH$_2$—C=O), 56.73 (C), 37.24 (S—CH$_2$—CH$_{2AMIDE}$), 32.20 (t, J=20.0 Hz, CH$_2$—CF$_2$), 28.00 (tBu), 27.88 (S—CH$_2$ $_{AMIDE}$), 22.73 (S—CH$_{2FLUOR}$), 18.30 (CH$_3$). $^{19}$F NMR (CDCl$_3$, 100 MHz) −80.81 (3H, t, J=10.26 Hz), −114.35 (2H, m), −121.95 (2H, br), −122.90 (2H, br), −123.40 (2H, br) −126.17 (2H, m).

Synthesis of Compound 18 (SD388)

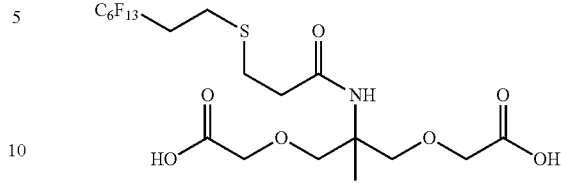

Compound 17 is dissolved in 4 ml of DCM, and then 100 l of water are added followed by 4 ml of TFA. The resulting mixture is stirred for 2 hours without tap. Then the solvent is removed under high vacuum in order to afford pure compound 18 in quantitative yield as colorless oil.

$^1$H NMR (CDCl$_3$, 400 MHz) δ 7.77 (1H, s, NH), 4.13 (4H, dd, J=17.16, 19.84 Hz, CH$_2$—C=O), 3.78 (2H, d, J=9.61 Hz, CH$_2$—O), 3.65 (2H, d, J=9.61 Hz, CH$_2$—O), 2.82 (2H, t, J=7.1 Hz, S—CH$_2$ $_{AMIDE}$), 2.73 (2H, m, S—CH$_{2FLUOR}$), 2.55 (2H, t, J=7.1 Hz, S—CH$_2$—CH$_2$ $_{AMIDE}$), 2.36 (2H, m, S—CH$_2$—CH$_2$—CF$_2$), 1.36 (3H, s, CH$_3$); $^{13}$C NMR (CDCl$_3$, 100 MHz) δ 174.37 (C=O ester), 172.96 (C=O amide), 74.53 (CH$_2$—O), 68.04 (CH$_2$—C=O), 57.03 (C), 37.06 (S—CH$_2$—CH$_2$ $_{AMIDE}$), 32.03 (t, J=24.0 Hz, CH$_2$—CF$_2$), 27.93 (S—CH$_2$ $_{AMIDE}$), 22.79 (S—CH$_{2FLUOR}$), 18.50 (CH$_3$) $^{19}$F NMR (CDCl$_3$, 100 MHz) −80.81 (3H, t, J=10.03 Hz), −114.38 (2H, m,), −121.95 (2H, br), −122.91 (2H, br), −123.44 (2H, br) −126.18 (2H, m).

Synthesis of Compound 19 (SD389)

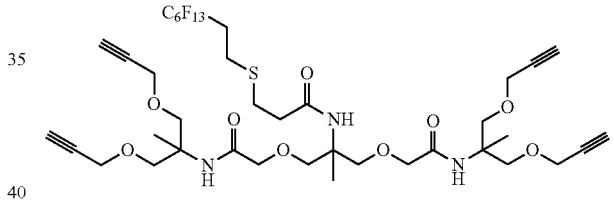

Compounds 18 (103 mg, 0.162 mmol, 1 eq), PyBOP (185 mg, 0.356 mmol, 2.2 eq), HOBt (48 mg, 0.356 mmol, 2.2 eq), and DIEA (112 μl, 0.64 mmol, 4 eq) are dissolved in 6 ml of DMF, after 5 min compound 10 (105 mg, 0.356 mmol, 2.2 eq) was added. As the pH was not basic, then another 4 eq of DIEA is added to obtain a basic pH. The resulting mixture is stirred overnight and then diluted with 50 ml of AcOEt, washed three times with HCl 0.2 N, once with water, dried over Na$_2$SO$_4$ and purified over $SiO_2$ (combiflash from 6:4 to 3:7 cyclohexane:ethyl acetate) to afford 115 mg of 19 as colorless oil (yield=72.3%). TLC Rf=0.39 (Cyclohexane/EtOAc 7:3).

$^1$H NMR (CDCl$_3$, 400 MHz) δ 6.62 (2H, s, NH), 6.46 (1H, s, NH), 4.16 (8H, d, J=2.45 Hz, CH$_2$—O alkyne) 3.90 (4H, dd, J=15.1, 16.7 Hz, CH$_2$—C=O), 3.76-3.72 (6H, m, CH$_2$—O), 3.63-3.61 (6H, m, CH$_2$—O), 2.84 (2H, t, J=7.2 Hz, S—CH$_2$ $_{AMIDE}$), 2.77 (2H, m, S—CH$_{2FLUOR}$), 2.50 (2H, t, J=7.2 Hz, S—CH$_2$—CH$_2$ $_{AMIDE}$), 2.47 (4H, t, J=2.45 Hz, CH), 1.43 (2H, m, S—CH$_2$—CH$_2$—CF$_2$), 1.36 (3H, s, CH$_3$); $^{13}$C NMR (CDCl$_3$, 100 MHz) δ 170.99 (C=O amide), 169.22 (2×C=O amide), 79.65 (C alkyne), 74.95 (CH alkyne), 73.84 (2×CH$_2$—O), 72.17 (4×CH$_2$—O), 71.11 (CH$_2$—C=O), 58.75 (CH$_2$—O alkyne), 56.81 (C), 56.26 (C), 37.15 (S—CH$_2$—CH$_2$ $_{AMIDE}$), 32.14 (t, J=24.0 Hz, CH$_2$—CF$_2$), 27.75 (S—CH$_2$ $_{AMIDE}$), 23.06 (S—CH$_2$ $_{FLUOR}$), 19. $^{19}$F NMR (CDCl$_3$, 100 MHz) −80.75 (3H, t, J=10.03 Hz), −114.29 (2H, m,), −121.88 (2H, br), −122.86 (2H, br), −123.36 (2H, br) −126.12 (2H, m) 34 (CH$_3$).

5.1.4. Functionalization with Hydrophilic PolyTris Moieties
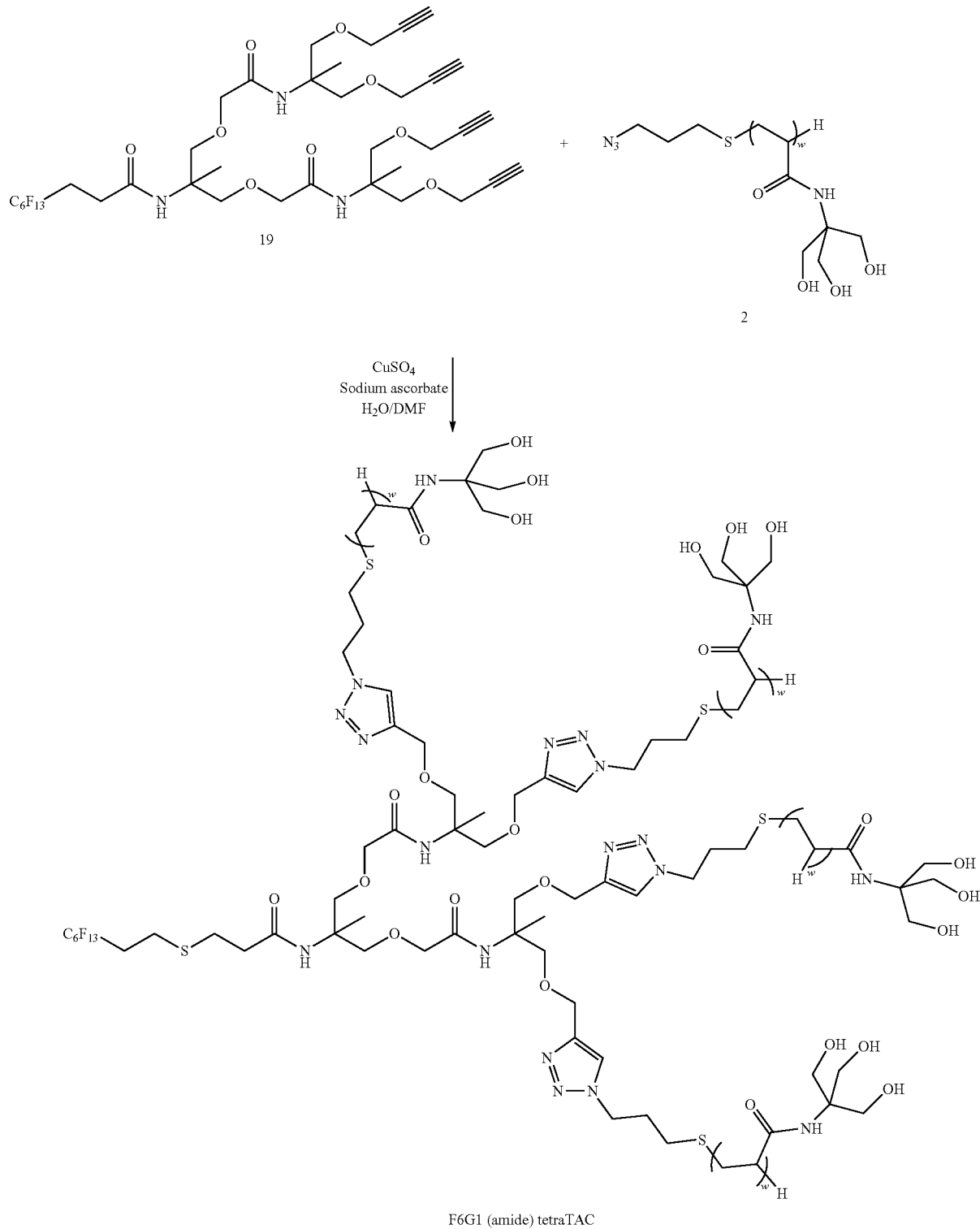
F6G1 (amide) tetraTAC
Sodium ascorbate (43.6 mg, 0.22 mmol, 2 eq), compound 19 (110 mg, 0.11 mmol, 1 eq) and compound 2b (565 mg, 0.54 mmol, 4.8 eq) (DPn~5.4) are dissolved in a mixture of DMF (4 ml) and water (3 ml), the mixture is heated at 55° C., and after 5 minutes copper sulfate pentahydrate (11.0 mg, 0.044 mmol, 0.4 eq) is added. The solution is heated at 55° C. overnight. The solution is passed through chelex beads, and then the solvent is carefully removed in vacuo. The product is purified by fluorous solid-phase extraction (FSPE). Briefly, the column is equilibrated with 25 ml of a mixture of water and DMF (9/1), then between 100 mg and 400 mg of product are dissolved in 1 ml of this mixture and deposit onto the column, after 25 ml of this eluent is pass through the column to get rid of non-fluorous compounds, then 25 ml of water, followed by 25 ml of a mixture of MeOH and Water (9/1) and finally 12 ml of pure methanol in order to rinse the column. Eluents containing methanol are concentrated in vacuo, diluted with water and freeze-dried. The compound is dissolved in minimum amount of methanol and precipitated in Et$_2$O, dissolved in water and freeze-dried to afford 430 mg of white compound with a DPn of 6 (yield=72.8%).

$^1$H NMR (DMSO-d6, 400 MHz) δ 8.06 (4H, s, CH triazole), 7.67-6.82 (26H, c, NH), 5.34-4.58 (73H, c, OH), 4.50 (8H, s, C$_{TRIAZOLE}$—CH$_2$—O), 4.40 (8H, s, CH$_2$—CH$_2$—N$_{TRIAZOLE}$), 3.80-3.42 (162H, br, CH$_2$—OH, CH$_2$—O—), 2.45-2.36 (12H, c, CF$_2$—CH$_2$—CH$_2$—S, S—CH$_2$—CH$_2$—C=O, CF$_2$—CH$_2$, CH$_2$—CH$_2$—CH$_2$—C=O), 2.32-1.89 (45H, c, CH$_2$—CH$_2$—CH$_2$—S, CH$_2$—S, CH, CH$_2$—C=O, CH—C=O$_{OLIGOMER}$), 1.76-1.17 (54H, m, CH$_{2 OLIGOMER}$, CH$_3$). 175.56, 168.96, 162.30 (C=O), 143.75 (C-triazole), 123.82 (CH-triazole), 72.90 (2×CH$_2$—O), 71.55 (4×CH$_2$—O), 70.22 (CH$_2$—C=O), 69.77 (CH$_2$—C=O), 64.00 (C$_{TRIAZOLE}$—CH$_2$—O), 62.49 (C), 60.53 (CH$_2$—OH), 55.99 (C), 48.17 (CH$_2$—Ntriazole), 42.18 (C-oligomer), 35.77 (CH$_2$—C=O), 30.77 (CH$_2$—CF$_2$), 29.69 (CH$_2$—CF$_2$), 29.44 (CH$_2$—CH$_2$—CH$_2$—S), 26.97 (CF$_2$—CH$_2$—CH$_2$—S), 21.73 (S—CH$_2$—CH$_2$—C=O), 19.00 (CH$_3$); $^{19}$F NMR (CDCl$_3$, 100 MHz) −80.19 (3H, m), −113.22 (2H, m), −121.72 (2H, br), −122.64 (2H, br), −122.86 (2H, br), −125.73 (2H, br).

5.2. Bicatenar Amphiphilic Dendrimers with AB2 Building Blocks: diF6G$_1$tetraTAC

5.2.1. Synthesis of the Bicatenar Scaffold diF6G$_1$ (AB2)

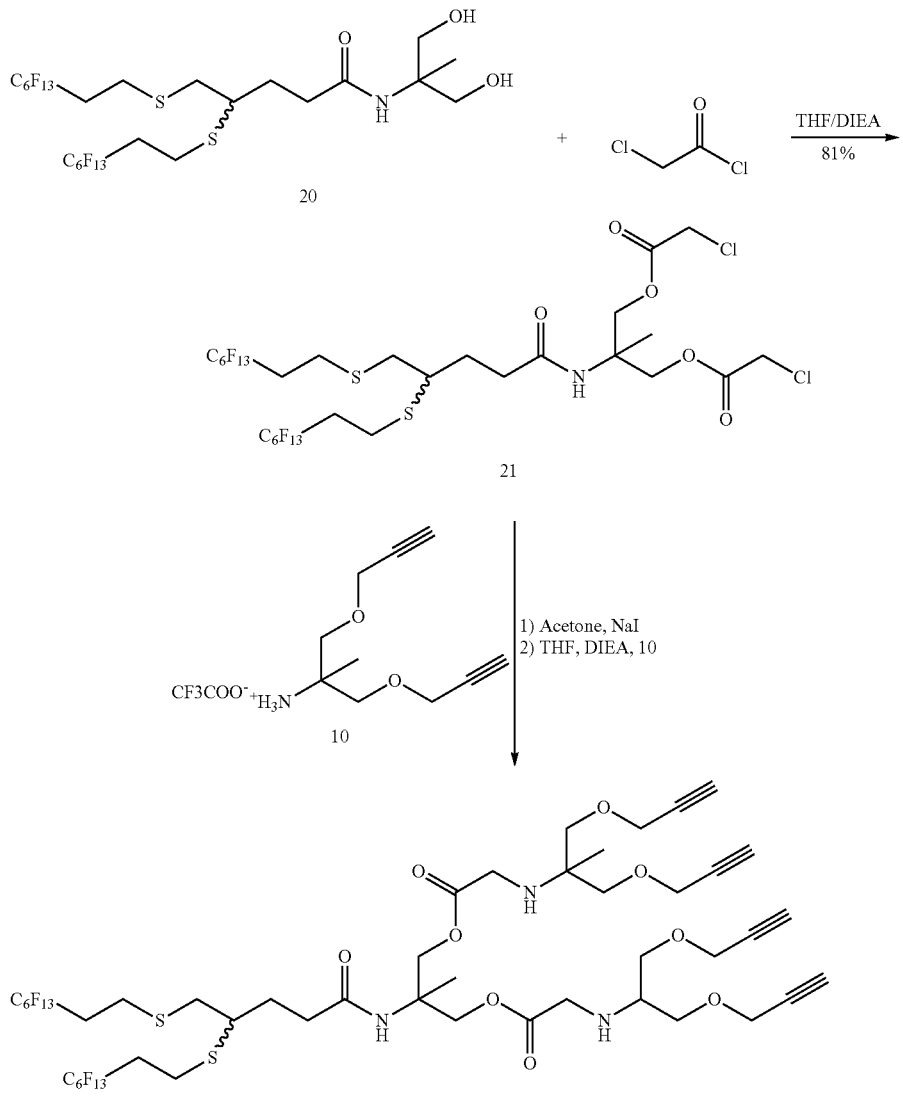

Synthesis of Compound N-(1,3-dihydroxy-2-methylpropan-2-yl)-4,5-bis((3,3,4,4,5,5,6,6,7,7,8,8,8-tridecafluorooctyl)thio)pentanamide (20) (SD207)

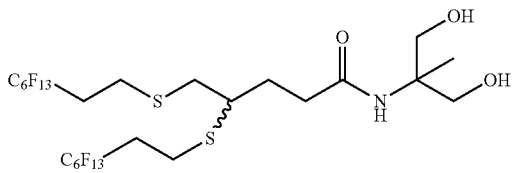

2-amino-2-methyl-1,3pronadiol (201 mg, 1.92 mmol, 1.5 eq), and compound 11 (1.1 g, 1.28 mmol, 1 eq) are dissolved in 35 ml of EtOH, and then EEDQ (632 mg, 2.56 mmol, 2 eq) is added. The reaction mixture is heated overnight at reflux. Then, the solvent is evaporated and the crude is purified over silica gel (Cyclohexane/EtOAc 6.5:3.5-1.5:8.5 as eluent) to afford 1.02 g of 20 as a white powder, (yield=83%). TLC Rf=0.58 (Cyclohexane/Ethyl acetate 7/3).

$^1$H NMR (CDCl$_3$, 400 MHz) δ 5.90 (1H, NH), 3.83-3.73 (2H, m, CH$_2$—O), 3.69-3.62 (2H, m, CH$_2$—O), 3.58-3.48 (2H, m, OH), 2.93-2.84 (2H, m, CH, Ha CH—CH$_2$—S), 2.82-2.71 (5H, m, Hb CH—CH$_2$—SCH$_2$—S), 2.48-2.34 (4H, m, CF$_2$—CH$_2$), 2.29-2.22 (1H, m, —CH$_2$—CH$_2$—C=O), 1.83-1.72 (1H, m, —CH$_2$—CH$_2$—C=O), 1.22 (3H, s, CH$_3$); $^{13}$C NMR (CDCl$_3$, 100 MHz) δ 173.31 (C=O), 67.89 (CH$_2$—O), 59.10 (C), 45.71 (CH), 38.68 (CH$_2$—S), 33.97 (CH$_2$—C=O), 31.94 (t, J=23.45 Hz, CF$_2$—CH$_2$), 29.24 (—CH$_2$—CH$_2$—C=O), 23.69 (CH$_2$—S), 21.76 (CH$_2$—S), 20.46 (CH$_3$); $^{19}$F NMR (CDCl$_3$, 100 MHz) -80.79 (3H, t, J=10.16 Hz), -114.28 (2H, q, J=15.49 Hz), -121.94 (2H, br), -122.92 (2H, br), -123.39 (2H, br), -126.19 (2H, m). ESI Calcd for C$_{25}$H$_{25}$F$_{26}$NO$_3$S$_2$: 946.09 [M+H$^+$], found m/z 946.09 [M+H$^+$]. HRMS Calcd for C$_{21}$H$_{15}$F$_{26}$O$_2$S$_2$: 946.0939 [M+H$^+$], found m/z 946.0931 [M+H$^+$].

Synthesis of Compound 2-(4,5-bis((3,3,4,4,5,5,6,6,7,7,8,8,8-tridecafluorooctyl)thio)pentanamido)-2-methylpropane-1,3-diyl bis(2-chloroacetate) (21) (SD222)

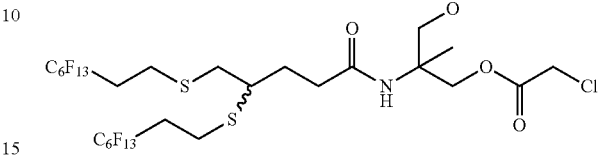

To a solution of 20 (600 mg, 0.635 mmol, 1 eq) and DIEA (243 µl, 1.40 mmol, 2.2 eq) in dry and distilled THF (15 ml), cooled to 0° C. under argon, was slowly added chloroacetyl chloride (107 µl, 1.40 mmol, 2.2 eq). The reaction mixture is stirred for 4 hours at room temperature. Then, the solvent is removed in vacuo, and the crude is purified over silica gel (Cyclohexane/EtOAc 8:2-6:4 as eluent), and a second purification over LH20 in MeOH is carried out, to give 630 mg of 21 as colorless oil (yield=81%). TLC Rf=0.44 (Cyclohexane/Ethyl acetate 7/3).

$^1$H NMR (CDCl$_3$, 400 MHz) δ 5.76 (1H, s, NH), 4.41 (4H, ddd, J=2.27, 11.07, 32.15 Hz CH$_2$—O), 4.09 (4H, s, CH$_2$Cl), 2.89-2.69 (7H, m, CH, CH$_2$—S), 2.45-2.30 (6H, m, CF$_2$—CH$_2$, CH$_2$—C=O), 2.22-2.13 (1H, m, —CH$_2$—CH$_2$—C=O), 1.77-1.68 (1H, m, —CH$_2$—CH$_2$—C=O), 1.42 (3H, s, CH$_3$); $^{13}$C NMR (CDCl$_3$, 100 MHz) δ 172.53, (C=O amide) 167.22, 167.21 (C=O ester), 67.12, 67.06 (CH$_2$—O), 55.97 (C), 45.67 (CH), 40.74 (—CH$_2$—Cl), 38.50 (CH$_2$—S), 33.85 (CH$_2$—C=O), 32.10 (tdd, 4.33, 22.29 Hz, CF$_2$—CH$_2$), 28.98 (—CH$_2$—CH$_2$—C=O), 23.66 (CH$_2$—S), 21.42 (CH$_2$—S) 19.42 (CH$_3$); $^{19}$F NMR (CDCl$_3$, 100 MHz) -81.03 (3H, t, J=10.03 Hz), -114.44 (2H, septuplet, J=15.04 Hz), -122.08 (2H, s), -123.07 (2H, s), -123.53 (2H, s), -126.36 (2H, m). ESI Calcd for C$_{29}$H$_{27}$Cl$_2$F$_{26}$NO$_5$S$_2$: 1098.04 [M+H$^+$], found m/z 1098.03 [M+H$^+$]. HRMS Calcd for C$_{29}$H$_{27}$Cl$_2$F$_{26}$NO$_5$S$_2$: 1098.0371 [M+H$^+$], found m/z 1098.0371 [M+H$^+$].

Synthesis of Compound 2-(4,5-bis((3,3,4,4,5,5,6,6,7,7,8,8,8-tridecafluorooctyl)thio)pentanamido)-2-methylpropane-1,3-diyl bis(2-((2-methyl-1,3-bis(prop-2-yn-1-yloxy)propan-2-yl)amino)acetate) (22) (SD224)

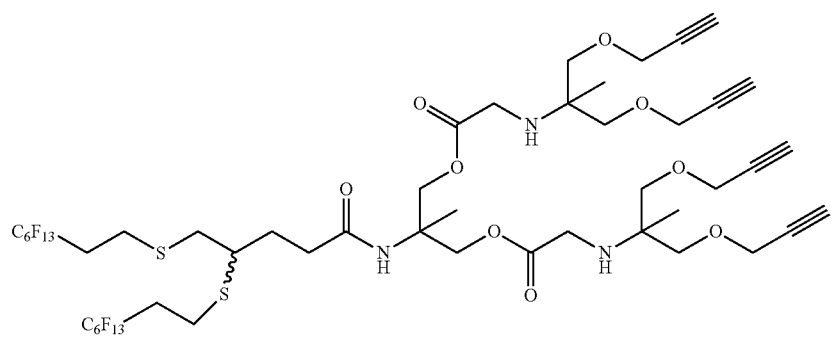

Compound 21 (290 mg, 0.26 mmol, 1 eq) is dissolved in 3 ml of acetone and then NaI (78 mg, 0.53 mmol, 2 eq) is added. The reaction mixture is stirred for 2 hours and the solution is filtered through sintered glass filter. The filtrate is evaporated and dissolved in 15 ml of dry THF, then compound 10 (105 mg, 0.58 mmol, 2.2 eq) is added along with DIEA (107 µl, 0.58 mmol, 2.2 eq). The reaction mixture is stirred overnight. Then the solvent is removed in vacuo and the crude is dissolved in EtOAc (50 ml), filtered (to get rid of DIEA salt) and washed 3 times with a solution of 0.1N HCl and NaHCO$_3$ saturated. The crude is purified over silica gel (Cyclohexane/EtOAc 7:3-3:7 as eluent) to afford 160 mg of 22 as a white powder (yield=42%). TLC Rf=0.58 (Cyclohexane/Ethyl acetate 3/7).

$^1$H NMR (CDCl$_3$, 400 MHz) δ 5.87 (1H, s, NH), 4.29 (4H, ddd, J=3.85, 11.33, 36.83 Hz CH$_2$—O), 4.12 (8H, d, J=2.35 Hz CH$_2$Alcyne), 3.48 (4H, s, —CH$_2$—NH), 3.40 (8H, dd, J=9.33, 14.03 Hz —CH$_2$—O), 2.87-2.72 (7H, m, CH, CH$_2$—S), 2.44-2.30 (10H, m, CF$_2$—CH$_2$, CH$_2$—C=O, H-Alcyne), 2.22-2.10 (1H, m, —CH$_2$—CH$_2$—C=O), 1.76-1.68 (1H, m, —CH$_2$—CH$_2$—C=O), 1.39 (3H, s, CH$_3$), 1.05 (6H, m, s, CH$_3$); $^{13}$C NMR (CDCl$_3$, 100 MHz) δ 172.76, 172.72 (C=O ester), 171.99 (C=O amide), 79.78 (C Alcyne), 74.60 (C alcyne), 73.50 (CH$_2$—O) 66.22, 66.11 (CH$_2$—O), 58.63 (CH$_2$—Calcyne), 56.00 (C), 55.77 (C×2), 45.77 (CH), 44.55 (—CH$_2$—NH), 38.57 (CH$_2$—S), 33.80 (CH$_2$—C=O), 32.11 (t, 22.83 Hz, CF$_2$—CH$_2$), 29.01 (—CH$_2$—CH$_2$—C=O), 23.67, 21.49 (—CH$_2$CH$_2$—S), 19.45 (2×CH$_3$), 19.07 (—CH$_3$); $^{19}$F NMR (CDCl$_3$, 100 MHz) −80.93 (3H, t, J=10.40 Hz), −114.35 (2H, septuplet, J=16.71 Hz), −122.03 (2H, s), −123.01 (2H, s), −123.45 (2H, s), −126.29 (2H, m). ESI Calcd for C$_{49}$H$_{55}$F$_{26}$N$_3$O$_9$S$_2$: 1388.30 [M+H$^+$], found m/z 1388.31 [M+H$^+$]. HRMS Calcd for C$_{49}$H$_{33}$F$_{26}$N$_3$O$_9$S$_2$: 1388.3043 [M+H$^+$], found m/z 1388.3036 [M+H$^+$].

5.2.2. Functionalization with Hydrophilic PolyTris Moieties

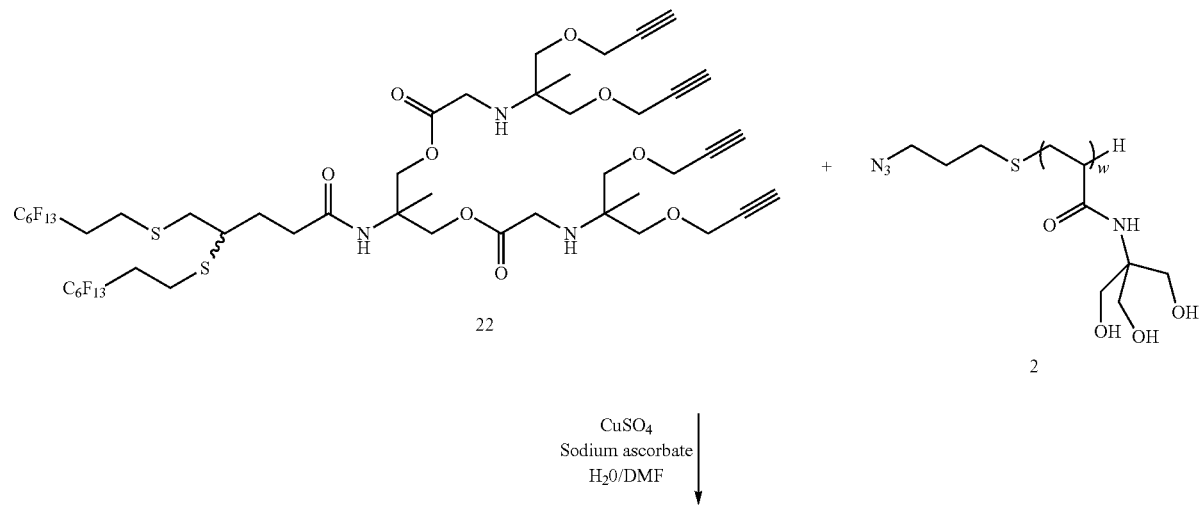

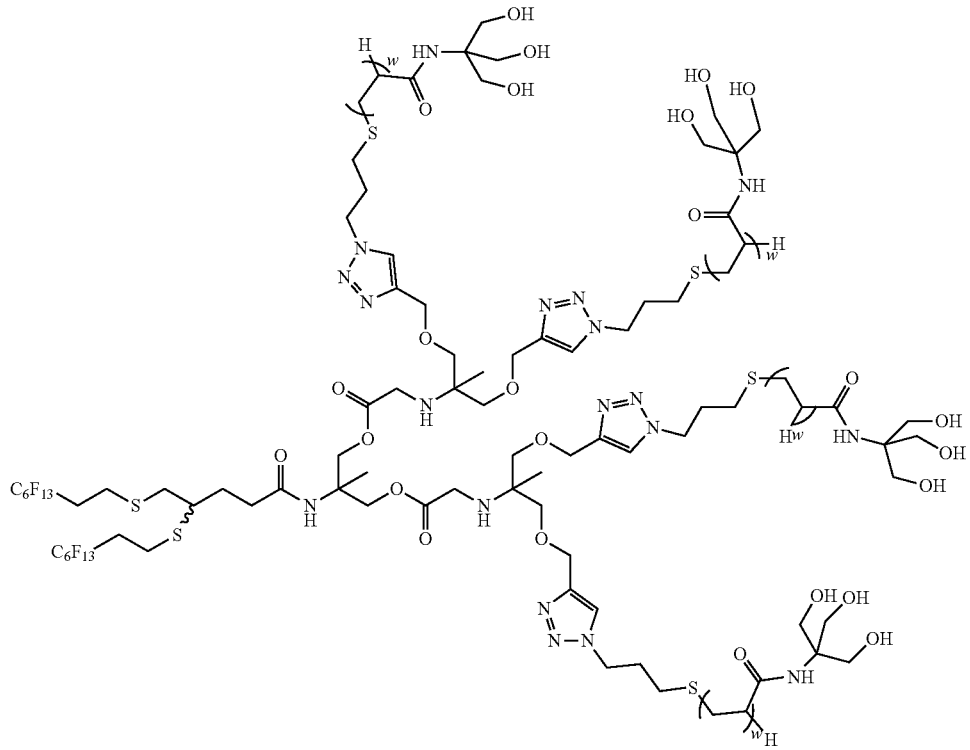

DiF6G1(ester) tetraTAC

Sodium ascorbate (30 mg, 0.15 mmol, 1.5 eq), compound 22 (140 mg, 0.1 mmol, 1 eq) and compound 2b (532 mg, 0.5 mmol, 5 eq) (DPn=5.2) are dissolved in a mixture of DMF (5 ml) and water (2 ml), the reaction mixture is heated at 55° C., and after 5 minutes copper sulfate pentahydrate (15 mg, 0.06 mmol, 0.6 eq) is added. The solution is heated at 55° C. during 7 hours, then the solution is filtered and passed through chelex beads, and the solvent is concentrated under high vacuum. The crude is dissolved in a mixture of MeOH/water 9/1, filtered and then purified over LH20 in MeOH/Water 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature without the water bath. The mixture is diluted with water, freeze-dried and further purified by FSPE to obtain 170 mg of desired compound (yield=30.0%, DPn=6).

The DPn is assessed by 1H-NMR in DMSO, where the integral of peaks at 4.40 ppm and 4.49 ppm is set for 16 Protons (Two $CH_2$ in α position ring), and by dividing the integral of the $CH_2$ protons of TRIS at 3.80 ppm by six or dividing the integral of the OH protons, between 5.43 and 4.64 ppm, by three.

$^1$H NMR (DMSO-d6, 400 MHz) δ (8.07 (4H, s, CH triazole), 7.82-6.90 (10H, c, NH), 5.43-4.64 (87H, c, OH), 4.48 (4H, s, $C_{TRIAZOLE}$—$CH_2$—O), 4.41 (4H, s, $CH_2$—$CH_2$—$N_{TRIAZOLE}$), 3.82-3.43 (225H, br, $CH_2$—OH, $CH_2$—O—), 2.98-2.85 (2H, m, CH, Ha $CH_2$—S), 2.84-2.70 (4H, c, $CF_2$—$CH_2$—$CH_2$—S, S—$CH_2$—$CH_2$—C=O), 2.59-1.84 (24H, c, $CF_2$—$CH_2$, —$CH_2$—C=O, $CH_2$—$CH_2$—$CH_2$—S, $CH_2$—C=O), 2.37-1.85 (60H, c, $CH_2$—$CH_2$—$CH_2$—S, $CH_2$—S, CH, $CH_2$—C=O, 1Ha —$CH_2$—$CH_2$—C=OCH—C=$O_{OLIGOMER}$), 1.82-1.06 (80H, c, 1 Hb —$CH_2$—$CH_2$—C=O $CH_2$ $_{OLIGOMER}$, $CH_3$). $^{19}$F NMR (CDCl$_3$, 100 MHz) −84.81 (3H, s), −113.38 (2H, br), −121.95 (2H, s), −122.92 (4H, s), −126.01 (2H, s)

6. Amphiphilic Dendrimers Functionalized with PEG Moieties-Generation 0 (G0)

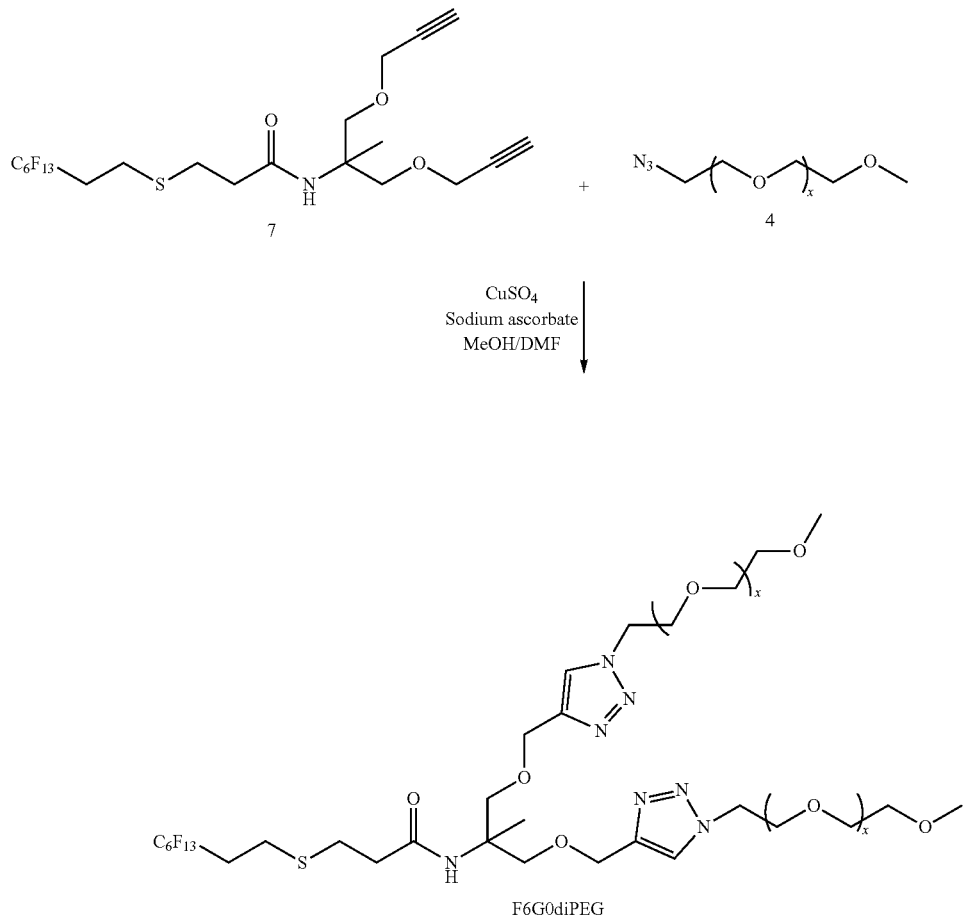

Synthesis of F6G$_O$diPEG (550) (SD370)

Sodium ascorbate (154 mg, 0.78 mmol, 1.2 eq), compound 7 (400 mg, 0.65 mmol, 1 eq) and 4 (1.11 g, 1.62 mmol, 2.5 eq) are dissolved in a mixture of MeOH (5 ml) and DMF (5 ml); the reaction mixture is heated at 50° C., and after 5 minutes copper sulfate (33 mg, 0.13, 0.2 eq) is added. The solution is heated overnight, and then the solution is concentrated under high vacuum and dissolved in 20 ml of DCM and then filtrated. The filtrate is purified by FSPE and then by LH20 in MeOH to afford 1.01 g of pure compound as a yellowish solid (yield=82.8%).

1H NMR (CDCl3, 400 MHz) δ 7.66 (2H, s, CH triazole), 6.57 (1H, s, NH), 4.56 (4H, s, C$_{TRIAZOLE}$—CH2-O), 4.48 (4H, t, J=5.11 Hz, CH2-CH2-N$_{TRIAZOLE}$), 3.81 (4H, t, J=5.11 Hz, CH2-CH2-N$_{TRIAZOLE}$), 3.59-3.55 (120H, br, CH2-O), 3.49 (m, 2H, CH2-O), 3.34-3.31 (10H, br, CH2-O, O—CH3), 2.77 (2H, t, 7.15 Hz, S—CH2-CH2-C=O), 2.70 (2H, m, CF2-CH2-CH2-S), 2.41 (2H, t, 7.15 Hz, S—CH2-CH2-C=O), 2.38-2.27 (2H, m, CF2-CH2), 1.31 (6H, s, CH3); 13C NMR (CDCl3, 100 MHz) δ 170.75 (C=O), 144.66 (Ctriazole), 123.60 (CH$_{TRIAZOLE}$), 71.93 (CH2-O), 70.55 (CH2-O), 69.43 (—O—CH2-CH2-N$_{TRIAZOLE}$), 64.58 (C$_{TRIAZOLE}$—CH2-O), 59.00 (OMe), 56.80 (CH2-C), 56.67 (C), 50.67 (CH2-O), 50.22 (CH2-Ntriazole), 37.10 (S—CH2-CH2-C=O), 32.02 (CH2-CF2), 27.67 (S—CH2-CH2-C=O), 22.79 (CF2-CH2-CH2-S), 18.91 (CH3); 19F NMR (CDCl3, 100 MHz) −80.78 (3H, t, J=9.27 Hz), ¬ −114.31 (2H, m), −121.94 (2H, br), −122.91 (2H, br), 123.42 (2H, br) −126.19 (2H, br).

7. Amphiphilic Dendrimers with AB3 Building Blocks

7.1. Synthesis of a Mannose Azide Hydrophilic Moiety

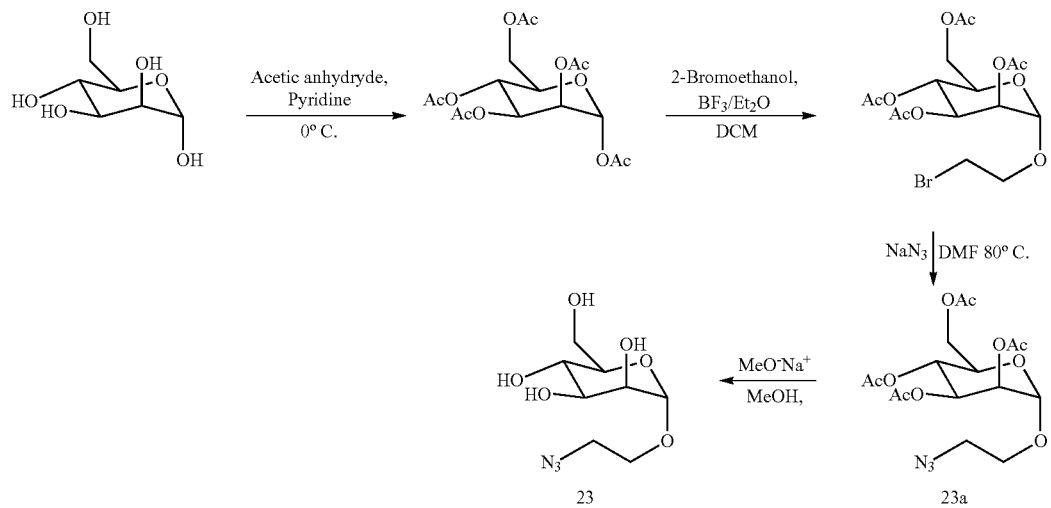

The synthesis of compound 23a was already described in J. Org. Chem., 73 (14), 5602-5605 (2008).

Synthesis of 2-azidoethyl 2,3,4,6-tetra-O-acetyl-α-D-mannopyranoside (23)

To a solution of compound 23a (0.4979 g, 1.19 mmol) in 20 ml of methanol is added a pinch of sodium methoxide until pH 9-10. The resulting mixture is stirred overnight and is subsequently filtered, and neutralized with IRC50 resin (pH 5-6). The solvent is removed under high vacuum, to give 273 mg of compound 23 in quantitative yield. The purity of the crude product is sufficient to be used without purification for the following Cu(I)-catalysed azide-alkyne [1,3]-dipolar cycloaddition reaction.

$^1$H NMR (MeOD, 400 MHz) δ 4.83 (1H, CH-1), 3.91 (1H, m, HaO—CH$_2$—CH$_2$), 3.87-3.80 (2H, m, CH-2, HaO—CH$_2$), 3.77-3.70 (2H, CH-3, Hb CH$_2$—O sugar), 3.68-3.60 (2H, m, HbO—CH$_2$—CH$_2$, CH-4), 3.60-3.54 (1H, m, CH-5), 3.34 (2H, t, J=4.87 Hz, O—CH$_2$—CH$_2$); $^{13}$C NMR (MeOD, 100 MHz) δ 101.66 (C-1 sugar), 74.70 (CH-5), 72.36 (CH-3), 71.92 (CH-2), 68.35 (CH-4), 67.64 (O—CH$_2$—CH$_2$), 62.65 (CH$_2$—O), 51.65 (CH$_2$—N$_3$).

7.2. Synthesis of the Bicatenar Scaffold diF6G$_0$ (AB3)

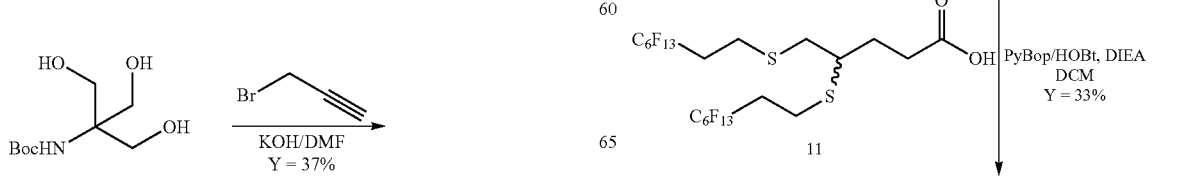

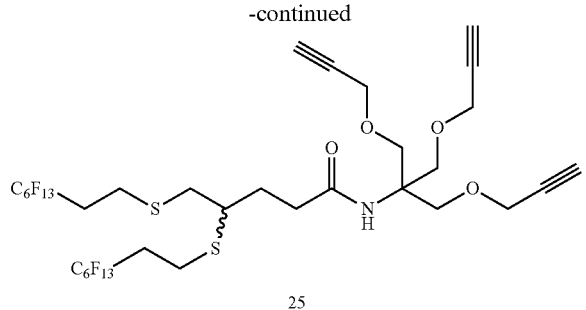

The synthesis of compound 24 was already described in J. Org. Chem., 73 (14), 5602-5605 (2008).

Synthesis of Compound N-(1,3-bis(prop-2-yn-1-yloxy)-2-((prop-2-yn-1-yloxy)methyl)propan-2-yl)-4,5-bis((3,3,4,4,5,5,6,6,7,7,8,8,8-tridecafluorooctyl)thio)pentanamide (25) (EG08)

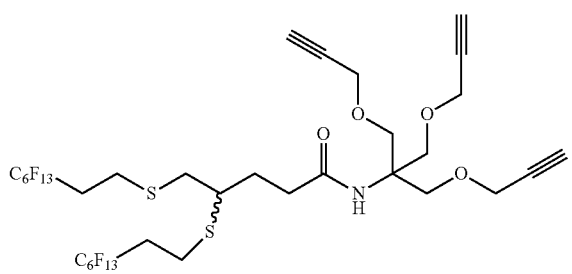

To a solution of 11 (1.31 g, 1.53 mmol, 1 eq), HOBt (41 mg, 0.31 mmol, 0.2 eq), PyBop (874 mg, 1.68 mmol, 1.1 eq) and DIEA (0.79 ml, 4.6 mmol, 3 eq) in 20 ml of DCM, after 5 min of stirring, compound 24 (0.59 g, 1.68 mmol, 1.1 eq) is added. After 5 hours, the crude mixture is washed three times with a 0.1 M HCl solution and two times with water and subsequently dried over $Na_2SO_4$. The crude is purified over $SiO_2$ (Cyclohexane 8/Ethyl acetate 2) to afford 542 mg pure 25 as a white powder (yield=33%). TLC Rf=0.49 (Cyclohexane/Ethyl acetate 7/3)

$^1$H NMR (CDCl$_3$, 400 MHz) δ 5.75 (1H, s, NH), 4.12 (6H, d, J=2.35 Hz CH$_2$—C Alcyne), 3.82 (6H, dd, J=9.20, 15.47 Hz CH$_2$—O), 2.91-2.82 (2H, m, CH, Ha CH$_2$—S), 2.80-2.70 (5H, m, Hb CH$_2$—S, CH$_2$—S), 2.46-2.30 (8H, m, CH$_2$Alcyne, CF$_2$—CH$_2$, —CH$_2$—C=O), 2.22-2.12 (1Ha, m, —CH$_2$—CH$_2$—C=O) 1.77-1.67 (1Hb, m, —CH$_2$—CH$_2$—C=O), 1.39 (3H, s, CH$_3$); $^{13}$C NMR (CDCl$_3$, 100 MHz) δ 172.05 (C=O), 79.57 (C Alcyne), 74.75 (CH Alcyne), 68.63 (CH$_2$—O), 59.39 (C), 58.75 (CH$_2$—C), 45.88 (CH), 38.82 (CH$_2$—S), 34.03 (CH$_2$—C=O), 32.19 (t, J=22.34 Hz, CF$_2$—CH$_2$), 29.42 (—CH$_2$—CH$_2$—C=O), 23.75 (CH$_2$—S), 21.81 (CH$_2$—S); $^{19}$F NMR (CDCl$_3$, 100 MHz) −81.03 (3H, t, J=10.46 Hz), −114.37 (2H, m,), −122.06 (2H, s), −123.05 (2H, s), −123.48 (2H, m), −126.34 (2H, m). ESI Calcd for $C_{34}H_{31}F_{26}NO_4S_2$: 1076.13 [M+H$^+$], found m/z 1076.14 [M+H$^+$]; HRMS Calcd for $C_{34}H_{31}F_{26}NO_4S_2$: 1076.1358 [M+H$^+$], found m/z 1076.1360 [M+H$^+$].

7.3. Functionalization with Glycosidic Moieties: Synthesis of diF6G$_0$triMan

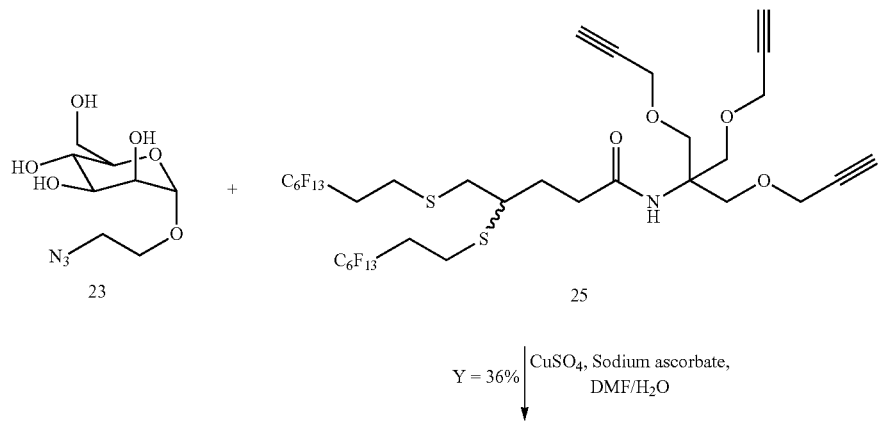

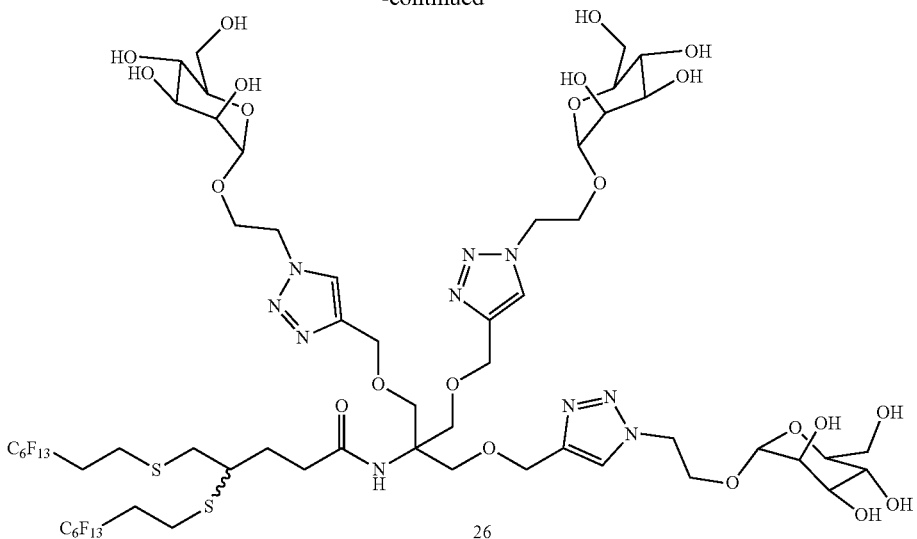

26

Compounds 23 (32 mg, 1,663 mmol, 3.5 eq.), 25 (50 mg, 0,475 mmol, 1 eq.) and sodium ascorbate (75 mg, 0.38 mmol, 0.8 eq.) are dissolved in a 5 ml mixture of DMF/H$_2$O 1/1. After stirring for 5 min, copper sulfate (24 mg, 0,095 mmol, 0.2 eq.) is added and the resulting mixture is heated at 50° C. for 4 days. The solution is filtered and passed through chelex beads, and then the solvent is evaporated under high vacuum. The crude is dissolved in MeOH, filtered and purified over LH20 using pure MeOH as eluent. After evaporation of the solvent under vacuum, compound 26 is obtained (31 mg) as a white powder (yield=36.2%).

$^1$H NMR (CDCl$_3$, 400 MHz) δ 8.00 (3H, s, C—H triazole), 4.73 (12H, m, OH sugar), 4.61 (3H, CH-1), 4.59-4.39 (12H, CH$_2$—N, CH$_2$—Ctriazole), 3.93 (3H, m, HaO—CH$_2$—CH$_2$), 3.78 (3H, m, HbO—CH$_2$—CH$_2$), 3.65-3.55 (9H, CH$_2$—O, Ha CH$_2$—O sugar), 3.52 (3H, s, CH-2 sugar), 3.45-3.38 (9H, m, Hb CH$_2$—O sugar, CH-3, CH-4 sugar), 3.15 (3H, m, CH-5 sugar) 2.91 (2H, m, CH, Ha CH$_2$—S), 2.80-2.70 (5H, m, Hb CH$_2$—S, CH$_2$—S), 2.60-2.43 (4H, m, CF$_2$—CH$_2$), 2.36-2.18 (2H, m, —CH$_2$—C=O), 1.97 (1Ha, m, —CH$_2$—CH$_2$—C=O), 1.58 (1Hb, m, —CH$_2$—CH$_2$—C=O); $^{13}$C NMR (CDCl$_3$, 100 MHz) δ 172.40 (C=O), 143.89 (C triazole), 124.00 (CH triazole), 99.84 (C-1 sugar), 74.11 (CH-5 sugar), 70.82 (CH-4 sugar), 70.06 (CH-2 sugar), 68.12 (CH$_2$—O), 67.83 (CH$_2$—O), 66.77 (C-3 sugar), 64.89 (O—CH$_2$—CH$_2$), 64.11 (C), 61.14 (CH$_2$—O sugar), 49.23 (CH$_2$—N), 44.97 (CH), 37.06 (CH$_2$—S), 32.92 (CH$_2$—C=O), 32.22 (m, CF$_2$—CH$_2$), 29.20 (—CH$_2$—CH$_2$—C=O), 22.32 (CH$_2$—S), 20.93 (CH$_2$—S); $^{19}$F NMR (CDCl$_3$, 100 MHz) -80.72 (3H, t, J=10.46 Hz), -113.50 (2H, m,), -122.05 (2H, s), -123.04 (4H, s), -126.18 (2H, m). ESI Calcd for C$_{58}$H$_{76}$F$_{26}$N$_{10}$O$_{22}$S$_2$: 1823.41 [M+H$^+$], found m/z 1823.43 [M+H$^+$]; HRMS Calcd for C$_{58}$H$_{76}$F$_{26}$N$_{10}$O$_{22}$S$_2$: 1823.4240 [M+H$^+$], found m/z 1823.4250 [M+H$^+$].

8. Synthesis of Hydrocarbon DendriTAC 8.1. Synthesis of the Monocatenar Scaffold (Via Mickaël Addition) with Different Hydrocarbon Chain Lengths (AB3 Building Blocks)

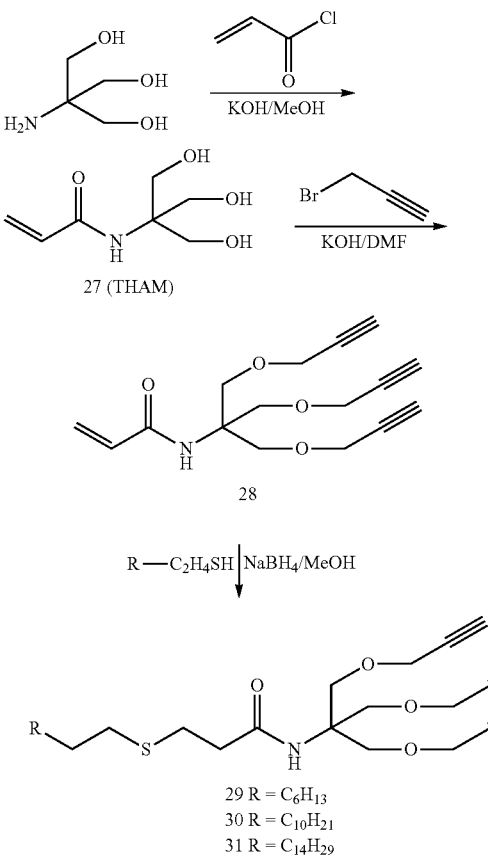

a) Synthesis of Tris(Hydroxymethyl)Acrylamidomethane (THAM) (Compound 27)

Synthesis of compound 27 was performed using the procedure described by Pucci et al. (*Eur. Polym. J.* 1991, 27, 1101). To a stirred solution of tris(hydroxymethyl)aminomethane (3.00 g, 24.8 mmol) in methanolic potassium hydroxide 3N, at 0° C. within a pH range between 8 and 9, acryloyl chloride (3.60 ml, 44.6 mmol) was added dropwise. The reaction mixture was stirred at 0° C. for 1 h and then allowed to warm up to room temperature. After 4 h, the reaction mixture was filtered and the filtrate evaporated in vacuo to dryness. After precipitation and recrystallization from methanol, the desired compound 27 was obtained (3.78 g, 87%) as a white powder. m.p. 136° C. (m.p.$_{theo}$ 140° C.); $v_{max}$ (NaCl)/cm$^{-1}$ 3420 s (br), 1653 s, 1560 m, 1540 m, 1018 m; $\delta_H$ (300 MHz; DMSO-d$_6$) 3.56 (d, 6H, J 5.7, CH$_2$), 4.76 (t, 3H, J 5.7, OH), 5.54 (dd, 1H, J 2.4, J 9.9, H$_a$), 6.02 (dd, 1H J 2.4, J 17.1 Hz, H$_b$), 6.37 (dd, J 9.9, J 17.1, H$_c$), 7.42 (s, 1H, NH); $\delta_c$ (75.5 MHz; DMSO-d$_6$) 60.6, 62.6, 125.2, 132.4, 165.5.

b) Synthesis of N-acryloyl-tris[(propargyloxy)methyl]aminomethane (Compound 28)

A solution of tris(hydroxymethyl)acrylamidomethane 27 (500 mg, 2.85 mmol) in anhydrous DMF (10 mL) was stirred at 0° C. with propargyl bromide (80 wt. % in Toluene 1.10 mL, 12.85 mmol). Portions of finely ground KOH (960 mg, 17.14 mmol) were added over a period of 30 min. The reaction mixture was stirred at room temperature and the course of the reaction was monitored by TLC (EtOAc/MeOH 7:3) until complete disappearance of 27. The mixture was concentrated to dryness and the residue partitioned between ethyl acetate (200 mL) and brine (200 mL). The organic layer was washed with water, dried with Na$_2$SO$_4$ and the solvent removed at reduce pressure to give the crude product, which was purified by flash chromatography (Hexanes/EtOAc 70:30). After crystallization from ethyl acetate/hexanes, compound 28 was obtained (0.630 g, 76%) as colorless needles. R$_f$ (EtOAc/Hexanes 7:3)=0.65; m.p. 85° C. (from EtOAc/Hexanes). $v_{max}$(NaCl)/cm$^{-1}$ 3300 s (br), 2124 s, 1658 s, 1623 s, 1555 s, 1101 s, 799 s (br); $\delta_H$ (300 MHz; CDCl$_3$) 2.44 (t, 3H, J 2.4, C≡CH), 3.89 (s, 6H, C$_a$CH$_2$O), 4.15 (d, 6H, J 2.4, OCH$_2$C≡CH), 5.58 (dd, 1H, J 1.8, J 9.9, H$_a$), 5.86 (s, 1H, NH), 6.06 (dd, 1H, J 9.9, J 17.1, H$_c$), 6.23 (dd, J 1.8, J 17.1, H$_b$); $\delta_C$ (75.5 MHz; CDCl$_3$) 58.6, 59.3, 68.4, 74.7, 79.5, 126.3, 131.4, 165.3; m/z (TOF$^+$ HRMS) for C$_{16}$H$_{19}$NO$_4$: 290.13868 [M+H]$^+$, found 290.13916; 312.12063 [M+Na]$^+$, found 312.12096.

c) Synthesis of Compound N-(1,3-bis(prop-2-yn-1-yloxy)-2-((prop-2-yn-1-yloxy)methyl)propan-2-yl)-3-(octylthio)propanamide (compound 29 R=C$_6$H$_{13}$)

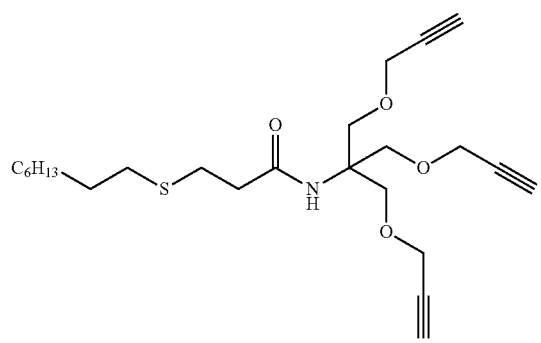

29

NaBH$_4$ (327 mg, 8.65 mmol, 2.5 eq) is added by portion to a cold solution of octanethiol (0.53 g, 3.63 mmol, 1.05 eq) in dry methanol (10 ml). The reaction mixture is stirred for 30 mn at 0° C. Then this solution is carefully added to a solution of 28 (1 g, 3.46 mmol, 1 eq) in dry methanol (90 ml) and the resulting mixture is stirred for 24 h. After 24 h another 0.5 eq of octanethiol and NaBH$_4$ are added in the same way as previously and the mixture is stirred for another 24 h. The solvent is evaporated in vacuo to dryness, the crude is purified over silica gel (cyclohexane/EtOAc 9:1-7:3 as eluent) to afford compound 29 (1.2 g, yield=79.6%) as a pure product.

$^1$H NMR (CDCL$_3$, 400 MHz) $\delta$ 5.83 (NH), 4.14 (6H, d, J=2.38 Hz, CH$_2$—C≡CH), 3.83 (6H, s, CH2-O), 2.75 (2H, t, J=7.35 Hz, S—CH$_2$—CH2-C═O), 2.50 (2H, t, J=7.45 Hz, S—CH$_2$—CH2), 2.46-2.35 (5H, m S—CH$_2$—CH$_2$—C═O, CH≡C), 1.56 (2H, m, CH$_2$—CH$_2$—S), 1.32 (10H, m, CH$_2$× 5), 0.86 (3H, t, J=6.89 Hz CH$_3$—CH$_2$); $^{13}$C NMR (CDCl$_3$, 100 MHz) $\delta$ 171.51 (C═O), 79.66 (C≡CH), 74.75 (C≡CH), 68.66 (CH$_2$—O), 59.46 (C), 58.79 (CH$_2$—C≡CH), 37.71 (S—CH$_2$—CH$_2$—C═O), 32.48 (S—CH$_2$—CH$_2$), 31.92 (CH$_2$), 29.75, 29.31, 29.30, 29.01, (CH$_2$×5), 27.77 (S—CH$_2$—CH$_2$—C═O), 22.75 (CH$_2$), 14.56 (CH$_3$). ESI Calcd for C13H18NO3: 436.25 [M+H+], found m/z 436.26 [M+H+]. HRMS calculated: C24H38NO4S: 436.2522 [M+H+], found m/z: 436.2524 [M+H+].

d) Synthesis of Compound N-(1,3-bis(prop-2-yn-1-yloxy)-2-((prop-2-yn-1-yloxy)methyl)propan-2-yl)-3-(dodecylthio)propanamide (compound 30 R=C$_{10}$H$_{21}$)

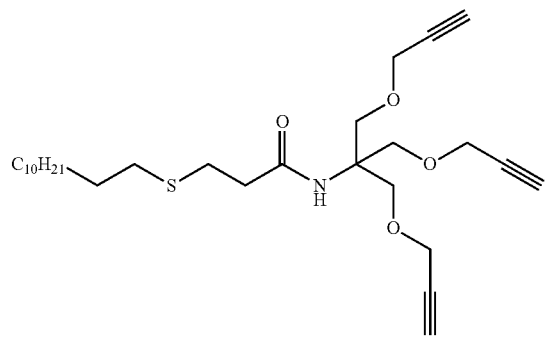

30

Same procedure as compound 29 (see table 1).

$^1$H NMR (CDCL$_3$, 400 MHz) $\delta$5.83 (NH), 4.10 (6H, d, J=2.40 Hz, CH$_2$—C≡CH), 3.79 (6H, s, CH$_2$—O), 2.71 (2H, t, J=7.45 Hz S—CH$_2$—CH$_2$—C═O), 2.46 (2H, t, J=7.55 Hz S—CH$_2$—CH$_2$), 2.42-2.33 (5H, m, S—CH$_2$—CH$_2$—C═O, CH≡C), 1.52 (2H, m, CH$_2$—CH$_2$—S), 1.38-1.11 (18H, m, CH$_2$×9), 0.86 (3H, t, J=6.85 Hz CH$_3$—CH$_2$); $^{13}$C NMR (CDCl$_3$, 100 MHz) $\delta$ 171.39 (C═O), 79.57 (C≡CH), 74.85 (C≡CH), 68.54 (CH$_2$—O), 59.51 (C), 58.68 (CH$_2$—C≡CH), 37.58 (S—CH$_2$—CH$_2$—C═O), 32.36 (S—CH$_2$—CH$_2$), 31.91 (CH$_2$), 29.65, 29.62, 29.60, 29.54, 29.45, 29.34, 29.26 29.17, 28.91, (CH$_2$×9) 27.66, (S—CH$_2$—CH$_2$—C═O), 22.68 (CH$_2$), 14.12 (CH$_3$). ESI Calcd for C$_{13}$H$_{18}$NO$_3$: 492.31 [M+H$^+$], found m/z 492.31 [M+H$^+$]. HRMS calculated: C$_{28}$H$_{45}$NO$_4$S: 492.3148 [M+H$^+$], found m/z: 492.3148 [M+H$^+$].

e) Synthesis of Compound N-(1,3-bis(prop-2-yn-1-yloxy)-2-((prop-2-yn-1-yloxy)methyl)propan-2-yl)-3-(hexadecylthio)propanamide (Compound 31 R=$C_{14}H_{29}$)

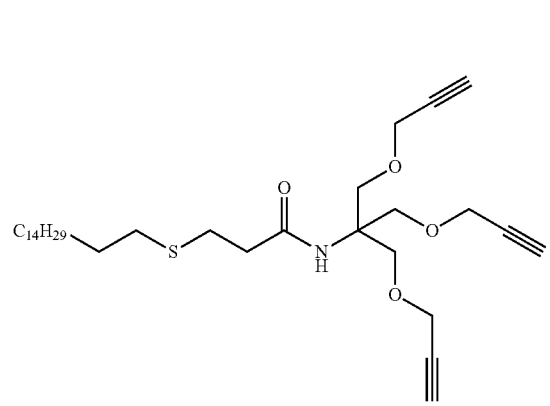

Same procedure as compound 29 (see table 1).

$^1$H NMR (CDCL$_3$, 400 MHz) δ 5.84 (NH), 4.14 (6H, d, J=2.37 Hz, CH$_2$—C≡CH), 3.84 (6H, s, CH$_2$—O), 2.76 (2H, t, J=7.46 Hz S—CH$_2$—CH$_2$—C=O), 2.51 (2H, t, J=7.55 Hz, S—CH$_2$—CH$_2$), 2.46-2.39 (5H, m, S—CH$_2$—CH$_2$—C=O, CH≡C), 1.56 (2H, m, CH$_2$—CH$_2$—S), 1.39-1.14 (26H, m, CH$_2$×13), 0.87 (3H, t, J=6.84 Hz CH$_3$—CH$_2$); $^{13}$C NMR (CDCl$_3$, 100 MHz) δ 171.53 (C=O), 79.69 (C≡CH), 74.77 (C≡CH), 68.70 (CH$_2$—O), 59.49 (C) 58.82 (CH$_2$—C≡CH), 37.74 (5-CH$_2$—CH$_2$—C=O), 32.51 (S—CH$_2$—CH$_2$), 32.05 (CH$_2$), 29.82, 29.79, 29.68, 29.48, 29.40, 29.05, 28.91, (CH$_2$×13), 27.66, (S—CH$_2$—CH$_2$—C=O), 22.81 (CH$_2$), 14.24 (CH$_3$). ESI Calcd for C$_{13}$H$_{18}$NO$_3$: 548.37 [M+H$^+$], found m/z 548.38 [M+H$^+$]. HRMS calculated: C$_{28}$H$_{45}$NO$_4$S: 548.3776 [M+H$^+$], found m/z: 548.3774 [M+H$^+$].

8.2. Synthesis of the Monocatenar Scaffold (Via Mickaël Addition) with Different Hydrocarbon Chain Lengths (AB2 Building Blocks)

32 R = $C_6H_{13}$
33 R = $C_{10}H_{21}$
34 R = $C_{14}H_{29}$ a) Synthesis of Compound N-(2-methyl-1,3-bis(prop-2-yn-1-yloxy)propan-2-yl)-3-(octylthio)propanamide (compound 32)

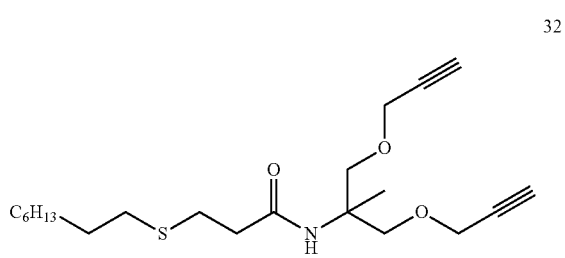

Same procedure as compound 29 (experimental conditions given on table 2).

TABLE 1

Experimental conditions of Mickaël addition (AB3 building blocks).

|  | 30 | 31 |
| --- | --- | --- |
| R—C$_2$H$_4$SH | Dodecanethiol 0.360 g (1.78.10$^{-3}$ mol) | Hexadecanethiol 0.190 g (7.37 10$^{-4}$ mol) |
| NaBH$_4$ | 0.161 g (4.255.10$^{-3}$ mol) | 0.066 g (1.75 10$^{-3}$ mol) |
| 28 | 0.4103 g (1.74.10$^{-3}$ mol) | 0.200 g (7.0210$^{-4}$ mol) |
| Mass of product | 0.749 g | 0.321 g |
| Yield | 88.3% | 83.5% |

¹H NMR (CDCL₃, 400 MHz) δ 5.85 (1H, s, NH), 4.16 (4H, d, J=2.36 Hz CH₂—C≡CH), 3.73 (4H, dd, J=9.04, 51.99 Hz CH₂—O), 2.71 (2H, t, J=7.41 Hz S—CH₂—CH₂—C=O), 2.52 (2H, t, J=7.41 Hz CH₂—S); 2.41 (2H, t, J=2.37 Hz CH≡C), 2.37 (2H, t, J=7.42 Hz S—CH₂—CH₂—C=O), 1.56 (2H, m, CH₂—CH₂—S), δ=1.42-1.19 (13H, m, CH—CH2, CH₃—C), 0.87 ppm (3H, t, J=6.89 Hz CH₃—CH2); ¹³C NMR (CDCl₃, 100 MHz) δ 171.35 (C=O), 79.72 (C≡CH), 74.77 (C≡CH), 72.19 (CH₂—O), 58.79 (CH₂—C≡CH), 56.59 (C), 37.87 (S—CH₂—CH₂—C=O), 32.57 (S—CH₂—CH₂), 31.96 (CH₂), 29.80, 29.35, 29.06, 27.87, (CH₂×6), 22.79 (CH₂), 19.30, 14.24 (CH₃). ESI Calcd for C₁₃H₁₈NO₃: 382.13 [M+H⁺], found m/z 382.24 [M+H⁺]. HRMS calculated: C₂₁H₃₅NO₃S: 382.2417 [M+H⁺], found m/z: 382.2416 [M+H⁺].

b) Synthesis of Compound N-(2-methyl-1,3-bis (prop-2-yn-1-yloxy)propan-2-yl)-3-(dodecylthio) propanamide (Compound 33)

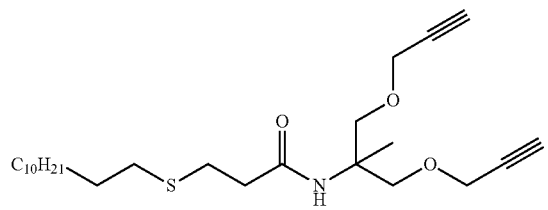

33

Same procedure as compound 29 (experimental conditions given on table 2).

¹H NMR (CDCL₃, 400 MHz) δ 5.85 (1H, s, NH), 4.09 (4H, d, J=2.39 Hz CH₂—C≡CH), 3.60 (4H, dd, J=9.03, 50.47 Hz CH₂—O), 2.70 (2H, t, J=7.40 Hz S—CH₂—CH2-C=O), 2.45 (2H, t, J=7.40 Hz CH₂—S), 2.40 (2H, t, J=2.40 Hz S—CH₂—CH₂—C=O), 2.34 (2H, t, J=7.40 Hz CH≡C), 1.51 (2H, m, CH₂—CH₂—S), 1.36-0.94 (21H, m, CH₃—CH₂, CH₃—C), 0.81 ppm (3H, t, J=6.87 Hz CH3-CH2); ¹³C NMR (CDCl₃, 100 MHz) δ 171.15 (C=O), 79.56 (C≡CH), 74.68 (C≡CH), 71.96 (CH₂—O), 58.58 (CH₂—C≡CH), 56.40 (C), 37.64 (S—CH₂—CH₂—C=O), 32.35 (S—CH₂—CH₂), 31.87 (CH₂), 29.61, 29.59, 29.57, 29.51, 29.30, 29.22, 28.87, 27.68, (CH₂×10), 22.64 (CH₂), 19.14, 14.09 (CH₃). ESI Calcd for C₁₃H₁₈NO₃: 438.30 [M+H⁺], found m/z 438.30 [M+H⁺]. HRMS calculated: C₂₅H₄₃NO₃S: 438.3039 [M+H⁺], found m/z: 438.3042 [M+H⁺].

c) Synthesis of Compound N-(2-methyl-1,3-bis (prop-2-yn-1-yloxy)propan-2-yl)-3-(hexadecylthio) propanamide (Compound 34)

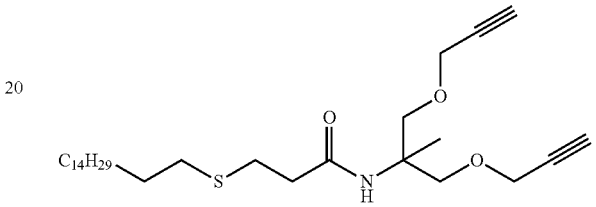

34

Same procedure as compound 29 (experimental conditions given on table 2).

¹H NMR (CDCL₃, 400 MHz) δ 5.85 (1H, s, NH), 4.10 (4H, d, J=2.37 Hz CH₂—C≡CH); 3.61 (4H, dd, J=9.03, 50.74 Hz CH2-O), 2.71 (2H, t, J=7.40 Hz S—CH₂—CH₂—C=O), 2.46 (2H, t, J=7.40 Hz CH₂—S), 2.40 (2H, t, J=2.37 Hz S—CH₂—CH₂—C=O), 2.35 (2H, t, J=7.40 Hz CH≡C), 1.52 (2H, m, CH₂—CH₂—S), 1.38-1.11 (29H, m, CH₃—CH₂, CH₃—C), 0.82 (3H, t, J=6.85 Hz CH₃—CH₂); ¹³C NMR (CDCl₃, 100 MHz) δ 171.17 (C=O), 79.59 (C≡CH), 74.69 (C≡CH), 72.01 (CH₂—O), 58.62 (CH2-C≡CH), 56.44 (C), 37.69 (S—CH₂—CH₂—C=O), 32.39 (S—CH₂—CH₂), 31.92 (CH₂), 29.69, 29.66, 29.61, 29.55, 29.36, 29.26, 28.91, 27.72, (CH₂×10), 22.69, (CH₂), 19.17, 14.12 (CH₃). ESI Calcd for C₁₃H₁₈NO₃: 494.36 [M+H⁺], found m/z 494.37 [M+H⁺]. HRMS calculated: C₂₉H₅₁NO₃S: 494.3666 [M+H⁺], found m/z: 494.3668 [M+H⁺].

TABLE 2

Experimental conditions of Mickaël addition (AB2 building blocks).

| | 32 | 33 | 34 |
|---|---|---|---|
| R—C₂H₄SH | Octanethiol | Dodecanethiol | Hexadecanethiol |
| | 0.269 g (1.84.10⁻³ mol) | 0.269 g (1.84.10⁻³ mol) | 0.231 g (8.9.10⁻⁴ mol) |
| NaBH₄ | 0.165 g (4.37.10⁻³ mol) | 0.1598 g (4.22.10⁻³ mol) | 0.0804 g (2.13.10⁻³ mol) |
| (compound 6) | 0.412 g (1.75.10⁻³ mol) | 0.412 g (1.75.10⁻³ mol) | 0.200 g (8.5.10⁻⁴ mol) |
| Mass of Product | 0.450 g | 0.237 g | 0.280 g |
| Yield | 67.44% | 45.20% | 66.71% |

8.3. Functionalization with Hydrophilic PolyTris Moieties a) Synthesis of Hydrocarbon dendriTAC H8G$_0$triTAC (5*3) (Compound 35) (VL2)

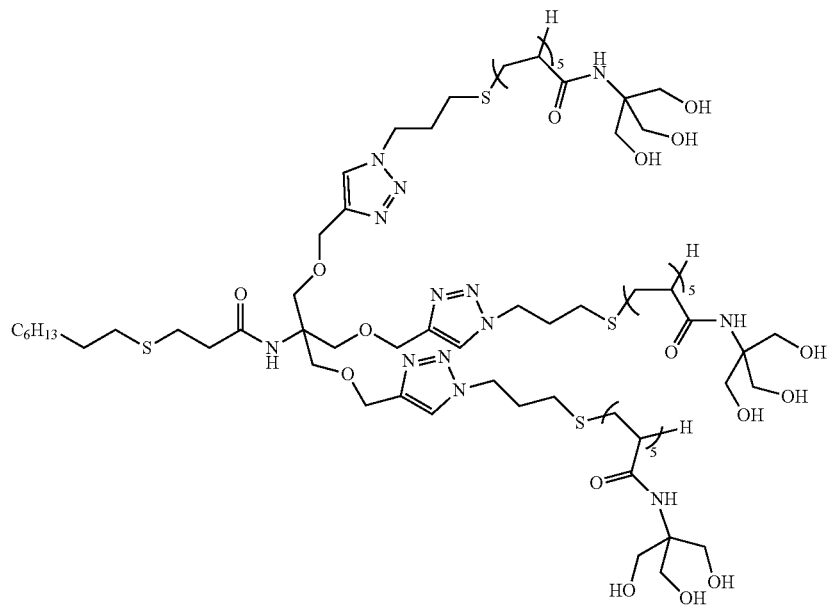

35

Sodium ascorbate (57 mg, 0.286 mmol, 1.1 eq), compound 32 (112 mg, 0.26 mmol, 1 eq) and azido-polyTRIS oligomer 2b (DPn~5) (1.006 g, 1.01 mmol, 3.9 eq) are dissolved in mixture of DMF (7 ml) and water (4 ml), the reaction mixture is heated to 55° C., and after 5 minutes copper sulfate pentahydrate (17 mg, 0.068 mmol, 0.26 eq) is added. The solution is stirred at 60° C. during 3 hours and then at room temperature overnight. The solution is filtered and passed through chelex beads, and then the solvent is carefully removed under high vacuum. The crude is dissolved in a mixture of MeOH/water 9/1 and filtered and then purified over LH20 MeOH/Water 9/1. The purification is followed by TLC (Ethyl Acetate/MeOH 5/5) only fraction where only compounds staying at the start were recovered. The solvent is carefully removed in vacuo at a temperature around 0° C. at the beginning and then at room temperature without the water bath, diluted with water and freeze dried to obtain 377 mg of compound 35 as a white powder (yield=43.03%).

$^1$H NMR (DMSO-d6, 400 MHz) δ 8.05 (3H, s, CH triazole), 7.71-6.79 (16H, c, NH), 5.39-4.56 (48H, c, OH), 4.47 (6H, s, C$_{TRIAZOLE}$—CH$_2$—O), 4.40 (6H, s, CH$_2$—CH$_2$—N$_{TRIAZOLE}$), 3.86-3.42 (133H, br, CH$_2$—OH, CH$_2$—O—), 2.68 (4H, c, CH$_2$—CH$_2$—S, S—CH$_2$—CH$_2$—C=O), 2.37-1.86 (27H, c, CH$_2$—CH$_2$—CH$_2$—S, CH$_2$—S, CH, CH$_2$—C=O, 1Ha —CH$_2$—CH$_2$—C=OCH—C=O$_{OLIGOMER}$), 1.82-1.09 (42H, c, CH$_{2 alkyl\ chain}$ CH$_{2\ OLIGOMER}$), 0.85 (3H, t, J=6.95 Hz CH$_3$).

b) Synthesis of Hydrocarbon dendriTAC H12G₀triTAC (5*3) (Compound 36) (VL15)

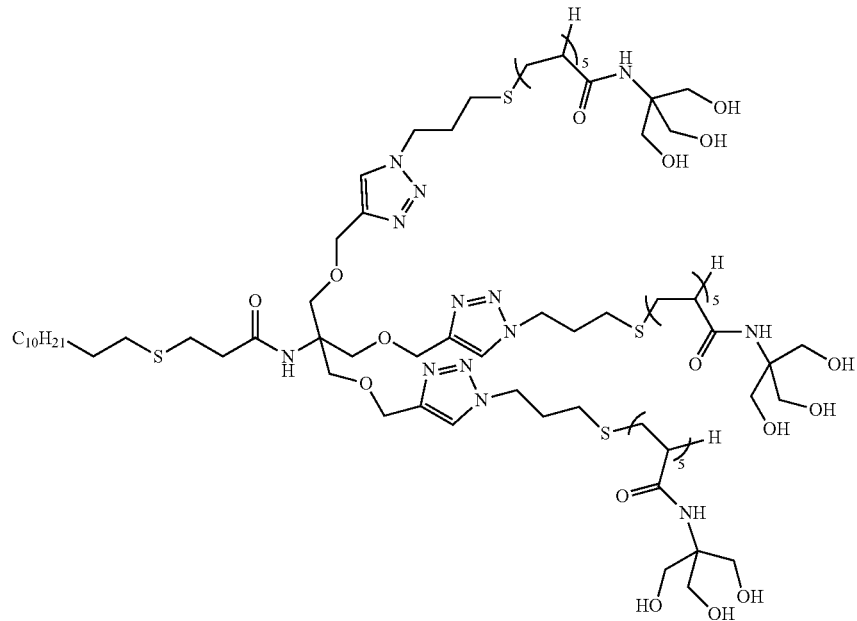

Same procedure as compound 35 (see experimental conditions on table 3).

¹H NMR (DMSO-d6, 400 MHz) δ 8.04 (3H, s, CH triazole), 7.78-6.69 (25H, c, NH), 5.43-4.57 (75H, c, OH), 4.48 (6H, d, J=7.31 Hz $C_{TRIAZOLE}$—CH₂—O), 4.40 (6H, s, CH₂—CH₂—N$_{TRIAZOLE}$), 3.86-3.37 (150H, br, CH₂—OH, CH₂—O—), 2.72 (4H, c, CH₂—CH₂—S, S—CH₂—CH₂—C=O), 2.29-1.84 (40H, c, CH₂—CH₂—CH₂—S, CH₂—S, CH, CH₂—C=O, 1Ha —CH₂—CH₂—C=O CH—C=O$_{OLIGOMER}$), 1.79-1.13 (75H, c, CH$_{2alkyl\ chain}$ CH₂ $_{OLIGOMER}$), 0.85 (3H, t, J=6.63 Hz CH₃).

c) Synthesis of Hydrocarbon dendriTAC H16G₀triTAC (5*3) (Compound 37) (VL20)

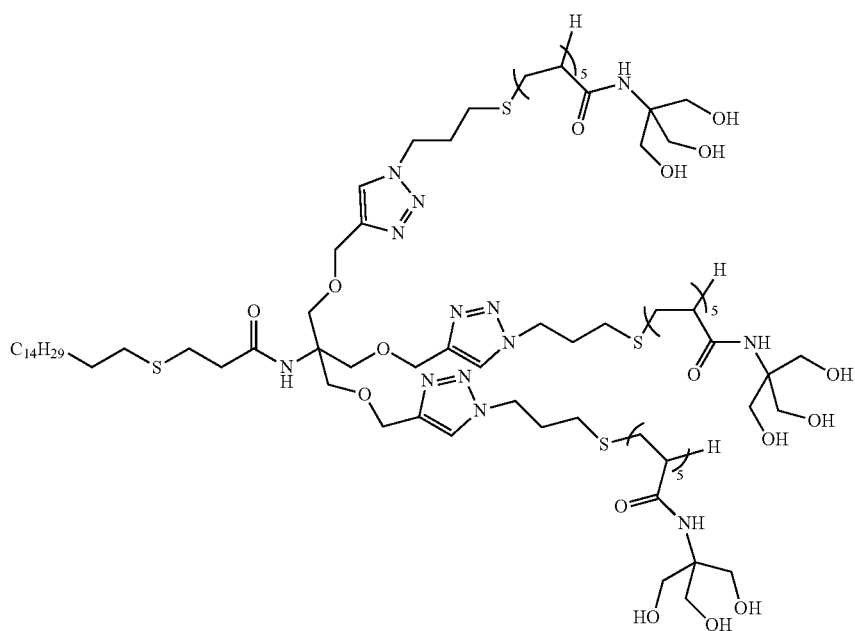

Same procedure as compound 35 (see experimental conditions on table 3).

$^1$H NMR (DMSO-d6, 400 MHz) δ 8.03 (3H, s, CH triazole), 7.74-6.75 (19H, c, NH), 5.50-4.56 (50H, c, OH), 4.47 (6H, d, J=7.64 Hz $C_{TRIAZOLE}$—$CH_2$—O), 4.39 (6H, s, $CH_2$—$CH_2$—$N_{TRIAZOLE}$), 3.91-3.41 (96H, br, $CH_2$—OH, $CH_2$—O—), 2.68 (4H, c, $CH_2$—$CH_2$—S, S—$CH_2$—$CH_2$—C=O), 2.32-1.83 (24H, c, $CH_2$—$CH_2$—$CH_2$—S, $CH_2$—S, CH, $CH_2$—C=O, 1Ha —$CH_2$—$CH_2$—C=O CH—C=$O_{OLIGOMER}$), 1.80-1.01 (50H, c, $CH_{2\,alkyl\,chain}$ $CH_{2\,OLIGOMER}$), 0.85 (3H, t, J=6.73 Hz $CH_3$).

d) Synthesis of Hydrocarbon dendriTAC H8G$_0$diTAC(5*2) (Compound 38) (VL13)

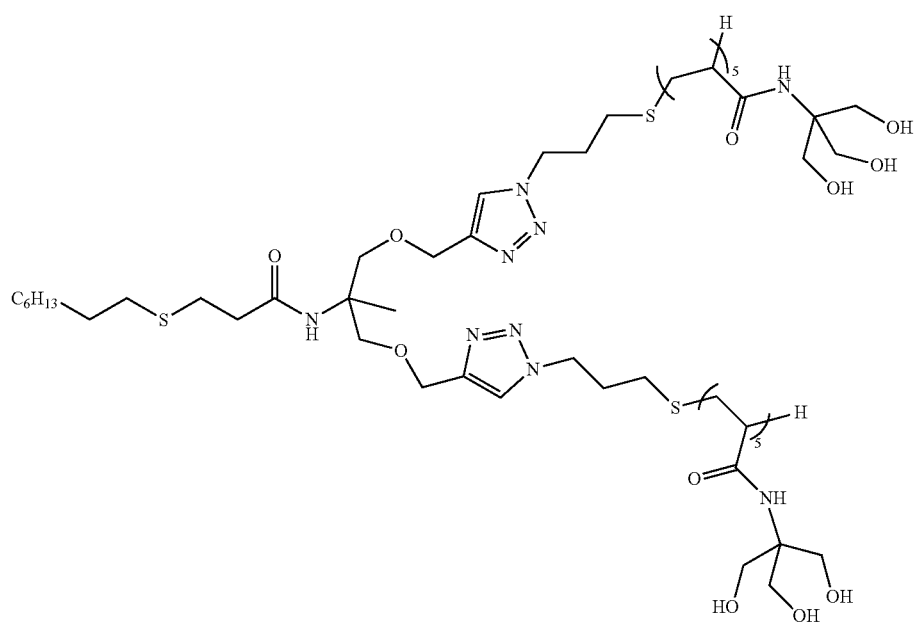

Same procedure as compound 35 (see experimental conditions on table 3); equivalents number of oligomer 2b is 2.6 instead of 3.9.

$^1$H NMR (DMSO-d6, 400 MHz) δ 8.04 (2H, s, CH triazole), 7.74-6.75 (19H, c, NH), 5.57-4.58 (54H, c, OH), 4.49 (4H, $C_{TRIAZOLE}$—$CH_2$—O), 4.40 (4H, s, $CH_2$—$CH_2$—$N_{TRIAZOLE}$), 3.97-3.43 (110H, br, $CH_2$—OH, $CH_2$—O—), 2.57 (3H, m, Ha $CH_2$—$CH_2$—S oligomer S—$CH_2$—$CH_2$—C=O), 2.45 (3H, m, Hb $CH_2$—$CH_2$—S oligomer $CH_2$—$CH_2$—S), 2.29 (2H, m, S—$CH_2$—$CH_2$—C=O), 2.27-1.85 (27H, c, $CH_2$—$CH_2$—$CH_2$—S, $CH_2$—S, CH, $CH_2$—C=O, 1Ha —$CH_2$—$CH_2$—C=OCH—C=$O_{OLIGOMER}$), 1.76-1.09 (50H, c, $CH_{2\,alkyl\,chain}$ $CH_{2\,OLIGOMER}$), 0.85 (3H, t, J=6.80 Hz $CH_3$).

e) Synthesis of Hydrocarbon dendriTAC H12G$_0$diTAC(5*2) (Compound 39) (VL14)

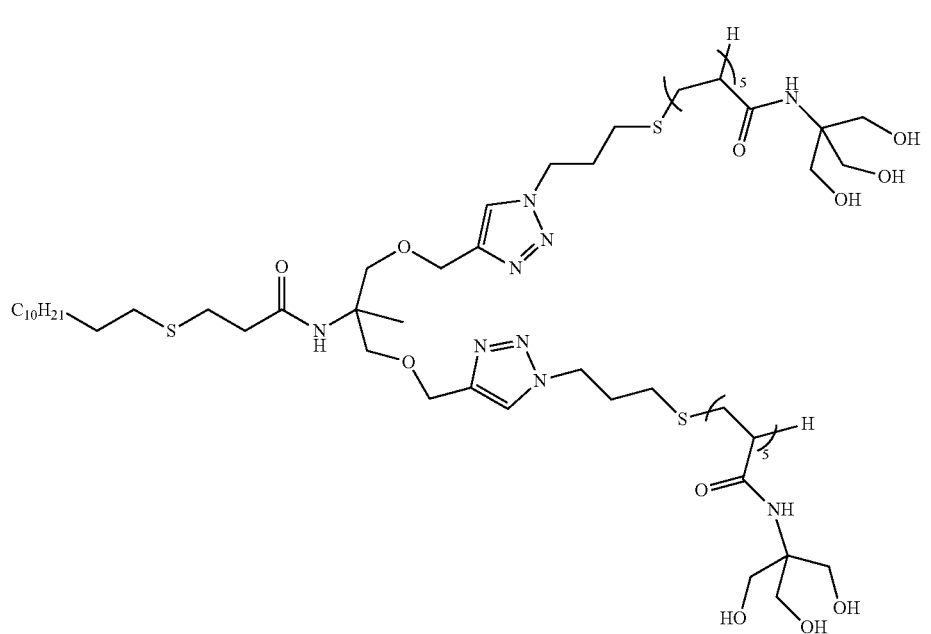

Same procedure as compound 35 (see experimental conditions on table 3); equivalents number of oligomer 2b is 2.6 instead of 3.9.

$^1$H NMR (DMSO-d6, 400 MHz) δ 8.05 (2H, s, CH triazole), 7.77-6.72 (21H, c, NH), 5.30-4.56 (53H, c, OH), 4.49 (4H, C$_{TRIAZOLE}$—CH$_2$—O), 4.40 (4H, s, CH$_2$—CH$_2$—N$_{TRIAZOLE}$), 3.95-3.41 (104H, br, CH$_2$—OH, CH$_2$—O—), 2.57 (3H, m, Hb CH$_2$—CH$_2$—S oligomer S—CH$_2$—CH$_2$—C=O), 2.45 (3H, m, Hb CH$_2$—CH$_2$—S oligomer CH$_2$—CH$_2$—S), 2.31 (2H, m, S—CH$_2$—CH$_2$—C=O), 2.26-1.82 (27H, c, CH$_2$—CH$_2$—CH$_2$—S, CH$_2$—S, CH, CH$_2$—C=O, 1Ha —CH$_2$—CH$_2$—C=OCH—C=O$_{OLIGOMER}$), 1.77-1.11 (50H, C, CH$_{2 alkyl\ chain}$ CH$_2$ $_{OLIGOMER}$), 0.85 (3H, t, J=6.75 Hz CH$_3$).

f) Synthesis of Hydrocarbon dendriTAC H16G$_0$diTAC(5*2) (Compound 40) (VL23)

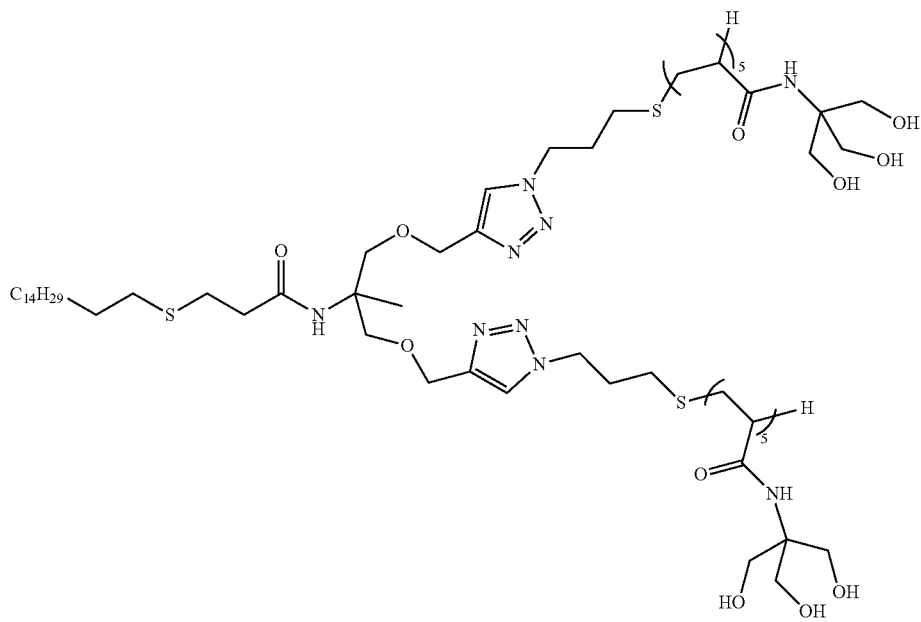

Same procedure as compound 35 (see experimental conditions on table 3); equivalents number of oligomer 2b is 2.6 instead of 3.9.

$^1$H NMR (DMSO-d6, 400 MHz) δ 8.04 (2H, s, CH triazole), 7.79-6.56 (18H, c, NH), 5.45-4.57 (50H, c, OH), 4.48 (4H, d, J=7.52 Hz $C_{TRIAZOLE}$—CH$_2$—O), 4.40 (4H, s, CH$_2$—CH$_2$—N$_{TRIAZOLE}$), 3.93-3.41 (100H, br, CH$_2$—OH, CH$_2$—O—), 2.29-1.84 (25H, c, CH$_2$—CH$_2$—CH$_2$—S, CH$_2$—S, CH, CH$_2$—C=O, 1Ha —CH$_2$—CH$_2$—C=OCH—C=O$_{OLIGOMER}$), 1.79-1.03 (50H, c, CH$_{2\,alkyl\,chain}$ CH$_{2\,OLIGOMER}$), 0.85 (3H, t, J=6.70 Hz CH$_3$).

TABLE 3

Experimental conditions for the cycloaddition step.

| Final hydrocarbon DendriTAC | 35 | 36 | 37 | 38 | 39 | 40 |
|---|---|---|---|---|---|---|
| Propargyl compound | 32 | 33 | 34 | 29 | 30 | 31 |
| mass | 0.112 g | 0.075 g | 0.054 g | 0.150 g | 0.146 g | 0.150 g |
| mol | $2.57 \cdot 10^{-4}$ | $1.5 \cdot 10^{-4}$ | $9.87 \cdot 10^{-5}$ | $3.39 \cdot 10^{-4}$ | $3.34 \cdot 10^{-4}$ | $3.04 \cdot 10^{-4}$ |
| Oligomer 2b | 1.006 g | 0.775 g | 0.518 g | 1.059 g | 0.929 g | 1.631 g |
|  | ($1.01 \cdot 10^{-3}$ mol) | ($7.07 \cdot 10^{-4}$ mol) | ($3.85 \cdot 10^{-4}$ mol) | ($10.21 \cdot 10^{-4}$ mol) | ($8.85 \cdot 10^{-4}$ mol) | ($7.9 \cdot 10^{-4}$ mol) |
| Copper (II) sulfate | 17 mg | 17 mg | 6 mg | 32 mg | 23 mg | 20 mg |
|  | ($0.07 \cdot 10^{-4}$ mol) | ($6.81 \cdot 10^{-5}$ mol) | ($2.57 \cdot 10^{-5}$ mol) | ($1.02 \cdot 10^{-4}$ mol) | ($8.82 \cdot 10^{-5}$ mol) | ($7.9 \cdot 10^{-5}$ mol) |
| Sodium ascorbate | 57 mg | 49 mg | 215 mg | 85 mg | 71 mg | 66 mg |
|  | ($2.86 \cdot 10^{-4}$ mol) | ($2.47 \cdot 10^{-4}$ mol) | ($1.08 \cdot 10^{-4}$ mol) | ($4.32 \cdot 10^{-4}$ mol) | ($3.7 \cdot 10^{-4}$ mol) | ($7.9 \cdot 10^{-5}$ mol) |
| Mass of product | 0.377 g | 0.212 g | 0.130 g | 0.236 g | 0.499 g | 0.162 g |
| Yield | 43.03% | 40.69% | 28.80% | 29.99% | 62.87% | 21.74% |

9. Synthesis of PPIX Derivatives

9.1. Synthesis of 1-Amino-ω-Methoxy-PEG550

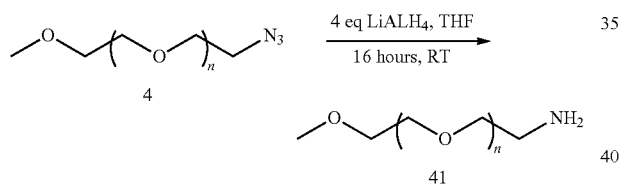

To a cold solution of 400 mg of compound 4 (0.69 mmol, 1 eq) in 20 ml of dry THF is added 105 mg of LiAlH4 (2.77 mmol, 4 eq), and the slurry is stirred during 16 hours at room temperature. Then a 10% solution of NaOH is added in a dropwise manner, then the solution is filtered over celite with a mixture of ethyl acetate and methanol, the filtrate is subsequently concentrated in vacuo to afford the pure compound 41 in quantitative yield.

9.2. Synthesis of Amphiphilic PPIX Derivatives

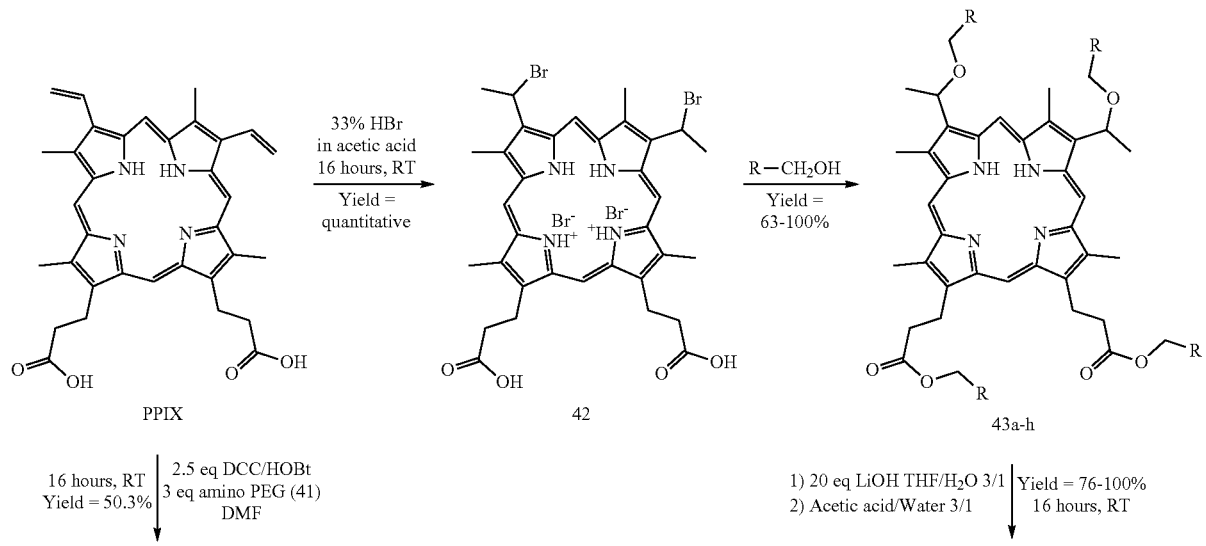

-continued

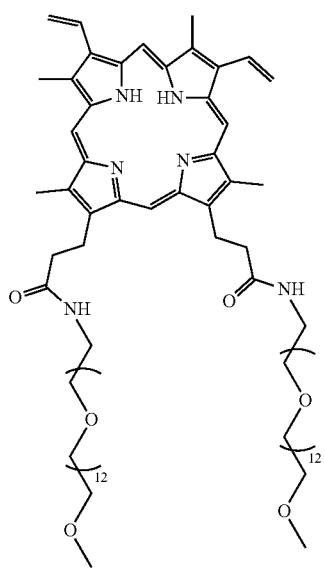

46

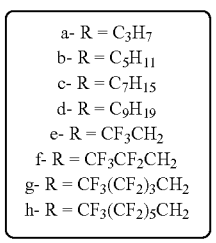

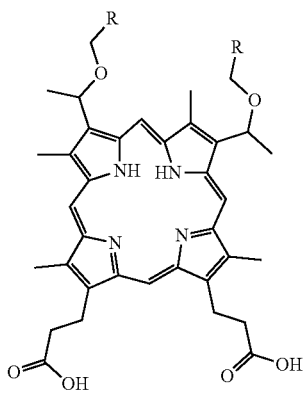

44a-h 2.5 eq DCC/HOBt
3 eq amino PEG (41)
DMF
→ 16 hours, RT
Yield = 32.2-65.3 %

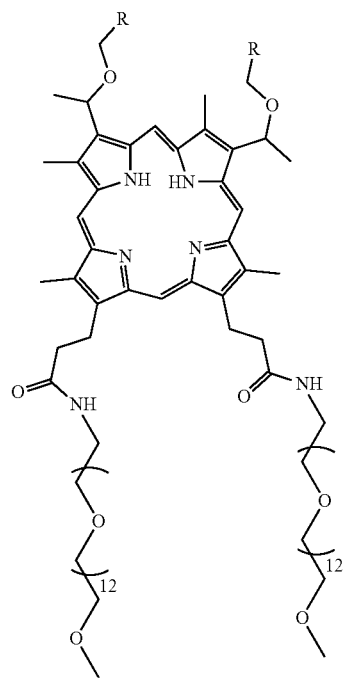

45a-h

The synthesis is a modified procedure derived from Lottner, C.; Bart, K C.; Bernhardt, G.; Brunner, H. *Journal of Medicinal Chemistry* 2002, 45, 2064.

Briefly, the PPIX is reacted with a mixture of HBr in acetic acid (33%). After removal of HBr and acetic acid, the resulting Bromo-PPIX analogue (42) is dissolved in the appropriate alcohol during 16 hours, which simultaneously gives the corresponding ether (addition on the two allylic units)/ester (addition on the propionic acid moieties) derivative 43. The two ester groups are subsequently saponified with 20 eq of LiOH in a mixture of THF and water (3/1); after acidic treatment, 1-amino-ω-methoxy-PEG550 (compound 41) is coupled to acid functions with DCC/HOBt as coupling reagent in DMF. After removal of the solvent the final product is purified over LH20 in DCM/MeOH 1/1 to give the final amphiphilic PPIX derivative 45.

9.2.1. Synthesis of Bromo-PPIX (Compound 42)

Typically, 334 mg of PPIX are dissolved in 35 ml of a solution of HBr in acetic acid (33%) during 24 hours, then the solvent is removed in vacuo to afford 590 mg of pure product in quantitative yield. We obtained protonated BrP-PIX where the counter anion can be either $Br^-$ or $CH_3COO^-$ according the NMR spectra there is two $CH_3COO^-$. Mw is considered to be 1002 g/mol.

9.2.2. Synthesis of Tetrasubstituted PPIX Derivatives (Compounds 43a to 43 h)

General Procedure:

100 mg of Bromo-PPIX 1 are dissolved in a few ml of alcohol and the resulting mixture is stirred during 16 hours. Then the reaction mixture is diluted with EtOAc and washed twice with a saturated solution of NaHCO$_3$, dried over Na$_2$SO$_4$, dried through high vacuum to afford pure compounds in quantitative yield:

a) Synthesis of Tetrasubstituted C4PPIXC4 (Compound 43a) (SD433 Butanol)

100 mg of BrPPIX are dissolved in 5 ml of butanol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 82 mg of pure 43a in quantitative yield.

$^1$H NMR (CDCl$_3$, 400 MHz) δ 10.77 (1H, d, J=2.92 Hz CH), 10.75, 10.20, 10.18 (3H, s, CH), 6.24 (2H, m, CH—O), 4.52 (4H, dt, J=7.72, 22.49 Hz CH$_2$—CH$_2$—C=O), 4.22 (4H, m, ester O—CH$_2$—CH$_2$), 3.92-3.68 (16H, m, CH$_3$, ether O—CH$_2$—CH$_2$), 3.40 (4H, dt, J=6.91, 21.00 Hz CH$_2$—CH$_2$), 2.39 (6H, d, J=6.66 Hz, CH$_3$), 1.89 (4H, m, ether O—CH$_2$—CH$_2$), 1.56 (6H, m, ester O—CH$_2$—CH$_2$), 1.42-1.24 (6H, m, ester O—CH$_2$—CH$_2$—CH$_2$), 0.97 (6H, m, CH$_3$), 0.85 (6H, t, J=7.43 Hz CH$_3$), −3.69 (2H, m, NH); $^{13}$C NMR (CDCl$_3$, 100 MHz) δ 173.45, 173.42 (C=O), 147.26-141.69, 140.61, 139.41, 138.66, 137.25, 136.65 (C pyrrole CH$_2$=CH), 98.95, 98.72, 96.86, 96.33 (CH$_2$=CH), 73.49 (CH—O), 69.42 (CH$_2$—O×2), 64.65 (CH$_2$—O ester×2), 37.34 (CH$_2$—C=O), 32.57 (ether O—CH$_2$—CH$_2$), 30.74, 29.86 (ester O—CH$_2$—CH$_2$), 25.65 (CH$_3$×2), 22.09, 22.03 (CH$_2$—CH$_2$), 19.75, 19.14 (CH$_2$) 14.10, 13.68 (CH$_2$—CH$_3$), 11.94, 11.83, 11.76, 11.72 (CH$_3$). ESI Calcd for C$_{50}$H$_{71}$N$_4$O$_6$: 823.54 [M+H$^+$], found m/z 823.54 [M+H$^+$] HRMS Calcd for C$_{58}$H$_{87}$N$_4$O$_6$: 823.5374 [M+H$^+$], found m/z 823.5378 [M+H$^+$].

b) Synthesis of Tetrasubstituted C6PPIXC6 (Compound 43b) (SD416.1 Hexanol)

100 mg of BrPPIX are dissolved in 3 ml of hexanol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 94 mg of pure 43b in quantitative yield.

$^1$H NMR (CDCl$_3$, 400 MHz) δ 10.71, 10.68 (1H, d, J=2.12 Hz CH), 10.17, 10.16 (3H, s, CH), 6.17 (2H, m, CH—O), 4.49 (4H, m, CH$_2$—CH$_2$—C=O), 4.11 (4H, m, ester O—CH$_2$—CH$_2$), 3.88-3.62 (16H, m, CH$_3$, ether O—CH$_2$—CH$_2$), 3.36 (4H, m, CH$_2$—CH$_2$), 2.34 (6H, d, J=6.66 Hz, CH$_3$), 1.84 (4H, m, ether O—CH$_2$—CH$_2$), 1.50 (4H, m, ester O—CH$_2$—CH$_2$), 1.42-1.04 (24H, m, CH$_2$), 0.77 (12H, m, CH$_3$), −3.62 (2H, br, NH); $^{13}$C NMR (CDCl$_3$, 100 MHz) δ 173.47 (C=O), 144.72-142.78, 140.43, 138.59, 137.22, 136.82 C pyrrole (CH$_2$=CH), 98.91, 98.72, 96.89, 96.39 (CH$_2$=CH), 73.58, 73.32 (CH—O), 69.72 (CH$_2$—O×2), 64.97 (CH$_2$—O ester×2), 37.35 (CH$_2$—C=O), 31.89 (ether O—CH$_2$—CH$_2$), 31.40, 30.44 (ester O—CH$_2$—CH$_2$), 25.74, 25.58 (CH$_3$×2), 22.72, 22.45, 22.09 (CH$_2$) 14.56, 14.40, 14.07, 13.90 (CH$_2$—CH$_3$), 12.38, 12.01, 11.89, 11.84 (CH$_3$). ESI Calcd for C$_{58}$H$_{87}$N$_4$O$_6$: 935.66 [M+H$^+$], found m/z 935.66 [M+H$^+$] HRMS Calcd for C$_{58}$H$_{87}$N$_4$O$_6$: 935.6626 [M+H$^+$], found m/z 936.6633 [M+H$^+$].

c) Synthesis of Tetrasubstituted C8PPIXC8 (Compound 43c) (SD416.3 Octanol)

100 mg of BrPPIX are dissolved in 2 ml of octanol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 105 mg of pure 43c in quantitative yield.

$^1$H NMR (CDCl$_3$, 400 MHz) δ 10.71, 10.69 (1H, d, J=4.63 Hz CH), 10.17, 10.16 (3H, s, CH), 6.19 (2H, m, CH—O), 4.50 (4H, dd, J=7.66, 15.30 Hz CH$_2$—CH$_2$), 4.13 (4H, dt, J=6.79, 6.79, 11.53 Hz ester O—CH$_2$—CH$_2$), 3.86-3.65 (16H, m, CH$_3$, ether O—CH$_2$—CH$_2$), 3.37 (4H, m, CH$_2$—CH$_2$—C=O), 2.34 (6H, dd, J=1.75, 6.61 Hz, CH$_3$), 1.84 (4H, m, ether O—CH$_2$—CH$_2$), 1.51 (4H, m, ester O—CH$_2$—CH$_2$), 1.43-0.98 (36H, m, CH$_2$), 0.77 (12H, m, CH$_3$), −3.61 (2H, br, NH); $^{13}$C NMR (CDCl$_3$, 100 MHz) δ 173.49 (C=O), 146.22-142.17, 140.55, 138.63, 137.21, 136.66 C pyrrole (CH$_2$=CH), 98.88, 98.67, 96.87, 96.38 (CH$_2$=CH), 73.57, 73.31 (CH—O), 69.72 (CH$_2$—O×2), 64.97, 63.12 (CH$_2$—O ester×2), 37.34 (CH$_2$—C=O), 32.89 (ether O—CH$_2$—CH$_2$), 31.85, 31.73 (ether O—CH$_2$—CH$_2$), 30.18, 29.62, 29.34, 29.14, 28.65 (ester O—CH$_2$—CH$_2$CH$_2$), 25.73, 25.58 (CH$_3$×2), 22.80, 22.68, 22.60, 22.08 (CH$_2$), 14.59, 14.13, 14.09, 13.65 (CH$_2$—CH$_3$), 12.61, 12.51, 12.37, 12.12 (CH$_3$) ESI Calcd for C$_{66}$H$_{103}$N$_4$O$_6$: 1047.79 [M+H$^+$], found m/z 1047.79 [M+H$^+$] HRMS Calcd for C$_{66}$H$_{103}$N$_4$O$_6$: 1047.7878 [M+H$^+$], found m/z 1047.7970 [M+H$^+$].

d) Synthesis of Tetrasubstituted C10PPIXC10 (Compound 43d) (SD439 Decanol)

46 mg of BrPPIX are dissolved in 0.8 ml of decanol and the resulting mixture is stirred during 16 hours. Then the reaction mixture is diluted with EtOAc and washed twice with a saturated solution of NaHCO$_3$, dried over Na$_2$SO$_4$ dried under high vacuum and the decanol remaining was removed by distillation under reduced pressure (temperature 80° C.) to afford 62 mg of pure 43d in quantitative yield.

$^1$H NMR (CDCl$_3$, 400 MHz) δ 10.65 (1H, s, CH), 10.63 (1H, d, J=5.48 Hz CH), 10.13, 10.11 (2H, s, CH), 6.13 (2H, m, CH—O), 4.45 (4H, m, CH$_2$—CH$_2$), 4.09 (4H, m, ester O—CH$_2$—CH$_2$), 3.85-3.55 (16H, m, CH$_3$, ether O—CH$_2$—CH$_2$), 3.32 (4H, t, J=7.61 Hz CH$_2$—CH$_2$—C=O), 2.29 (6H, d, J=6.65 Hz, CH$_3$), 1.80 (4H, m, ether O—CH$_2$—CH$_2$), 1.45 (4H, m, ester O—CH$_2$—CH$_2$), 1.38-0.94 (44H, m, CH$_2$), 0.82 (12H, m, CH$_3$), −3.67 (2H, br, NH); $^{13}$C NMR (CDCl$_3$, 100 MHz) δ 173.45 (C=O), 145.66-136.43 (C pyrrole CH$_2$=CH), 98.92, 98.66, 96.86, 96.37 (CH$_2$=CH), 73.44 (CH—O), 69.72 (CH$_2$—O×2), 64.98 (CH$_2$—O ester×2), 37.34 (CH$_2$—C=O), 32.95 (ether O—CH$_2$—CH$_2$), 32.05, 31.95 (ether O—CH$_2$—CH$_2$), 30.46-28.68 (ester O—CH$_2$—CH$_2$CH$_2$), 25.70, 25.66 (CH$_3$×2), 22.83, 22.76, 22.73, 22.09 (CH$_2$), 14.26, 14.24, 14.21, 14.19 (CH$_2$—CH$_3$), 11.98, 11.90, 11.78, 11.73 (CH$_3$) ESI Calcd for C$_{74}$H$_{119}$N$_4$O$_6$: 1159.91 [M+H$^+$], found m/z 1159.91

[M+H$^+$] HRMS Calcd for C$_{74}$H$_{119}$N$_4$O$_6$: 1159.9130 [M+H$^+$], found m/z 1159.9139 [M+H$^+$].

e) Synthesis of Fluoro-Tetrasubstituted CF1PPIXCF1 (Compound 43e) (SD416-4 CF3CH2CH2OH)

100 mg of BrPPIX are dissolved in 2 ml of 3,3,3-Trifluoropropan-1-ol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 105 mg of pure 43e in quantitative yield.

$^1$H NMR (CDCl$_3$, 400 MHz) δ 10.60, 10.58, 10.14, 10.09 (4H, s, CH), 6.19 (2H, m, CH—O), 4.43 (4H, m, CH$_2$—CH$_2$—C=O), 4.33 (4H, m, CH$_2$—O ester), 3.99 (4H, m, ether O—CH$_2$—CH$_2$), 3.77-3.63 (12H, m, CH$_3$), 3.33 (4H, m, CH$_2$—CH$_2$—C=O), 2.61 (4H, m, CF$_3$—CH$_2$—CH$_2$ ether), 2.46-2.24 (10H, m, ester O—CH$_2$—CH$_2$, CH$_3$), −3.62 (2H, br, NH); $^{13}$C NMR (CDCl$_3$, 100 MHz) δ 172.79 (C=O), 147.42-140.85, 139.44, 138.42, 137.53, 137.09 (C pyrrole CH$_2$=CH), 126.17 (qd, J$_{C,F}$=276.9, 59.8 Hz CF$_3$), 98.70, 98.42, 97.14, 96.30 (CH$_2$=CH), 74.11 (dd, J$_{C,F}$=72.32, 49.96 Hz CH—O), 62.45 (t, J$_{C,F}$=78.10 Hz ether CH$_2$—O×2), 57.40 (t, J$_{C,F}$=65.98 Hz CH$_2$—O ester× 2), 36.91 (CH$_2$—C=O), 34.98 (q, J$_{C,F}$=28.26 Hz ether CH$_2$—CF$_3$), 33.76-32.89 (m, ester CH$_2$—CF$_3$), 25.50, 25.39 (CH$_3$), 21.79 (CH$_2$—CH$_2$), 12.42, 11.93, 11.85, 11.69 (CH$_3$); $^{19}$F NMR (CDCl$_3$, 376 MHz) −64.36 (6F, m, CF$_3$), −64.98 (6F, m, CF$_3$). ESI Calcd for C$_{46}$H$_{51}$F$_{12}$N$_4$O$_6$: 236.13 [M+H$^+$], found m/z 983.36 [M+H$^+$]. HRMS Calcd for C$_{13}$H$_{18}$NO$_3$: 983.3617 [M+H$^+$], found m/z 983.3621 [M+H$^+$].

f) Synthesis of Fluoro-Tetrasubstituted CF2PPIXCF2 (Compound 43f) (SD416-5 CF3CF2CH2CH2OH)

100 mg of BrPPIX are dissolved in 2 ml of 3,3,4,4-Pentafluorobutan-1-ol and the resulting mixture is stirred during 48 hours. Then the reaction mixture is diluted with EtOAc and washed twice with a saturated solution of NaHCO$_3$, dried over Na$_2$SO$_4$ dried under high vacuum to afford 165 mg of pure 43f in quantitative yield.

$^1$H NMR (CDCl$_3$, 400 MHz) δ 10.65 (1H, m, CH), 10.62 (1H, m, CH), 10.12 (1H, s, CH), 10.06 (1H, m, CH), 6.22 (2H, m, CH—O), 4.54-4.15 (8H, m, CH$_2$—O ester, CH$_2$—CH$_2$—C=O), 4.10 (4H, m, ether O—CH$_2$—CH$_2$), 3.86-3.42 (12H, m, CH$_3$), 3.31 (4H, m, CH$_2$—CH$_2$—C=O), 2.62 (4H, m, CF$_3$—CH$_2$—CH$_2$ ether), 2.47-2.21 (10H, m, ester O—CH$_2$—CH$_2$, CH$_3$), −3.66 (2H, br, NH); $^{13}$C NMR (CDCl$_3$, 100 MHz) δ 172.80 (C=O), 146.73-140.77, 139.44, 138.42, 137.53, 137.09 (C pyrrole CH$_2$=CH), 123.44-112.12 (4C, m, CF$_2$, CF$_3$), 98.62, 98.34, 97.16, 96.45 (CH$_2$=CH), 74.17 (m, J$_{C,F}$=72.32, 49.96 CH—O), 61.01 (m, ether CH$_2$—O×2), 56.58 (m, CH$_2$—O ester×2), 37.21, 36.88 (CH$_2$—C=O), 31.91 (m, ether CH$_2$—CF$_3$), 30.27 (m, ester CH$_2$—CF$_3$), 25.46, 25.35 (CH$_3$), 21.76 (CH$_2$—CH$_2$), 12.32, 11.88, 11.63, 11.47 (CH$_3$) $^{19}$F NMR (CDCl$_3$, 376 MHz) −85.69-85.80 (12F, m, CF$_3$), −116.99 (4F, m, CF$_2$), −117.40 (4F, m, CF$_2$). ESI Calcd for C$_{50}$H$_{51}$F$_{20}$N$_4$O$_6$: 1183.35 [M+H$^+$], found m/z 1183.35 [M+H$^+$]. HRMS Calcd for C$_{50}$H$_{51}$F$_{20}$N$_4$O$_6$: 1183.3489 [M+H$^+$], found m/z 1183.3488 [M+H$^+$].

g) Synthesis of Fluoro-Tetrasubstituted CF4PPIXCF4 (Compound 43g) (SD423 CF3CF2CF2CF2CH2CH2OH)

200 mg of BrPPIX are dissolved in 1.3 ml of 1H,1H,2H, 2H-Perfluorohexan-1-ol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 190 mg of pure 43g in 63% yield.

$^1$H NMR (CDCl$_3$, 400 MHz) δ 10.57-10.41 (2H, m, CH), 10.12-10.03 (2H, m, CH), 6.14 (2H, m, CH—O), 4.36 (8H, m, CH$_2$—O ester CH$_2$—CH$_2$—C=O), 4.00 (4H, m, ether O—CH$_2$—CH$_2$), 3.77-3.54 (12H, m, CH$_3$), 3.30 (4H, m, CH$_2$—CH$_2$—C=O), 2.28 (4H, m, CF$_3$—CH$_2$—CH$_2$ ether), 2.56 (4H, m, CF$_3$—CH$_2$—CH$_2$ ether), 2.41-2.14 (10H, m, CH$_3$ ester O—CH$_2$—CH$_2$), −3.72 (2H, br, NH); $^{13}$C NMR (CDCl$_3$, 100 MHz) δ 172.68 (C=O), 137.35, 137.06 (C pyrrole CH$_2$=CH), 98.61, 98.38, 97.02, 96.45 (CH$_2$=CH), 74.02 (CH—O), 61.26 (m, ether CH$_2$—O×2), 56.58 (m, CH$_2$—O ester×2), 36.80 (CH$_2$—C=O), 31.92, 31.85 (m, ether CH$_2$—CF$_3$), 30.23 (m, ester CH$_2$—CF$_3$), 26.27, 25.29 (CH$_3$), 21.67 (CH$_2$—CH$_2$), 11.66, 11.53, 11.41 (CH$_3$); $^{19}$F NMR (CDCl$_3$, 376 MHz) −81.18 (12F, m, CF$_3$), −114.02 (8F, m, CF$_2$), −124.66 (8F, m, CF$_2$), −126.16 (8F, m, CF$_2$). ESI Calcd for C$_{58}$H$_{50}$F$_{36}$N$_4$O$_6$: 1583.32 [M+H$^{30}$], found m/z 1583.33 [M+H$^+$]. HRMS Calcd for C$_{58}$H$_{50}$F$_{36}$N$_4$O$_6$: 1583.3234 [M+H$^{30}$], found m/z 1583.3258 [M+H$^+$].

h) Synthesis of Fluoro-Tetrasubstituted CF6PPIXCF6 (Compound 43 h) (SD407/SD380 CF3(CF2)$_5$CH2CH2OH)

100 mg of BrPPIX are dissolved in 2 ml of 1H,1H,2H, 2H,2H-Perfluorooctan-1-ol and the resulting mixture is stirred during 16 hours. Then the reaction mixture is diluted with EtOAc and washed twice with a saturated solution of NaHCO$_3$, dried over Na$_2$SO$_4$ dried under high vacuum to afford 165 mg of pure 43 h in quantitative yield.

$^1$H NMR (CDCl$_3$, 400 MHz) δ 10.56 (1H, d, J=2.92 Hz CH), 10.52 (1H, d, J=10.81 Hz CH), 10.13, 10.11 (2H, s, CH), 6.14 (2H, m, CH—O), 4.43 (4H, t, J=7.62 Hz CH$_2$—CH$_2$—C=O), 4.33 (4H, dd, J=6.79, 14.27 Hz CH$_2$—O ester), 4.00 (4H, m, ether O—CH$_2$—CH$_2$), 3.74-3.58 (12H, m, CH$_3$), 3.31 (4H, t, J=7.62 Hz CH$_2$—CH$_2$—C=O), 2.73 (4H, m, CF$_3$—CH$_2$—CH$_2$ ether), 2.34-2.11 (10H, m, ester O—CH$_2$—CH$_2$, CH$_3$), −3.66 (2H, br, NH); $^{13}$C NMR (CDCl$_3$, 100 MHz) δ 172.86 (C=O), 139.25, 138.44, 137.76, 137.19 C pyrrole (CH$_2$=CH), 124.93 (dd, J$_{C,F}$=276.9, 59.8 Hz CF$_3$), 98.78, 98.43, 97.20, 96.46 (CH$_2$=CH), 74.18 (CH—O), 61.41 (ether CH$_2$—O×2), 56.51, CH$_2$—O ester×2), 36.97, 36.90 (CH$_2$—C=O), 31.89 (ether CH$_2$—CF$_3$), 30.32 (m, ester CH$_2$—CF$_2$), 25.47, 25.36 (CH$_3$), 21.84 (CH$_2$—CH$_2$), 11.85, 11.70, 11.56, 11.54 (CH$_3$)$^{19}$F NMR (CDCl$_3$, 376 MHz) −80.92 (12F, m, CF$_3$), −113.31 (4F, m, CF$_2$), −113.89 (4F, m, CF$_2$), −122.06 (8F, m, CF$_2$), −123.04 (8F, br s, CF$_2$), −123.79 (8F, br s, CF$_2$), 126.31 (8F, br s, CF$_2$). ESI Calcd for C$_{66}$H$_{51}$F$_{52}$N$_4$O$_6$: 1983.30 [M+H$^+$], found m/z 1983.30 [M+H$^+$]. HRMS Calcd for C$_{66}$H$_{51}$F$_{52}$N$_4$O$_6$: 236.2978 [M+H$^+$], found m/z 1983.2969 [M+H$^+$].

9.2.3. Hydrolysis of Esters (Saponification): Synthesis of Disubstituted PPIX Analogues 44a to 44f a) Synthesis of Disubstituted C4PPIX (Compound 44a) (SD435 Butanol)

75 mg of C4PPIXC4-43a (1 eq, 0.091 mmol) and 44 mg of LiOH (20 eq, 1.82 mmol) are dissolved in a mixture of THF (3 ml) and water (1 ml). The resulting mixture is stirred during 16 hours, the THF is removed in vacuo, and then 1 ml of glacial acetic acid is added to the remaining mixture and filtrated. The crude is dissolved in glacial acetic acid, diluted with DCM washed twice with a brine solution and dried over $Na_2SO_4$ to afford 64 mg of pure product in quantitative yield.

$^1$H NMR ($CDCl_3$, 400 MHz) δ 10.66 (1H, d, J=1.98 Hz CH), 10.63, 9.99, 9.86 (3H, s, CH), 6.12 (2H, m, CH—O), 4.38 (2H, br, $CH_2$—$CH_2$—C=O), 4.13 (2H, br, $CH_2$—$CH_2$—C=O), 3.90-3.59 (12H, m, $CH_3$, ether O—$CH_2$—$CH_2$), 3.45 (3H, s, $CH_3$), 3.39-3.19 (4H, m, $CH_2$—$CH_2$), 2.28 (6H, m, $CH_3$), 1.80 (4H, m, ether O—$CH_2$—$CH_2$), 1.45 (4H, m, $CH_2$), 0.87 (6H, m, $CH_3$); $^{13}$C NMR ($CDCl_3$, 100 MHz) δ 180.08, 180.05 (C=O), 145.60-136.06 (C pyrrole $CH_2$=CH), 99.14, 98.79, 96.88, 95.47 ($CH_2$=CH), 73.45 (CH—O), 69.44 ($CH_2$—O×2), 37.62, 37.55 ($CH_2$—C=O), 32.54 (ether O—$CH_2$—$CH_2$), 25.62, 25.57 ($CH_3$×2), 22.03, 21.93 ($CH_2$—$CH_2$—C=O), 19.74 ($CH_2$) 14.12, 14.09 ($CH_2$—$CH_3$), 11.80, 11.74, 11.69, 11.54 ($CH_3$) ESI Calcd for $C_{42}H_{53}N_4O_6$: 709.40 [M-H$^+$], found m/z 709.40 [M-H$^+$] HRMS Calcd for $C_{42}H_{53}N_4O_6$: 709.3965 [M-H$^+$], found m/z 709.3967 [M-H$^+$].

b) Synthesis of Disubstituted C6PPIX (Compound 44b) (SD421.1 Hexanol)

62 mg of C6PPIXC6-43b (1 eq, 0.066 mmol) and 32 mg of LiOH (20 eq, 1.32 mmol) are dissolved in a mixture of THF (3 ml) and water (1 ml). The resulting mixture is stirred during 16 hours, the THF is removed in vacuo, then 4 ml of a mixture of glacial acetic acid (1 ml) and water (3 ml) is added to the remaining mixture and filtrated, then the crude is dissolved in 50 ml of EtOAc and washed twice with HCl 0.1N, twice with a brine solution and dried over $Na_2SO_4$ to afford 50 mg of pure 44b in quantitative yield.

$^1$H NMR ($CDCl_3$, 400 MHz) δ 10.67 (1H, s, CH), 10.64 (1H, d, J=2.71 Hz CH), 10.10, (2H, s, CH), 6.11 (2H, m, CH—O), 4.45 (4H, m, $CH_2$—$CH_2$—C=O), 3.82-3.54 (16H, m, $CH_3$, ether O—$CH_2$—$CH_2$), 3.38 (4H, m, $CH_2$—$CH_2$), 2.26 (6H, m, $CH_3$), 1.78 (4H, m, ether O—$CH_2$—$CH_2$), 1.50-1.07 (12H, m, $CH_2$), 0.73 (6H, m, $CH_3$); $^{13}$C NMR ($CDCl_3$, 100 MHz) δ 179.81 (C=O), 139.60, 138.06, 136.79, (C pyrrole $CH_2$=CH), 99.25, 98.89, 97.01, 95.71 ($CH_2$=CH), 73.44 (CH—O), 69.76 ($CH_2$—O×2), 37.62 ($CH_2$—C=O), 30.43 (ether O—$CH_2$—$CH_2$), 26.26 ($CH_2$), 25.63 ($CH_3$×2), 22.69, 22.17 ($CH_2$), 14.06, 14.04 ($CH_2$—$CH_3$), 11.89, 11.77, 11.71 ($CH_3$). ESI Calcd for $C_{46}H_{61}N_4O_6$: 765.46 [M-H$^+$], found m/z 765.46 [M-H$^+$] HRMS Calcd for $C_{46}H_{61}N_4O_6$: 765.4591 [M-H$^+$], found m/z 765.4591 [M-H$^+$].

c) Synthesis of Disubstituted C8PPIX (Compound 44c) (SD421.2 Octanol)

54 mg of C8PPIXC8-43c (1 eq, 0.052 mmol) and 25 mg of LiOH (20 eq, 1.03 mmol) are dissolved in a mixture of THF (3 ml) and water (1 ml). The resulting mixture is stirred during 16 hours, the THF is removed in vacuo, then 4 ml of a mixture glacial acetic acid (1 ml) and water (3 ml) is added to the remaining mixture and filtrated, then the crude is dissolved in 50 ml of EtOAc and washed twice with HCl 0.1N, twice with a brine solution dried over $Na_2SO_4$ to afford 42 mg of pure 44c in quantitative yield.

$^1$H NMR ($CDCl_3$, 400 MHz) δ 10.69, 10.66, 10.09 (4H, s, CH), 6.11 (2H, m, CH—O), 4.39 (4H, m, $CH_2$—$CH_2$—C=O), 3.85-3.51 (16H, m, $CH_3$, ether O—$CH_2$—$CH_2$), 3.34 (4H, m, $CH_2$—$CH_2$—C=O), 2.25 (6H, s, $CH_3$), 1.82 (4H, m, ether O—$CH_2$—$CH_2$), 1.51-1.02 (20H, m, $CH_2$), 0.74 (6H, m, $CH_3$); $^{13}$C NMR ($CDCl_3$, 100 MHz) δ 179.43 (C=O), 140.86, 139.43, 138.37, 136.06 (C pyrrole $CH_2$=CH), 99.49, 99.05, 97.26, 96.25 ($CH_2$=CH), 73.44 (CH—O), 69.85 ($CH_2$—O×2), 37.43 ($CH_2$—C=O), 31.86 ($CH_2$), 30.47 (ether O—$CH_2$—$CH_2$), 29.85, 29.64, 29.51, 29.36, 29.35 ($CH_2$), 26.59 ($CH_2$), 25.59 ($CH_3$×2), 22.84, 22.70, 22.68, 22.07, 22.00 ($CH_2$) 14.26, 14.12 ($CH_2$—$CH_3$), 11.92, 11.81, 11.75 ($CH_3$) ESI Calcd for $C_{50}H_{69}N_4O_6$: 821.52 [M-H$^+$], found m/z 821.52 [M-H$^+$] HRMS Calcd for $C_{46}H_{61}N_4O_6$: 821. ESI C5217 [M-H$^+$], found m/z 821.5217 [M-H$^+$].

d) Synthesis of Disubstituted C10PPIX (Compound 44d) (SD443 Decanol)

31 mg of C10PPIXC10-43d (1 eq, 0.027 mmol) and 12.8 mg of LiOH (20 eq, 0.53 mmol) are dissolved in a mixture of THF (3 ml) and water (1 ml). The resulting mixture is stirred 16 hours, the THF is removed in vacuo, then 4 ml of a mixture glacial acetic acid (1 ml) and water (3 ml) is added to the remaining mixture and filtrated, washed with water and dissolved in a mixture of AcOEt and methanol, dried in vacuo and purified over LH20 (MeOH/DCM 1/2) to afford 18 mg of pure 44d in 76.0% yield.

$^1$H NMR ($CDCl_3$, 400 MHz) δ 10.60 (2H, s, CH), 10.11, 10.00 (2H, s, CH), 6.06 (2H, m, CH—O), 4.33 (4H, m, $CH_2$—$CH_2$), 3.81-3.39 (16H, m, $CH_3$, ether O—$CH_2$—$CH_2$), 3.26 (4H, t, J=7.61 Hz $CH_2$—$CH_2$—C=O), 2.20 (6H, d, J=6.65 Hz, $CH_3$), 1.74 (4H, m, ether O—$CH_2$—$CH_2$), 1.47-0.97 (44H, m, $CH_2$), 0.77 (12H, m, $CH_3$); $^{13}$C NMR ($CDCl_3$, 100 MHz) δ 180.01 (C=O), 145.17-134.89 (C pyrrole $CH_2$=CH), 99.05, 98.65, 96.84, 95.81 ($CH_2$=CH), 73.38 (CH—O), 69.69 ($CH_2$—O×2), 38.82, 37.86 ($CH_2$—C=O), 31.90 (ether O—$CH_2$—$CH_2$), 30.70, 30.42, 29.84, 29.65, 29.62, 29.58, 29.32, 26.54, ($CH_2$), 25.58 ($CH_3$×2), 22.83, 22.69, 22.17 ($CH_2$), 14.25, 14.14, 13.80, 14.19 ($CH_2$—$CH_3$), 11.75, 11.65 ($CH_3$) ESI calcd for $C_{54}H_{77}N_4O_6$: 877.58 [M-H$^+$], found m/z 877.58 [M-H$^+$] HRMS Calcd for $C_{54}H_{77}N_4O_6$: 877.5843 [M-H$^+$], found m/z 877.5839 [M-H$^+$].

e) Synthesis of Fluoro-Disubstituted CF1PPIX (Compound 44e) (SD417.2 CF3CH2CH2OH)

45 mg of CF1PPIXCF1-43e (1 eq, 0.045 mmol) and 22 mg of LiOH (20 eq, 0.90 mmol) are dissolved in a mixture of THF (3 ml) and water (1 ml). The resulting mixture is stirred during 2H 30 min, the THF is removed in vacuo, then 4 ml of a mixture glacial acetic acid (1 ml) and water (3 ml) is added to the remaining mixture and filtrated, the crude is dissolved in 30 ml of EtOH and dried under high vacuum to afford 35 mg of pure 44e in quantitative yield.

$^1$H NMR ($CDCl_3$, 400 MHz) δ 10.54, 10.50, 9.93, 9.81 (4H, s, CH), 6.10 (2H, m, CH—O), 4.27 (2H, br, $CH_2$—$CH_2$—C=O), 3.95 (6H, m, ether O—$CH_2$—$CH_2CH_2$—$CH_2$—C=O), 3.76-3.52 (9H, m, $CH_3$), 3.38 (3H, m, $CH_3$), 3.30-3.06 (4H, m, $CH_2$—$CH_2$—C=O), 2.56 (4H, m, $CF_3$—$CH_2$—$CH_2$ ether), 2.25 (6H, m, $CH_3$); $^{13}$C NMR ($CDCl_3$, 100 MHz) δ 179.73 (C=O), 142.22-135.43 (C pyrrole $CH_2$=CH), 126.44 (q, $J_{C,F}$=276.9 Hz $CF_3$), 98.76, 98.41, 97.01, 95.81 ($CH_2$=CH), 74.19, 73.97 (CH—O), 62.45 ($CH_2$—O×2), 37.53 ($CH_2$—C=O), 34.98 (q, $J_{C,F}$=28.54 Hz ether $CH_2$—$CF_3$), 25.41, 25.34 ($CH_3$) 21.95, 21.73 ($CH_2$—$CH_2$), 12.25, 11.70, 11.63, 11.43 ($CH_3$) $^{19}$F NMR ($CDCl_3$, 376 MHz) −64.44 (6F, m, $CF_3$), ESI Calcd for $C_{40}H_{43}F_6N_4O_6$: 789.31 [M−H$^+$], found m/z 789.31 [M−H$^+$]. HRMS Calcd $C_{40}H_{43}F_6N_4O_6$: 789.3087 [M−H$^+$], found m/z 789.3121 [M−H$^+$].

f) Synthesis of Fluoro-Disubstituted CF2PPIX (Compound 440 (SD422.1 CF3CF2CH2CH2OH)

74 mg of CF2PPIXCF2-43f (1 eq, 0.063 mmol) and 30 mg of LiOH (20 eq, 1.25 mmol) are dissolved in a mixture of THF (3 ml) and water (1 ml). The resulting mixture is stirred during 2H 30 min, the THF is removed in vacuo, then 4 ml of a mixture glacial acetic acid (1 ml) and water (3 ml) is added to the remaining mixture and filtrated, then the crude is dissolved in 50 ml of EtOAc and washed twice with HCl 0.1 N, dried over Na$_2$SO$_4$ to afford 56 mg of pure 44f in quantitative yield.

$^1$H NMR (CDCl$_3$, 400 MHz) δ 10.54 (1H, d, J=3.15 Hz CH), 10.49, 9.97, 9.82 (3H, s, CH), 6.13 (2H, m, CH—O), 4.28 (2H, br, CH$_2$—O ether), 4.13-3.92 (6H, m, ether O—CH$_2$—CH$_2$, CH$_2$—CH$_2$—C=O), 3.76-3.55 (9H, m, CH$_3$), 3.49-3.11 (7H, m, CH$_3$—CH$_2$, CH$_2$—C=O), 2.57 (4H, m, CF$_3$—CF$_2$—CH$_2$—CH$_2$ ether), 2.34-2.27 (6H, m, CH$_3$); $^{13}$C NMR (CDCl$_3$, 100 MHz) δ 179.46 (C=O), 144.78-133.22 (C pyrrole CH$_2$=CH), 98.72, 98.20, 96.92, 95.49 (CH$_2$=CH), 74.15, (CH—O), 61.47 (ether CH$_2$—O× 2), 37.45, 37.26 (CH$_2$—C=O), 31.92 (m, ether CH$_2$—CF$_3$), 25.43, 25.32 (CH$_3$), 21.79 (CH$_2$—CH$_2$), 11.64, 11.53, 11.08 (CH$_3$) $^{19}$F NMR (CDCl$_3$, 376 MHz) −85.74 (6F, m, CF$_3$), −117.02 (4F, m, CF$_2$). ESI Calcd for $C_{42}H_{43}F_{10}N_4O_6$: 889.30 [M−H$^+$], found m/z 889.30 [M−H$^+$]. HRMS Calcd $C_{40}H_{43}F_6N_4O_6$: 889.3023 [M−H$^+$], found m/z 889.3018 [M−H$^+$].

g) Synthesis of Fluoro-Disubstituted CF4PPIX (Compound 44g) (SD424 CF3CF2CF2CF2CH2CH2OH)

100 mg of CF4PPIXCF4-43g (1 eq, 0.063 mmol) and 30 mg of LiOH (20 eq, 1.26 mmol) are dissolved in a mixture of THF (3 ml) and water (1 ml). The resulting mixture is stirred during 1 hour, then the THF is removed in vacuo, then 4 ml of a mixture glacial acetic acid (1 ml) and water (3 ml) is added to the remaining mixture and filtrated, then the crude is dissolved in 50 ml of EtOAc and washed twice with HCl 0.1 N, dried over Na$_2$SO$_4$ to afford 63 mg of pure 44g in 92.8% yield.

$^1$H NMR (CDCl$_3$, 400 MHz) δ 10.56 (1H, d, J=4.38 Hz CH), 10.45 (1H, d, J=9.23 Hz CH), 9.85, 9.47 (2H, s, CH), 6.13 (2H, m, CH—O), 4.08 (8H, m, CH$_2$—O ether CH$_2$—CH$_2$—C=O), 3.82-3.45 (12H, m, CH$_3$), 3.15 (4H, m, CH$_2$—CH$_2$—C=O), 2.59 (4H, m, CF$_3$—CH$_2$—CH$_2$ ether), 2.31 (6H, m, CH$_3$); $^{13}$C NMR (CDCl$_3$, 100 MHz) δ 179.54 (C=O), 139.44, 136.07 (C pyrrole CH$_2$=CH), 98.28, 97.01 (CH$_2$=CH), 74.18 (CH—O), 61.46 (ether CH$_2$—O×2), 37.30 (CH$_2$—C=O), 32.08 (ether CH$_2$—CF$_3$), 26.08, 25.39 (CH$_3$), 22.84 (CH$_2$—CH$_2$), 11.69, 11.56, 11.30 (CH$_3$) $^{19}$F NMR (CDCl$_3$, 376 MHz) −81.09 (12F, m, CF$_3$), −113.44 (8F, br, CF$_2$), −124.58 (8F, br, CF$_2$), −126.04 (8F, m, CF$_2$). ESI Calcd for $C_{46}H_{43}F_{18}N_4O_6$: 1089.29 [M−H$^+$], found m/z 1089.28 [M−H$^+$]. HRMS Calcd $C_{46}H_{43}F_{18}N_4O_6$: 1089.2895 [M−H$^+$], found m/z 1089.2895 [M−H$^+$].

h) Synthesis of Fluoro-Disubstituted CF6PPIX (Compound 44 h) (SD422.2/SD380 depro CF3(CF2)5CH2CH2OH)

65 mg of CF6PPIXCF6-43 h (1 eq, 0.033 mmol) and 15 mg of LiOH (20 eq, 0.65 mmol) are dissolved in a mixture of THF (3 ml) and water (1 ml). The resulting mixture is stirred during 2 h30, the THF is removed in vacuo, then 4 ml of a mixture glacial acetic acid (1 ml) and water (3 ml) is added to the remaining mixture and filtrated, then the crude is dissolved in 50 ml of EtOAc and washed twice with HCl 0.1N, dried over Na$_2$SO$_4$ to afford 40 mg of pure 44 h in 95.2% yield.

$^1$H NMR (CDCl$_3$, 400 MHz) δ 10.56 (1H, d, J=3.0 Hz CH), 10.48 (1H, d, J=11.20 Hz CH), 10.11, 10.06 (2H, s, CH), 6.13 (2H, m, CH—O), 4.39 (4H, m, CH$_2$—CH$_2$—C=O), 4.03 (4H, m, ether O—CH$_2$—CH$_2$), 3.72-3.49 (12H, m, CH$_3$), 3.31 (4H, m, CH$_2$—CH$_2$—C=O), 2.58 (4H, m, CF$_3$—CH$_2$—, CH$_2$ ether), 2.24 (6H, d, J=5.08 Hz CH$_3$); $^{13}$C NMR (CDCl$_3$, 100 MHz) δ 179.24 (C=O), 124.93 (dd, $J_{C,F}$=276.9, 59.8 Hz CF$_3$), 98.88, 97.19, 96.09 (CH$_2$=CH), 74.17 (CH—O), 61.42 (ether CH$_2$—O×2), 37.53, 36.68 (CH$_2$—C=O×2), 32.08 (ether CH$_2$—CF$_3$), 25.44, 25.37 (CH$_3$), 22.09 (CH$_2$—CH$_2$), 11.70, 11.55 (CH$_3$) $^{19}$F NMR (CDCl$_3$, 376 MHz) −80.85 (6F, m, CF$_3$), −113.30 (4F, m, CF$_2$), −121.97 (4F, br s, CF$_2$), −122.97 (4F, br s, CF$_2$), −123.71 (4F, br s, CF$_2$), −126.23 (4F, br s, CF$_2$). ESI Calcd for $C_{50}H_{43}F_{26}N_4O_6$: 1289.28 [M−H$^+$], found m/z 1289.28 [M−H$^+$]. HRMS Calcd $C_{50}H_{43}F_{26}N_4O_6$: 1289.2767 [M−H$^+$], found m/z 1289.2750 [M−H$^+$].

9.2.4. Coupling of PEG Moieties: Amphiphilic PPIX Analogues 45a to 45f a) Synthesis of PPIXPEG550 (compound 46) (SD431 PPIXPeg)

50 mg of PPIX (1 eq, 0.089 mmol), 46 mg of DCC (2.5 eq, 0.23 mmol) and 30 mg of HOBt (2.5 eq, 0.23 mmol) were dissolved in 5 ml of DMF, after 5 min of stirring 153 mg of 1-amino-ω-methoxy-PEG550 (PEGamine) 41 (3 eq, 0.27 mmol) are added, the resulting mixture is stirred during 60 hours; then the DMF is removed under high vacuum and the crude is purified over LH20 in DCM/MeOH 1/1 to afford 75 mg of pure 46 in 50.3% yield.

$^1$H NMR (CDCl$_3$, 400 MHz) δ 9.80, 9.76, 9.73, 9.59 (4H, s, CH), 8.11 (2H, m, CH=CH$_2$), 6.93 (1H, br, NH), 6.89 (1H, br, NH), 6.29 (4H, dd, J=5.97, 17.82 Hz CH=CH$_2$), 6.14 (4H, dd, J=3.85, 11.37 Hz CH=CH$_2$), 4.22 (4H, br, J=6.57 Hz CH$_2$—CH$_2$—C=O), 3.74-3.17 (86H, m, CH$_2$ PEG CH$_3$O—CH$_3$), 3.10 (8H, m, NH—CH$_2$CH$_2$—O), 2.97 (4H, m, CH$_2$—CH$_2$—C=O), 2.74 (8H, m, CH$_2$—O), 2.08 (8H, m, CH$_2$—O); $^{13}$C NMR (CDCl$_3$, 100 MHz) δ 172.98, 172.96 (C=O), 138.96, 136.12 (C pyrrole CH$_2$=CH), 130.25 (CH=CH$_2$), 120.62 (CH=CH$_2$), 97.37, 96.83, 96.77, 96.51 (CH$_2$=CH), 74.17 (CH—O), 71.99-69.07 (CH$_2$ PEG), 59.07 (O—CH$_3$), 39.68 (CH$_2$—C=O), 39.14 (CH$_2$—NH), 23.01 (CH$_2$—CH$_2$), 12.69, 12.65, 11.55, 11.49 (CH$_3$).

b) Synthesis of Amphiphilic C4PPIXPEG550 (Compound 45a) (SD436 Butanol)

32 mg of C4PPIX-44a (1 eq, 0.045 mmol), 23 mg of DCC (2.5 eq, 0.113 mmol) and 15 mg of HOBt (2.5 eq, 0.113 mmol) were dissolved in 3 ml of DMF, after 5 min of stirring 78 mg of PEGamine 41 (3 eq, 0.27 mmol) is added, the resulting mixture is stirred during 60 hours; then the DMF is removed under high vacuum and the crude is purified over LH20 in DCM/MeOH 1/1 to afford 32 mg of pure 45a in 39.0% yield.

$^1$H NMR (CDCl$_3$, 400 MHz) δ 10.61, 10.60, 10.25, 10.10 (4H, s, CH), 7.04 (1H, br, NH), 6.98 (1H, br, NH), 6.11 (2H, m, CH—O), 4.44 (4H, m, CH$_2$—CH$_2$—C=O), 3.85-3.26 (101H, m, CH$_3$, ether O—CH$_2$—, CH$_2$—O), 3.26-3.08 (16H, m, CH$_2$—O, O—CH$_3$, CH$_2$—NH, CH$_2$—CH$_2$—C=O), 2.95 (8H, m, CH$_2$—O), 2.35 (8H, m, CH$_2$—O), 2.24 (6H, d, J=6.64 Hz CH$_3$), 1.78 (4H, m, ether O—CH$_2$—CH$_2$), 1.42 (4H, m, CH$_2$), 0.84 (6H, m, CH$_3$); $^{13}$C NMR (CDCl$_3$, 100 MHz) δ 173.11 (C=O), 140.53-136.44 (C pyrrole CH$_2$=CH), 98.73, 98.54, 97.31, 96.74 (CH$_2$=CH), 73.43 (CH—O), 72.07-69.37 (CH$_2$—O), 59.14, 59.11 (O—CH$_3$), 39.93 (CH$_2$—C=O), 39.33 (CH$_2$—NH), 32.52 (ether O—CH$_2$—CH$_2$), 25.63 (CH$_3$×2), 23.26 (CH$_2$—CH$_2$—C=O), 19.72 (CH$_2$) 14.08 (CH$_2$—CH$_3$), 11.82, 11.79, 11.70 (CH$_3$).

c) Synthesis of Amphiphilic C6PPIXPEG550 (Compound 45b) (SD428 Hexanol)

34 mg of C6PPIX-44b (1 eq, 0.044 mmol), 23 mg of DCC (2.5 eq, 0.110 mmol) and 14 mg of HOBt (2.5 eq, 0.110 mmol) were dissolved in 3 ml of DMF, after 5 min of stirring 77 mg of PEGamine 41 (3 eq, 0.27 mmol) are added, the resulting mixture is stirred during 24 hours; then the DMF is removed under high vacuum and the crude is purified over LH20 in DCM/MeOH 1/1 to afford 51 mg of pure 45b in 62.2% yield.

$^1$H NMR (CDCl$_3$, 400 MHz) δ 10.62, 10.59, 10.26, 10.10 (4H, s, CH), 7.07 (2H, br, NH), 6.11 (2H, m, CH—O), 4.44 (4H, m, CH$_2$—CH$_2$—C=O), 3.78-3.29 (93H, m, CH$_3$, O—CH$_2$, ether O—CH$_2$—CH$_2$), 3.27-3.07 (16H, m, CH$_2$—O, CH$_2$—NH, CH$_2$—CH$_2$—C=O), 2.91 (8H, m, CH$_2$—O), 2.42 (8H, m, CH$_2$—O), 2.24 (6H, m, CH$_3$), 1.77 (4H, m, ether O—CH$_2$—CH$_2$), 1.52-1.10 (12H, m, CH$_2$), 0.74 (6H, m, CH$_3$); $^{13}$C NMR (CDCl$_3$, 100 MHz) δ 173.13 (C=O), 140.55-136.40 (C pyrrole CH$_2$=CH), 98.79, 98.51, 97.33, 96.74 (CH$_2$=CH), 73.41 (CH—O), 72.04-69.38 (CH$_2$—O), 59.11 (O—CH$_3$), 39.95 (CH$_2$—C=O), 39.35 (CH$_2$—NH), 31.87, 31.85 (CH$_2$), 30.42 (ether O—CH$_2$—CH$_2$), 26.26 (CH$_2$), 25.66, 25.63 (CH$_3$×2), 23.30, 22.68 (CH$_2$) 14.07, 14.04 (CH$_2$—CH$_3$), 11.86, 11.80, 11.76, 11.69 (CH$_3$) ESI Calcd for C$_{13}$H$_{18}$NO$_3$: 236.13 [M+H$^+$], found m/z 236.13 [M+H$^+$].

d) Synthesis of Amphiphilic C8PPIXPEG550 (Compound 45c) (SD429 Octanol)

25 mg of C8PPIX-44c (1 eq, 0.032 mmol), 23 mg of DCC (2.5 eq, 0.075 mmol) and 14 mg of HOBt (2.5 eq, 0.075 mmol) were dissolved in 3 ml of DMF, after 5 min of stirring 57 mg of PEGamine 41 (3 eq, 0.099 mmol) are added, the resulting mixture is stirred during 24 hours; then the DMF is removed under high vacuum and the crude is purified over LH20 in DCM/MeOH 1/1 to afford 20 mg of pure 45c in 32.2% yield.

$^1$H NMR (CDCl$_3$, 400 MHz) δ 10.62, 10.60, 10.25, 10.10 (4H, s, CH), 7.01 (1H, br, NH), 6.10 (2H, m, CH—O), 4.44 (4H, m, CH$_2$—CH$_2$—C=O), 3.86-3.30 (87H, m, CH$_3$, O—CH$_2$, ether O—CH$_2$—CH$_2$), 3.28-3.18 (16H, m, CH$_2$—O, CH$_3$—OCH$_2$—NH, CH$_2$—CH$_2$—C=O), 2.92 (8H, m, CH$_2$—O), 2.44 (6H, m, CH$_2$—O), 2.24 (6H, d, J=6.34 Hz CH$_3$), 1.77 (4H, m, ether O—CH$_2$—CH$_2$), 1.51-1.02 (20H, m, CH$_2$), 0.76 (6H, m, CH$_3$); $^{13}$C NMR (CDCl$_3$, 100 MHz) δ 173.14 (C=O), 144.71-137.04 (C pyrrole CH$_2$=CH), 98.83, 98.59, 97.35, 96.79 (CH$_2$=CH), 73.43 (CH—O), 72.06-69.41 (CH$_2$—O), 59.13 (O—CH$_3$), 39.94, (CH$_2$—C=O), 39.34 (CH$_2$—NH), 31.86, 31.03, 30.46 (CH$_2$), 30.46 (ether O—CH$_2$—CH$_2$), 29.83, 29.63, 29.49, 29.34 (CH$_2$), 26.59 (CH$_2$), 25.65 (CH$_3$×2), 23.30, 22.82, 22.70 (CH$_2$) 14.24, 14.11 (CH$_2$—CH$_3$), 11.87, 11.77, 11.71 (CH$_3$).

e) Synthesis of Amphiphilic C10PPIXPEG550 (Compound 45d) (SD448 Decanol)

9 mg of C10PPIX-44d (1 eq, 0.010 mmol), 5 mg of DCC (2.5 eq, 0.026 mmol) and 3.5 mg of HOBt (2.5 eq, 0.026 mmol) were dissolved in 1 ml of DMF, after 5 min of stirring, a solution of 18 mg of PEGamine 41 (3 eq, 0.065 mmol) in 2 ml of DMF is added, the resulting mixture is stirred during 24 hours; then the DMF is removed under high vacuum and the crude is purified over LH20 in DCM/MeOH 2/1 to afford 13 mg of pure 45d in 65.0% yield.

$^1$H NMR (CDCl$_3$, 400 MHz) δ 10.61 (1H, d, J=3.10 Hz), 10.59 (1H, d, J=2.15 Hz), 10.26, 10.10 (2H, s, CH), 7.05 (2H, br, NH), 6.10 (2H, d, J=6.54 Hz CH—O), 4.44 (4H, m, CH$_2$—CH$_2$—C=O), 3.82-3.28 (77H, m, CH$_3$O—CH$_3$ ether O—CH$_2$—CH$_2$), 3.27-3.06 (14H, m, CH$_2$—OCH$_2$—NHCH$_2$—CH$_2$—C=O), 2.93 (8H, m, CH$_2$—O), 2.35 (8H, m, CH$_2$—O), 2.24 (6H, d, J=6.54 Hz CH$_3$), 1.78 (4H, m, ether O—CH$_2$—CH$_2$), 1.51-1.01 (28H, m, CH$_2$), 0.79 (6H, m, CH$_3$); $^{13}$C NMR (CDCl$_3$, 100 MHz) δ 173.15 (C=O), 98.75, 98.52, 97.35, 96.77 (CH$_2$=CH), 73.42 (CH—O), 72.05-69.38 (CH$_2$—O), 59.15 (O—CH$_3$), 39.98 (CH$_2$—C=O), 39.32 (CH$_2$—NH), 31.94 (CH$_2$), 30.46 (ether O—CH$_2$—CH$_2$), 39.63, 29.39, 29.36, 26.60 (CH$_2$), 25.69 (CH$_3$×2), 23.33, 22.73 (CH$_2$) 14.20 (CH$_2$—CH$_3$), 11.90, 11.84, 11.79, 11.73 (CH$_3$) ESI Calcd for C$_{13}$H$_{18}$NO$_3$: 236.13 [M+H$^+$], found m/z 236.13 [M+H$^+$].

f) Synthesis of Amphiphilic CF1PPIXPEG550 (Compound 45e) (SD425 CF3CH2CH2OH)

30 mg of CF1PPIX-44e (1 eq, 0.038 mmol), 17 mg of DCC (2.2 eq, 0.083 mmol) and 11 mg of HOBt (2.2 eq, 0.083 mmol) were dissolved in 3 ml of DMF, after 5 min of stirring 65 mg of PEGamine 41 (3 eq, 0.114 mmol) are added, the resulting mixture is stirred during 24 hours; then the DMF is removed under high vacuum and the crude is purified over LH20 in DCM/MeOH 1/1 to afford 47 mg of pure 45e in 65.3% yield.

$^1$H NMR (CDCl$_3$, 400 MHz) δ 10.53, 10.51, 10.27, 10.11 (4H, s, CH), 7.15 (1H, br, NH), 7.05 (1H, br, NH), 6.13 (2H, q, J=6.42 Hz CH—O), 4.44 (4H, m, CH$_2$—CH$_2$—C=O), 3.95 (4H, m, ether O—CH$_2$—CH$_2$), 3.77-3.28 (95H, m, CH$_2$—OCH$_2$O—CH$_3$), 3.27-3.10 (16H, m, CH$_2$—OCH$_2$—NHCH$_2$—CH$_2$—C=O), 2.93 (8H, m, CH$_2$—O), 2.58 (4H, m, CF$_3$—CH$_2$—CH$_2$ ether), 2.41 (6H, m, CH$_2$—O), 2.28 (6H, d, J=6.55 Hz CH$_3$); $^{13}$C NMR (CDCl$_3$, 100 MHz) δ 173.08 (C=O), 139.90-136.21 (C pyrrole CH$_2$=CH), 126.38 (q, J$_{C,F}$=278.4 Hz CF$_3$), 98.44, 98.21, 97.54, 96.95 (CH$_2$=CH), 74.08 (CH—O), 72.02-69.37 (CH$_2$—O), 62.45 (ether O—CH$_2$—CH$_2$×2), 59.09 (O—CH$_3$), 39.87, 39.81 (CH$_2$—C=O), 39.32 (CH$_2$—NH), 34.99 (q, J$_{C,F}$=28.39 Hz ether CH$_2$—CF$_3$), 25.43 (CH$_3$), 23.25, 23.18 (CH$_2$—CH$_2$—C=O), 11.76, 11.71, 11.67, 11.60 (CH$_3$) $^{19}$F NMR (CDCl$_3$, 376 MHz) −64.43 (6F, m, CF$_3$).

g) Synthesis of Amphiphilic CF2PPIXPEG550 (Compound 45Ø (SD430 CF3CF2CH2CH2OH)

25 mg of CF2PPIX-44f (1 eq, 0.028 mmol), 14 mg of DCC (2.5 eq, 0.070 mmol) and 11 mg of HOBt (2.5 eq, 0.070 mmol) were dissolved in 3 ml of DMF, after 5 min of stirring 65 mg of PEGamine 41 (3 eq, 0.084 mmol) are added, the resulting mixture is stirred during 60 hours; then the DMF is removed under high vacuum and the crude is purified over LH20 in DCM/MeOH 1/1 to afford 23 mg of pure 45f in 41.0% yield.

$^{1}$H NMR (CDCl$_3$, 400 MHz) δ 10.53 (1H, d, J=3.04 Hz CH), 10.50 (1H, d, J=3.84 Hz CH), 10.28, 10.11 (2H, s, CH), 7.08 (1H, br, NH), 6.99 (1H, br, NH), 6.14 (2H, m, CH—O), 4.43 (2H, br, CH$_2$—O ether), 4.02 (4H, m, ether O—CH$_2$—CH$_2$), 3.78-2.82 (116H, m, CH$_2$O, O—CH$_3$, CH$_3$, CH$_2$—CH$_2$—C=O), 2.46 (4H, m, CF$_3$—CH$_2$—CH$_2$ ether), 2.27 (6H, m, J=2.27 Hz CH$_3$); $^{13}$C NMR (CDCl$_3$, 100 MHz) δ 173.10 (C=O), 139.84-136.97 (C pyrrole CH$_2$=CH), 120.57, 117.10, 115.49 (m, CF$_2$, CF$_3$), 98.45, 98.12, 97.63, 97.03 (CH$_2$=CH), 74.17 (CH—O), 72.06-69.44 (CH$_2$ PEG), 61.51 (ether CH$_2$—O×2), 59.13 (O—CH$_3$), 39.94 (CH$_2$—C=O), 39.37 (CH$_2$—NH), 31.93 (t, J=20.96 Hz ether CH$_2$—CF$_3$), 25.41 (CH$_3$), 23.31, 23.25 (CH$_2$—CH$_2$), 11.81, 11.73, 11.63 (CH$_3$)$^{19}$F NMR (CDCl$_3$, 376 MHz) −85.74 (6F, m, CF$_3$), −117.03 (4F, m, CF$_2$).

h) Synthesis of Amphiphilic CF4PPIXPEG550 (Compound 45g) (SD427 CF3CF2CF2CF2CH2CH2OH)

40 mg of CF4PPIX-44g (1 eq, 0.037 mmol), 19 mg of DCC (2.5 eq, 0.092 mmol) and 12 mg of HOBt (2.5 eq, 0.092 mmol) were dissolved in 3 ml of DMF, after 5 min of stirring 64 mg of PEGamine 41 (3 eq, 0.110 mmol) is added, the resulting mixture is stirred during 60 hours; then the DMF is removed under high vacuum and the crude is purified over LH20 in DCM/MeOH 1/1 to afford 38 mg of pure 45g in 46.9% yield.

$^{1}$H NMR (CDCl$_3$, 400 MHz) δ 10.59-10.42 (2H, s, CH), 10.29-9.99 (2H, s, CH), 6.15 (2H, m, CH—O), 4.39 (8H, m, CH$_2$—CH$_2$—C=O), 4.01 (4H, m, ether O—CH$_2$—CH$_2$), 3.76-3.28 (110H, m, CH$_2$—O, CH$_3$, O—CH$_3$), 3.28-3.18 (16H, m, CH$_2$—O, CH$_2$—NH, CH$_2$—CH$_2$—C=O), 2.58 (4H, m, CF$_3$—CH$_2$—CH$_2$ ether), 2.41 (6H, m, CH$_2$—O), 2.28 (6H, m, CH$_3$); $^{13}$C NMR (CDCl$_3$, 100 MHz) δ 173.09 (C=O), 140.69-136-82 (C pyrrole CH$_2$=CH), 98.52, 98.09, 97.58, 97.00 (CH$_2$=CH), 74.19 (CH—O), 72.05-69.18 (CH$_2$—O), 61.43 (ether O—CH$_2$—CH$_2$×2), 59.11 (O—CH$_3$), 39.87 (CH$_2$—C=O), 39.37 (CH$_2$—NH), 32.00 (m, ether CH$_2$—CF$_2$), 26.57, 25.47 (CH$_3$), 22.81 (CH$_2$—CH$_2$), 11.77, 11.70, 11.55 (CH$_3$)$^{19}$F NMR (CDCl$_3$, 376 MHz) −81.08 (6F, m, CF$_3$), −113.44 (4F, br, CF$_2$), −124.57 (4F, br, CF$_2$), −126.01 (4F, m, CF$_2$).

i) Synthesis of Amphiphilic CF6PPIXPEG550 (Compound 45 h) (SD432 SD380 depro CF3(CF2)5CH2CH2OH)

28 mg of CF6PPIX-44 h (1 eq, 0.021 mmol), 11 mg of DCC (2.5 eq, 0.053 mmol) and 7 mg of HOBt (2.5 eq, 0.053 mmol) were dissolved in 3 ml of DMF, after 5 min of stirring 38 mg of PEGamine 41 (3 eq, 0.065 mmol) are added, the resulting mixture is stirred during 60 hours; then the DMF is removed under high vacuum and the crude is purified over LH20 in DCM/MeOH 1/1 to afford 19 mg of pure 45 h in 38.0% yield.

$^{1}$H NMR (CDCl$_3$, 400 MHz) δ 10.55 (1H, d, J=3.10 Hz), 10.48 (1H, d, J=14.26 Hz), 10.28, 10.12 (2H, s, CH), 6.14 (2H, m, CH—O), 4.44 (4H, m, CH$_2$—CH$_2$—C=O), 4.02 (4H, m, ether O—CH$_2$—CH$_2$), 3.74-3.29 (71H, m, CH$_2$—O, CH$_3$, O—CH$_3$), 3.28-3.10 (10H, m, CH$_2$—O, CH$_2$—NH, CH$_2$—CH$_2$—C=O), 2.97 (6H, m, CH$_2$—O), 2.55 (4H, m, CF$_3$—CH$_2$—CH$_2$ ether), 2.47 (6H, m, CH$_2$—O), 2.27 (6H, m, CH$_3$); $^{13}$C NMR (CDCl$_3$, 100 MHz) δ 173.11 (C=O), 140.25-137.01 (C pyrrole (CH$_2$=CH), 98.55, 98.16, 97.64, 97.04 (CH$_2$=CH), 74.21 (CH—O), 72.07-69.72 (CH$_2$—O), 61.44 (ether O—CH$_2$—CH$_2$), 59.15 (O—CH$_3$), 39.91 (CH$_2$—C=O), 39.37 (CH$_2$—NH), 32.08 (ether CH$_2$—CF$_3$), 25.52, 25.44 (CH$_3$), 22.84 (CH$_2$—CH$_2$), 11.84, 11.73, 11.56 (CH$_3$)$^{19}$F NMR (CDCl$_3$, 376 MHz) −80.83 (6F, m, CF$_3$), −113.29 (4F, m, CF$_2$), −121.95 (4F, br s, CF$_2$), −122.96 (4F, br s, CF$_2$), −123.67 (4F, br s, CF$_2$), −126.20 (4F, m, CF$_2$).

10. Experimental Data on dentriTAC

Tests were performed using the dentriTAC surfactants (see FIG. 2):
"F6diTAC5.4" (sample number SD28AD14 and SD104)
"F6diTAC10" (sample number SD165)
"F6diTAC7" (sample number SD149)
"DiF6diTAC6" (sample number SD347), with 2 fluor chains.

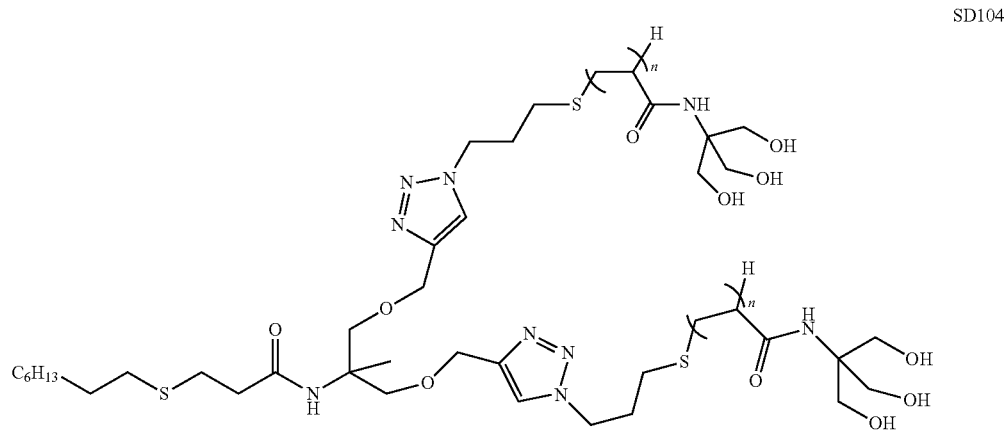

Structure of the dentriTAC molecules used for characterization.

10.1. Emulsion Preparation

The dentriTAC can encapsulate droplets of liquid perfluorocarbon (perfluoropentane, perfluorohexane, and perfluooctyl bromide (PFOB) have been tested so far) in an aqueous solution. The size and polydispersity of the droplet suspension strongly depend on the technique used to prepare the emulsion. We could produce emulsion using a vortex, a sonicator, or a microfluidizer. Only the two last approaches allow the formation of droplets where the majority of droplet is of nanometric size. In all preparation, an aqueous solution of surfactant is prepared so that the surfactant concentration is higher that the surfactant CMC and that the surfactant quantity is large enough to coat the whole droplet surface of every droplet (adjusted knowing the surfactant surface area, the mean droplet diameter which is aimed to, and the quantity of perfluorocarbon to be encapsulated).

Preparation Using an Ultrasonic Homogenizer.

About 10-50 mM of surfactant (either F-TAC or dentri-TAC) was first solubilized in 2 ml a saline solution (water+9‰ NaCl). A volume of 0.6 ml of perfluorocarbon liquid was added to the surfactant solution so that the molar ratio, $N_r$, of surfactant molecules to perfluorocarbon molecules was known and adjusted. Since the two liquids are immiscible, a two-phase solution was obtained, where the micelle aqueous solution was on the top and the perfluorocarbon liquid at the bottom due to its higher density. The two-phases solution was prepared in a 15 ml centrifuge plastic tube that was placed in iced water. The tip end of an ultrasound cell disruptor (Branson Digital Sonifier, model 450) was placed inside the solution at the interface between the micellar and perfluorocarbon liquids. Ultrasounds were applied twice during 30 s using 0.5 s cycles at 20 kHz frequency with a waiting time of 10 mn between the two insonifications.

Preparation Using a High-Pressure Microfluidizer

Surfactant (either F-TAC or dentriTAC) is solubilized into 4 ml of a saline solution (water+9‰ NaCl). 0.6 ml of PFC is then added to the aqueous solution. As the two liquids are immiscible, a two phases solution is obtained. A coarse pre-emulsion need to be prepared. It can be done either by vortexing if the surfactant is hydrophobic enough or by ultrasonic homogenization for more hydrophilic surfactants. Once the pre-emulsion is done and most bubbles or foam has disappeared, the coarse emulsion is going through a microfluidizer (LV1 model from Microfluidics) at a pressure of 20 000 psi. This operation is repeated five times. During the operation, the chamber and exit outlet are immerged in a water bath filled with iced water.

10.2. Emulsion Characterization

After preparation, the size distribution and mean diameter were measured at room temperature and monitored over time by Dynamic Light Scattering (DLS)[1] and Scanning Ion Occlusion Spectroscopy (SIOS)[2]. For DLS, measurements were performed using the ALV-Correlator Goniometer System (ALV-CGS) from ALV Company. This device is equipped with a 22 mW He—Ne laser ($\lambda$=633 nm) and a goniometer with an angular range from 17 to 152°. Samples were measured for angles varying from 60 to 120° with a running time of 60 s. Droplet volume fraction, $\Phi$, was in the range of $(0.1-0.2)\times 10^{-2}$ (i.e. 0.1-0.2%) to avoid multiple scattering effects and diameters were estimated with a precision of 0.5 nm. For SIOS, measurements were performed using the qNano device from Izon Company (New-Zealand) which principle is based on the Coulter effect. An elastomeric and resizable nanopore (NP) was used that covered a size range of either 70-200 nm (NP100), 100-400 nm (NP200), 200-800 nm (NP400), or 400-1600 nm (NP800). These ranges can be shifted by stretching the nanopore, in our case the applied stretching values were 45-48 mm. Voltage was set between 0.2 and 0.56 mV to keep the current baseline equals to approximatively 120 nA. For each nanopore a calibration was made using calibrated plain polystyrene particles. Each sample was measured at two pressures: 3 and 5 cm of $H_2O$, applied by a vapor pressure module. A minimum of 500 counting events were collected for each sample and analyzed using Izon Control Suite 2.1 software. The analysis extracts the droplet size distribution, which in turn provides the droplet mean diameter and the polydispersity index. An error of less than 3% was obtained for the mean diameter and of 5-10% for the mode diameter.

[1]Using a device from ALV.
[2]Using the qNano device from IZON Corp.

The two techniques gave similar mean diameter for identical samples. The size distribution of the qNano is more realistic as the technique literally counts the number or particules whereas the DLS provides an estimation based on multiple exponential fit. The size distributions were always right skewed (whatever the technique used to prepare the emulsion). The mean diameter and size distribution were monitored over a several weeks. In FIG. 8, it can be observed that the nanodroplets exist over several weeks. During this period the size continously increases, most probably due to Ostwalds ripening. Meanwhile, the polydispersity remains constant. FIG. 3 shows the nanodroplets size distribution, measured by qNano, at the day of emulsion preparation. It can be observed that the sample exhibits low polydispersity, with a mean diameter of droplets equal to 134.9 nm for the smallest droplets.

Ultrasound Imaging

The ultrasonic signal backscattered by the droplets suspension when an ultrasound wave was propagating into the emulsion has been measured. To do so a dedicated setup builtd in our laboratory was used. In such measurements, sample solutions were placed in a hollow cylindrical stainless steel chamber (30 mm in diameter and 3 mm in depth) maintained at 25° C. by a water circulation bath. The chamber was sealed with a cellophane membrane outstretched on a transparent tube. An ultrasonic focused transducer (model PI 50-2, Panametrics Inc., USA) was immersed into the water-filled tube. Its focal spot was positioned into the sample solution using a micro-control translation stage (VT-80, PI miCos, Eschbach, Germany). An optimized distance of 1.25 mm between the membrane and the center of the focal spot was used to minimize the influence of both sample solution attenuation and membrane vibrations on backscattered signals. The transducer was a 41 MHz PVDF transducer (34.25-47.75 MHz, −3 dB frequency bandwidth) with a 13 mm focal length and a 0.07×1 $mm^2$ (−3 dB) focal zone. Single short negative pulses (1 µJ energy) were generated in the sample at a 200 Hz repetition rate using a 200 MHz pulser-receiver (Panametrics Sofranel 5900 PR). Backscattered signals from the sample were received by the transducer/receiver set and digitized at a sampling rate of 2 GHz on a digital oscilloscope with a 8 bits vertical resolution (model WS424, Lecroy, USA). For each sample 100 signals were acquired and transferred to a personal computer for signal processing using MATLAB®. To select the zone of interest inside the sample, the signal processing consisted in the multiplication of each acquired signal by a Hann window of 2671 points (corresponding to the 1 mm length of the focal zone). The Power Spectrum density (PSD) of each resulting signal s(t) was calculated. Both operations were made at once using the modified periodogram method of MATLAB. This method is almost equivalent of calculating PSD as $PSD=|S(v)|^2$ where $S(v)$ is the Fast Fourier Transform of $s(t)$. The difference lies in the use of a normalization factor that compensates for energy losses due to windowing. Echogenicity of an emulsion was finally evaluated in comparison to control measurements in water by calculating the Signal-to-Noise Ratio $SNR(f)=10\times \log(PSD_S/PSD_W)$ where $PSD_S$ and $PSD_W$ are the mean Power Spectrum Densities over 100 PSD obtained in emulsion and in water, respectively. The calculation of an average PSD over many signals makes the SNR independent of particle configurations and, therefore, is representative of the so-called incoherent backscattered intensity. Finally, the mean value of $SNR(f)$ over the transducer $-3$ dB frequency bandwidth, $SNR_{mean}$, was extracted to characterize the echogenicity of an emulsion using a single quantity.

For emulsion prepared by ultrasound, a maximum $SNR_{mean}$ of 8 dB for emulsion made of dentriTAC and PFOB was obtained. This value is similar for emulsion exhibiting the same droplets size distribution but with another surfactant (i.e. F-TAC). It was shown that the main contributors to SNR are the microdroplets, present in small quantitites. When preparing emulsion with a microfluidizer, the micrometric population of droplet disappears and the tributyrin were tested. The oil is added to the emulsion during its preparation after obtention of a two-phases solution and before using the ultrasonic homogenizer or microfluidizer. It was observed that the oil forms a corona around the perfluorocarbon droplet, and the surfactant form a shell around this oily corona (see FIG. 4). For the drug, Z-Gly-Apathd and PPIX (see structures below) were used which are both hydrophobic and fluorescent molecules. The fluorescence spectra measured on emulsion prepared with drug demonstrate that the drug is indeed encapsulated into the droplets.

A fluor moiety is added to the drug which can be encapsulated inside the perfluorocarbon core or in the shell. Two molecules were tested:
1. a fluor-FTIC molecule with a fluorinated chain which has successfully been added to the emulsion by mixing the molecule with the surfactant aqueous solution. In this case, the FTIC is most probably located in the shell with the dentriTAC surfactant.
2. a fluor version of PPIX which has been solubilized into the perfluorocarbon liquid. In this case the fluoro-PPIX is most probably inside the doplet core.

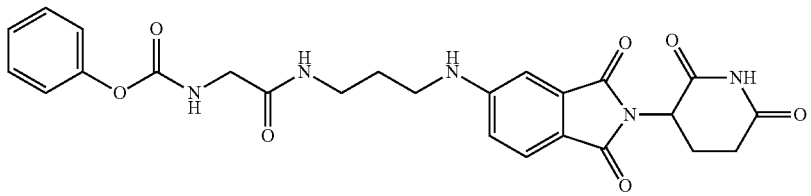

Structure of Z-Gly-Apathd

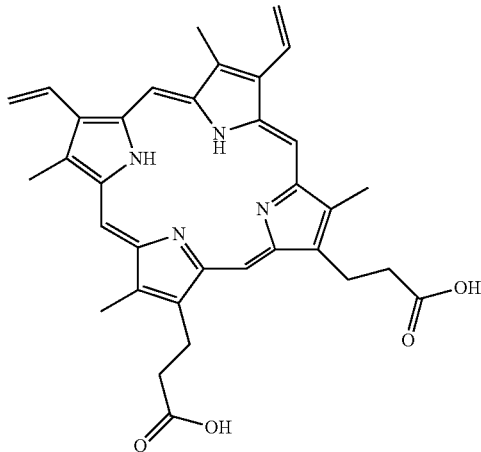

Structure of PPIX $SNR_{mean}$ is no more than 2 dB. Thus liquid perfluorocarbon droplets do not represent efficient ultrasound contrast agent. To make them detectable by echographic, it is then required to vaporize the liquid core.

Encapsulation

Drug encapsulation into the droplets can be achieved through two approaches (the approaches hold preparation using either an ultrasonic homogenizer or a high-pressure microfluidizer):

The drug is encapsulated into the droplets thanks to the addition of an oil. The oils triacetin, tripropionin, and Infra-Red Imaging The emulsion of the invention was used for infra-red fluorescence spectroscopy. To do so a fluorescent probe was encapsulated in a droplet made of PFOB and tripropionin or tributyrin. Either Red Nile or PPIX were used. The fluorescence spectra of the two probes are different according if they are solubilized in oil or in the oily part of the droplet. When encapsulated in emulsions, the excitation wavelength of PPIX is 400 nm and its maximum emission is located at 630 nm, while for Red Nile its excitation wavelength of Red Nile is 561 nm whereas its maximum emission is 623 nm.

$^{19}$F MRI

In order to assess if the emulsions made of dentriTAC and PFOB can be used as contrast agent for $^{19}$F MRI, $^{19}$F MR spectroscopy and 3D imaging were performed on emulsions filling the bulb of a plastic Pasteur pipette. A transmiter-receiver, double frequency $^{19}$F/$^{1}$H, saddle-type surface coil of 6 cm diameter was used with a 3T MR scanner (Siemens Trio, Erlangen, Germany). Fourier Transform was applied to the FID signal acquired from the whole sample (BW 15 kHz corresponding to 125 ppm, sampling size of 4096 points, flip angle ranges 20 to 90°, NEX=200, TR=205 ms, TE=0.35 ms). 3D imaging was performed with a nonselective pulse RF-spoiled GRE sequence, of main parameters: TR=10 ms, TE=3.25 ms, FA=45°, voxel size 1.1×1.1×3 or 3×3×3 mm$^3$, NSA=8, and acquisition time=2 min 44 s. $^{19}$F MRI data were acquired on emulsions made of PFOB droplets stabilized with dentriTAC surfactant, with a mean diameter of 400 nm and at droplet volume fractions ranging from $10^{-2}$ to $5\times10^{-2}$. All MRI spectra of emulsions exhibited five peaks (see FIG. 1, a) and b)) that are characteristic of pure PFOB since they were also observed for spectra measured on pure PFOB. They possess different longitudinal relaxation rates and, within the current precision of measurement, these relaxation rates are not modified between emulsion and pure PFOB. In addition, measurements were performed on triacetin-loaded emulsions and triacetin/Z-Gly-Apathd-loaded emulsions of similar droplet sizes and at $\Phi=5\times10^{-2}$. Presence of neither triacetin nor Z-Gly-Apathd in triacetin did not affect peaks location in the $^{19}$F MRI spectra.

11. Nanoemulsions Preparation by Ultrasonic Homogenizing

The nanoemulsion is prepared in a 50 ml centrifuge tube. Typically, 50 mg of DendriTAC are dissolved in 2 ml of deionized water (0.9% of NaCl), then 0.2 ml of PFOB is added and the mixture is cooled to 0° C. with an ice bath. The mixture is ultrasonicated with a sonicator (VibraCell™ 75043, 750 W, Bioblock Scientific, USA), using a 13 mm sonotrode (at the interface between the PFOB and the aqueous phase) at 60 or 40% amplitude, for 2 times 30 seconds with a waiting time between each insonification of 5 min.

11.1. Nanodroplets (ND) Size Evolution

Conditions: Sonotrode 13 mm, 2×30 seconds, amplitude 60%, Surfactant 50 mg, 2 ml of water (0.9% NaCl), PFOB 0.2 ml. Measurements are made before centrifugation.

TABLE 4

Hydrodynamic diameter of ND measured by dynamic light scattering (DLS)

| | Day | | | | | | | |
|---|---|---|---|---|---|---|---|---|
| | D0 | D7 | D14 | D 21 | D28 | D35 | D42 | D52 |
| F6diTAC10 | 169 nm | 222 nm | 247 nm | 266 nm | 279 nm | 279 nm | 296 nm | 302 nm |
| DiF6diTAC6 | 187 nm | 219 nm | 215 nm | 216 nm | 227 nm | 227 nm | 234 nm | 234 nm |
| F6TetraTAC6 | 191 nm | 239 nm | 261 nm | 275 nm | 301 nm | 301 nm | 334 nm | 360 nm |
| H12G0diTAC5 | 193 nm | 246 nm | 271 nm* | | *after 15 days | | | |

For all the fluorinated dendriTAC (DiF6diTAC6, F6diTAC10, F6TetraTAC6) the initial size is less than 200 nm, F6diTAC10 giving the lower size of 170 nm. However, the double tailed sample DiF6diTAC6 provided the more stable nanoemulsion with a stabilization at around 220 nm after 1 week for at least 28 days (FIG. 7).

It is noteworthy that nanoemulsions prepared with the hydrocarbon DendriTAC H12G0diTAC5 seem to grow more quickly over time. However, this hydrocarbon DendriTAC appeared to be interesting for drug encapsulation when a hydrocarbon oil is added to the perfluorocarbon core of nanodroplets. Indeed, encapsulation of Z-Gly-Apathd (structure described above) using the microfluidizer as previously described for fluorinated DendriTAC (surfactant=H12G0diTAC5; oil=tributyrine; perfluorocarbon core=PFOB; drug=Z-Gly-Apathd) gave nanoemulsions exhibiting an initial size of 156.7+/−3.2 nm which is a promising result.

11.2. Nanoemulsions Storage

11.2.1. Freezing

Emulsification conditions (Solution 1): 50 mg of F6diTAC6, 2 ml of water (0.9% NaCl), 0.2 ml PFOB, amplitude 60%, 2×30 seconds, sonotrode 13 mm.

TABLE 5

Influence of freezing on NE size evolution over time

| | Day 0 | Day 8 |
|---|---|---|
| Solution 1 (no freezing) | 224 nm | 251 nm |
| Solution 2 | 222 nm | nd |
| Solution 3 | 222 nm | nd |

Solution 1: stored in the fridge.

Solution 2: 200 µl of solution 1 is frozen by putting the sample in a freezer at −20° C. and kept there for 8 days and then defrost and stored in the fridge. The ND size is then measured once a week.

Solution 3: 200 µl of solution 1 is frozen by putting the sample in liquid nitrogen then put in the freezer at −20° C. for 8 days, then defrost and stored in the fridge. The ND size is then measured once a week.

Regardless the applied freezing method (liquid nitrogen or freezer), the ND size is in the same range before and after the freezing process. Freezing is thus seen as an useful method for NE samples storage.

11.2.2. Freeze Drying

Emulsification Conditions:

Sonotrode 13 mm, 2×30 seconds, amplitude 60%, 50 mg of F6diTAC10, 2 ml of water (0.9% NaCl), PFOB 0.2 ml, centrifugation at 900 g for 1 min. Following experiments are performed on the supernatant called NE1.

Freeze Drying (FD):

3 solutions of 300 μl were separately freeze dried for variable times (1, 2 or 3 hours). For each recovered sample, consecutive addition of water (same volume as removed) provided a new nanoemulsion called NE2 (FIG. 11).

Analysis of NE2:

The remaining amount of PFOB was assessed by $^{19}F$ NMR as followed: 10 μl of NE2 were supplemented with 300 μl of a saline solution (0.9% NaCl) and put in a NMR tube, along with a coaxial tube containing sodium trifluoroacetate in D2O as an external reference. The ratio of the integration for the external standard (ICF3 of TFA) over the integration of the NE sample (ICF3 of PFOB after 1 h, 2 h or 3 h of freeze drying) was measured and compared to that obtained with the starting solution NE1.

TABLE 6

Freeze drying time influence on size, aspect and PFOB concentration.

|  | NE1 | NE2 + 1 hour of FD | NE2 + 2 hours of FD | NE2 + 3 hours of FD |
|---|---|---|---|---|
| ND Size (nm) | 224 | 225 | 229 | 217 |
| Appearance after FD | — | milky solution | gel | white powder |
| Remaining PFOB in % | 100% | 77% | 57% | 51% |

Thus, the size of the ND did not change after the freeze drying process. In consequence, freeze drying enables an ease of use of dendriTAC nanoemulsions over time.

It is noteworthy that, as expected, the concentration of nanodroplets decreased. This is confirmed by the PFOB concentration in one hand and by the DLS count rate on the other hand (Data not shown). But this can be remedied by using less water when suspending the ND after freeze-drying, in order to retrieve the ND concentration before freeze-drying.

12. Preparation of Nanoemulsions Including Amphiphilic PPIX Derivatives within the Shell General Procedure During the emulsion preparation, amphiphilic PPIX derivatives were first added along with the fluorinated DendriTAC surfactant to the solvent (9‰ NaCl in pure water). At this point, micelles made of DendriTAC surfactant and amphiphilic PPIX are most probably obtained. Then, PFOB was added to the solution and the whole sample was emulsified using a high-pressure microfluidizer following the regular protocol described above.

In particular, the amphiphilic PPIX 45f (SD430) was used with the DentriTAC F6G0diPEG550 (SD370), and PFOB was used as liquid perfluorocarbon.

Fluorescence Measurements

Fluorescence measurements were conducted at an excitation wavelength of 200 nm as shown in FIG. 9. The difference in fluorescence spectra indicates that amphiphilic PPIX SD430 thus participates in the formation of PFOB droplets, by being most likely on the shell along with the DentriTAC.

Size Measurements

Emulsions with different [DendriTAC SD370]/[Amphiphilic PPIX SD430] ratios were produced. For each sample, the size of droplets was measured by qNano at the day of preparation and compared to that obtained with F-TACs, a known family of surfactant. With F-TAC SD346 (see structure below), it was observed that the droplet size decreases from 256 to 215 nm when the [F-TAC]/[Amphiphilic PPIX] ratio is enhanced from 400 to 40,000 (FIG. 10). It is noteworthy that an identical shift of the ratio [DendriTAC]/[Amphiphilic PPIX] allows to obtain much smaller droplets (130 nm) instead of 215 nm with F-TAC SD346 which is another attractive property of DendriTAC surfactants.

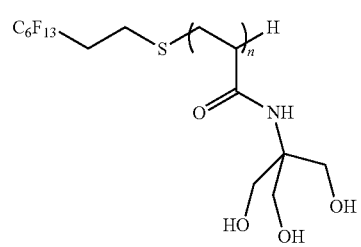

SD346: n = 6

The invention claimed is:

1. An amphiphilic dendrimer of generation n comprising:
an hydrophobic central core of valence 2 or 3;
generation chains attached to the central core and branching around the core; and
an hydrophilic terminal group at the end of each generation chain;
wherein,
n is an integer from 0 to 12;
the hydrophilic terminal group comprises:
  a cyclodextrin residue,
  a polyethylene glycol (PEG) residue,
  a peptide residue,
  a tris(hydroxymethyl)aminoethane (Tris), or
  a 2-amino-2-methylpropane-1,3-diol;
the central core being a group of formula (Ia) or (Ib):

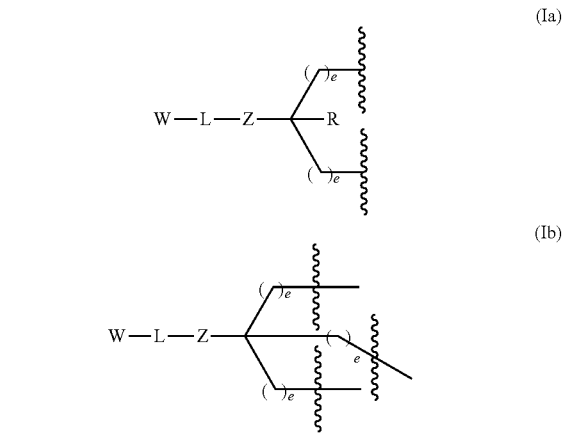

wherein:
W is $R_F$ or a group selected from the group consisting of $W_0$, $W_1$, $W_2$ and $W_3$:

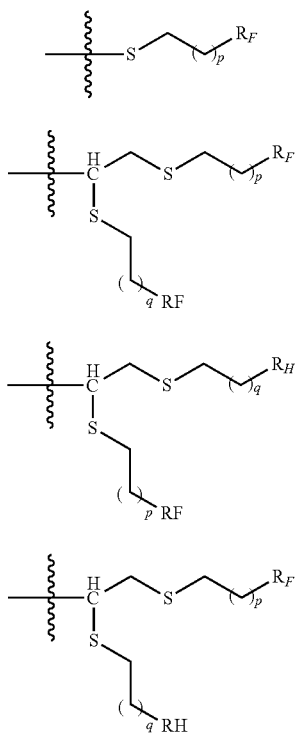

$W_0$ $W_1$ $W_2$ $W_3$ $R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more —O—, —S—,
Z is C(=O)NH or NHC(=O),
R is a $C_1$-$C_6$ alkyl group, and
e is at each occurrence independently 0, 1, 2, 3 or 4.

2. The dendrimer of claim 1, wherein WL is a group selected from the group consisting of:

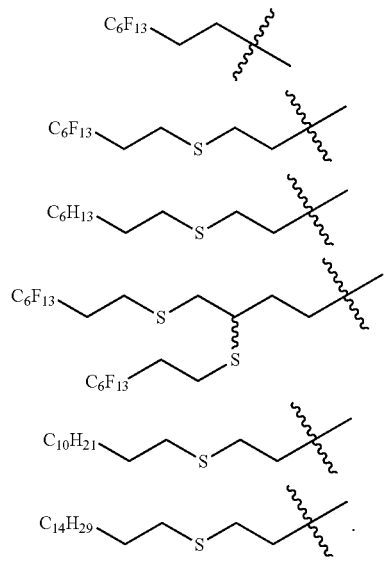

3. The dendrimer of claim 1, wherein each generation chain (n) branches via a group (a) or a group (b) as defined in claim 1 as follows:

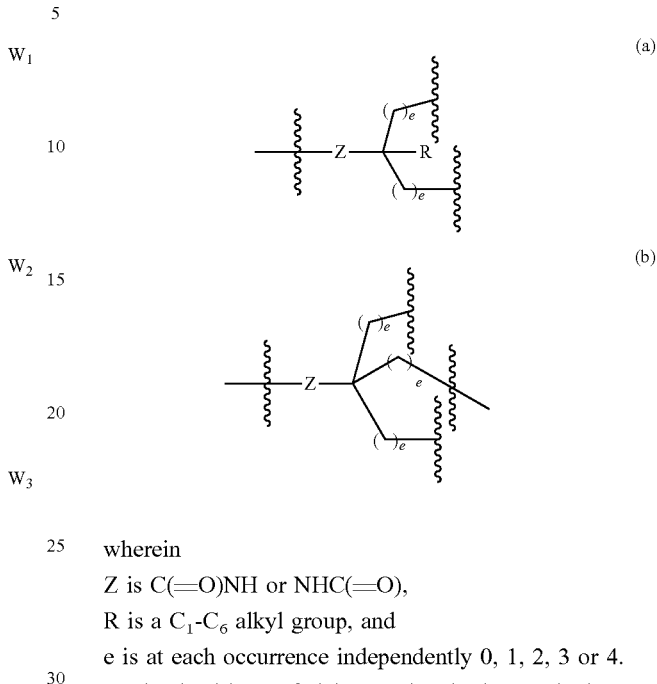

wherein
Z is C(=O)NH or NHC(=O),
R is a $C_1$-$C_6$ alkyl group, and
e is at each occurrence independently 0, 1, 2, 3 or 4.

4. The dendrimer of claim 1, wherein the terminal group comprises the following hydrophilic moieties:

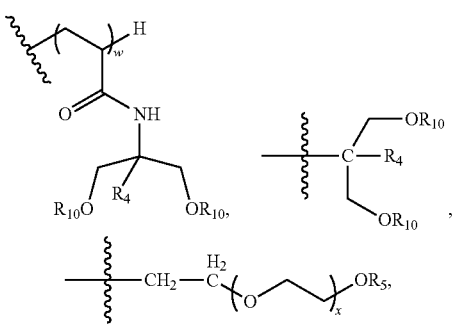

wherein,
$R_4$ is H, $C_1$-$C_6$ alkyl, or $CH_2OR_{10}$;
$R_5$ is H, or $C_1$-$C_6$ alkyl;
$R_{10}$ is H;
w is an integer from 1 to 20; and
x is an integer from 1 to 30.

5. The dendrimer of claim 1, having the following formula:

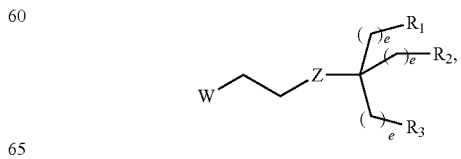

wherein:

W is $R_F$ or a group selected from the group consisting of:

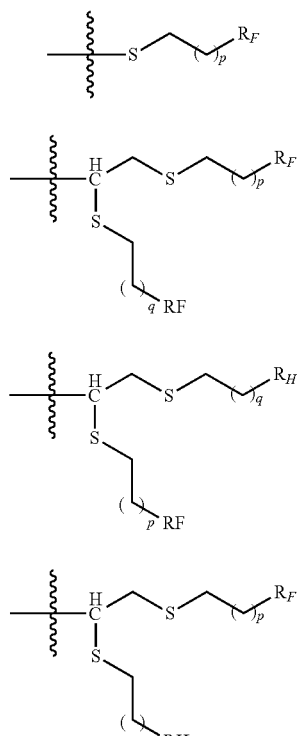

$R_F$ being a $C_4$-$C_{10}$ perfluoroalkyl or a $C_1$-$C_{24}$ alkyl group and $R_H$ being a $C_1$-$C_{24}$ alkyl group, p is 0, 1, 2, 3 or 4;

q is 0, 1, 2, 3 or 4;

Z is (CO)NH or NH(CO);

$R_1$, $R_2$, $R_3$ are H, or a group selected from the group consisting of (c) and (d):

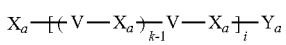

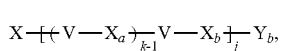

provided that:

$R_1$, $R_2$, $R_3$ are the same and either group (c) or (d) or one of $R_1$, $R_2$, $R_3$ is H, the two others being the same and either group (c) or (d);

X is $X_a$ when j is 1 and $X_b$ when j is 0;

$X_a$ is at each occurrence independently —OC(=O)CH$_2$—NH—, —OC(=O)CH$_2$—O—CH$_2$—, —O(CH$_2$)$_r$C(=O)—NH—, —O(CH$_2$)$_r$C(=O)—O—CH$_2$, OC(=O)NH—, —C(=O)—, —NH—, or —OCH$_2$—;

$Y_a$ is independently selected from the group consisting of:

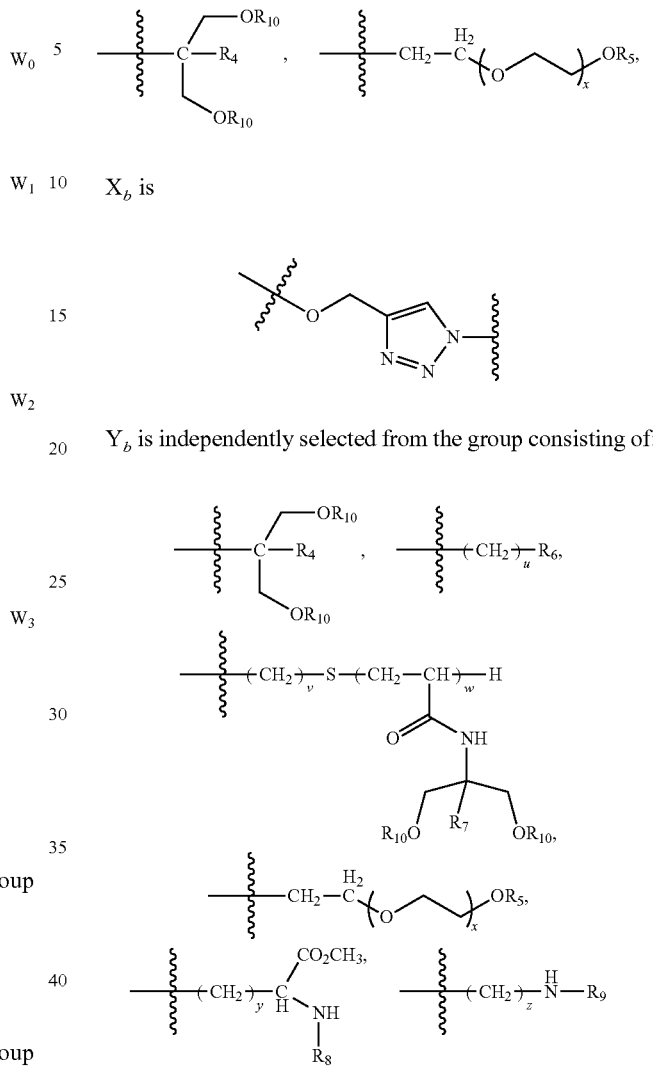

V is

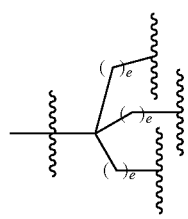

$R_4$, $R_7$ are each independently H, $C_1$-$C_6$ alkyl or CH$_2$OR$_{10}$;

$R_5$ is H or $C_1$-$C_6$ alkyl;

$R_6$ is a cyclodextrin residue;

$R_8$, $R_9$ are each independently a peptide residue;

$R_{10}$ is H;

i is 0 or 1;

j is 0 or 1;

e is 0, 1, 2, 3 or 4;

k is an integer from 1 to 12, preferably 1, 2, 3, 4, or 5;

r is an integer from 1 to 10;
u is 0, 1, 2, 3 or 4;
v is 1, 2, or 3;
w is an integer from 1 to 20, preferably from 1 to 10;
x is an integer from 1 to 30, preferably from 5 to 15;
y, z are each independently an integer from 1 to 6.
6. A dendrimer which is selected from the group consisting of:
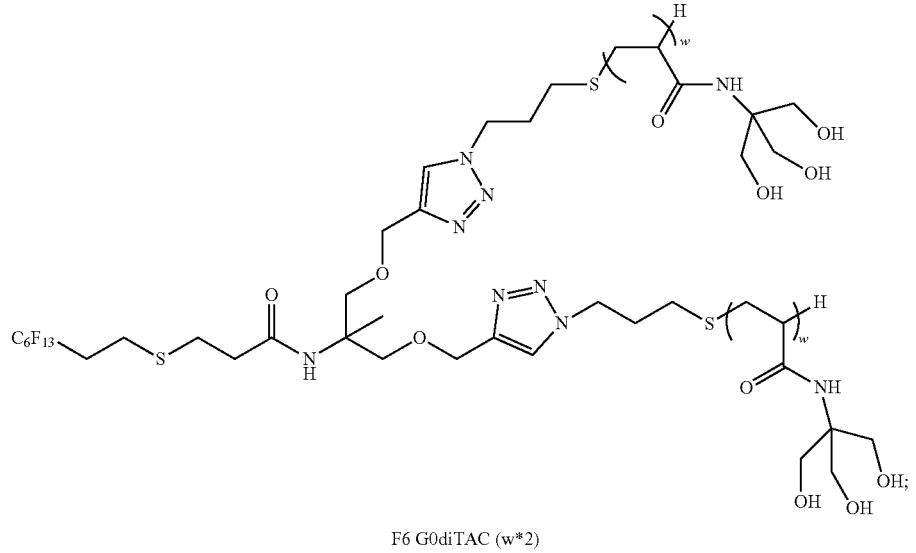
F6 G0diTAC (w*2)
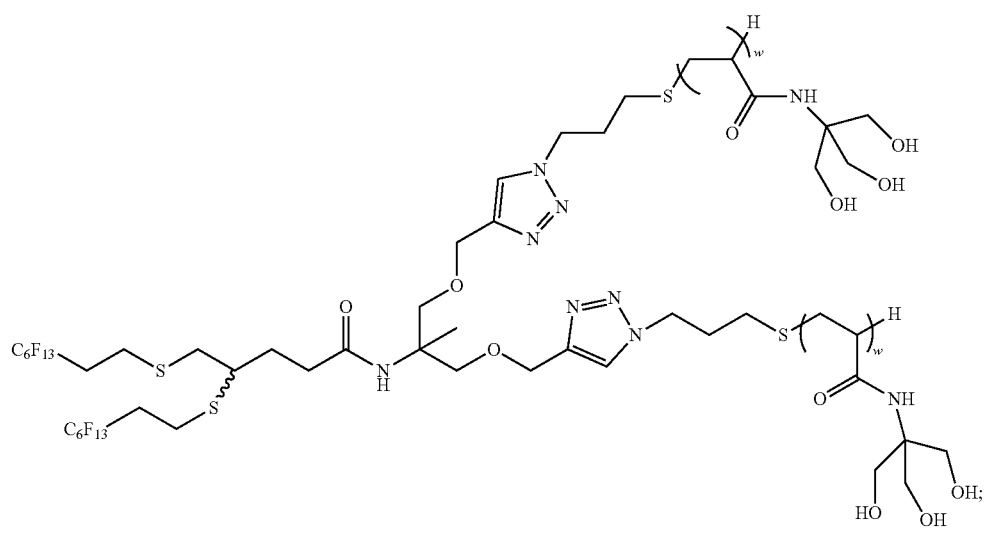
DiF6 G0diTAC (w*2)
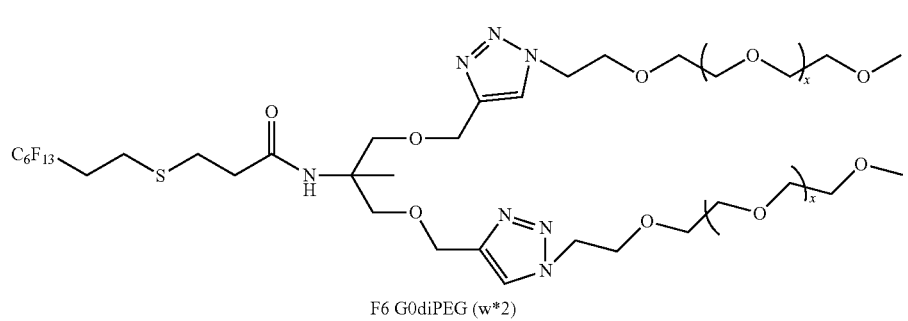
F6 G0diPEG (w*2)

-continued
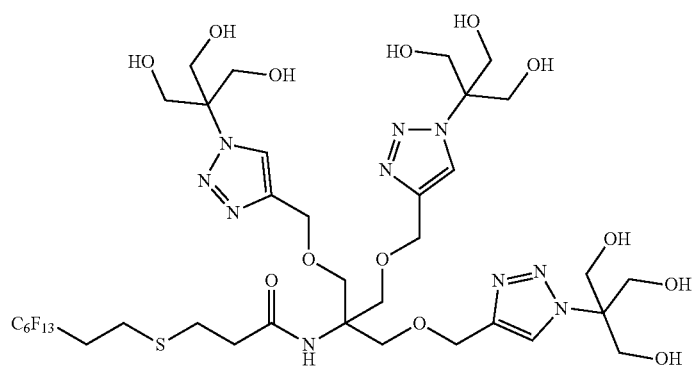
F6 G0triTRIS
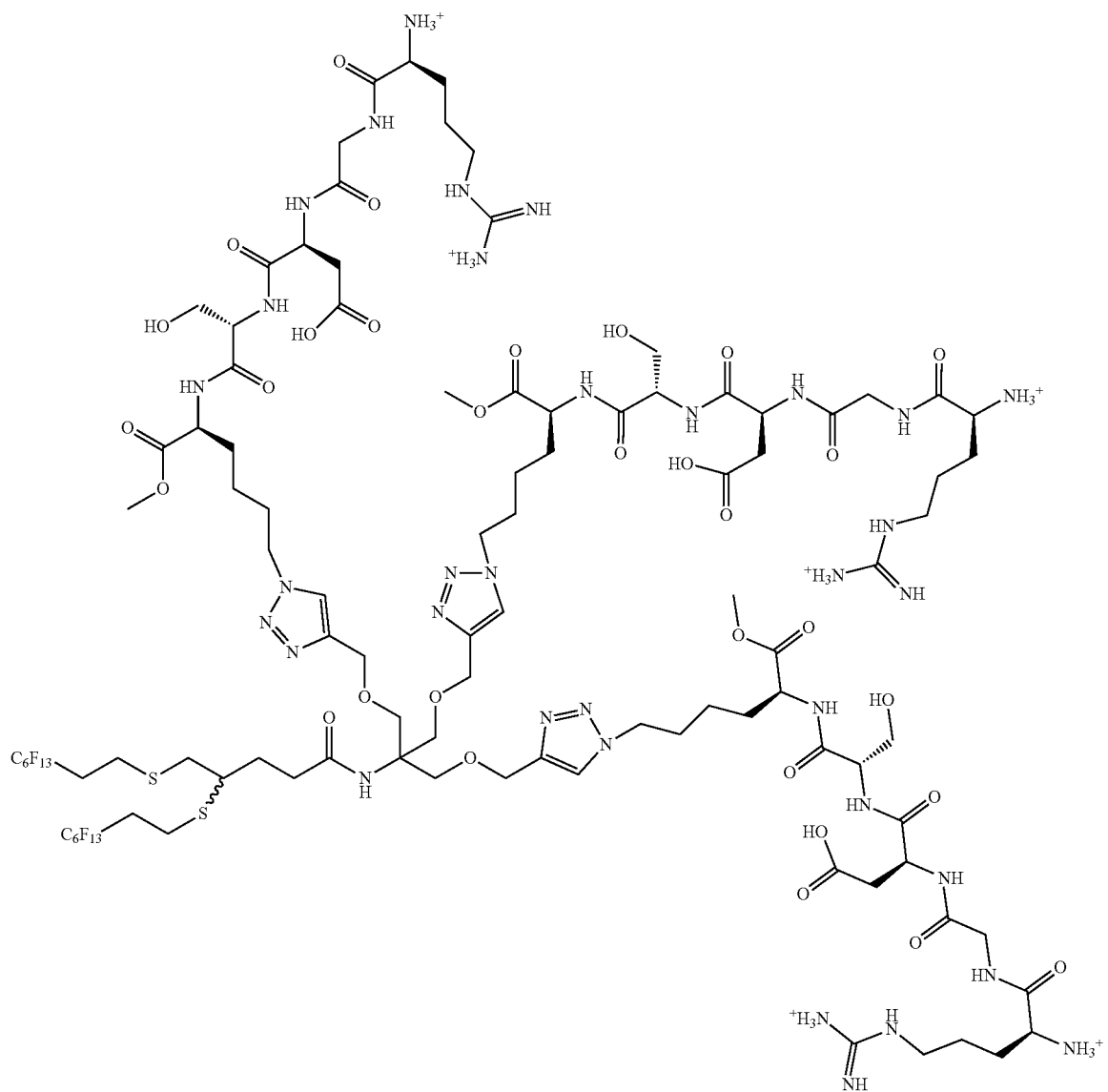
DiF6 G0triSDGR

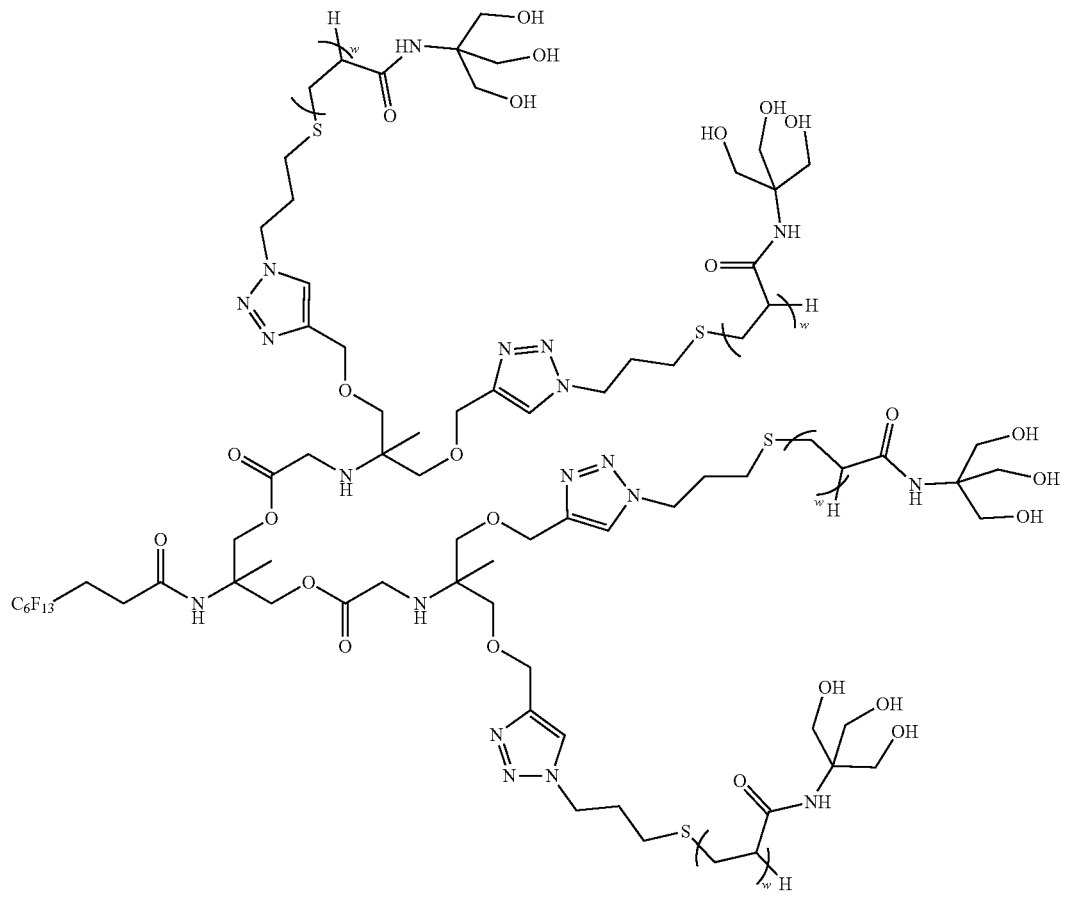
F6G1(ester)tetraTAC

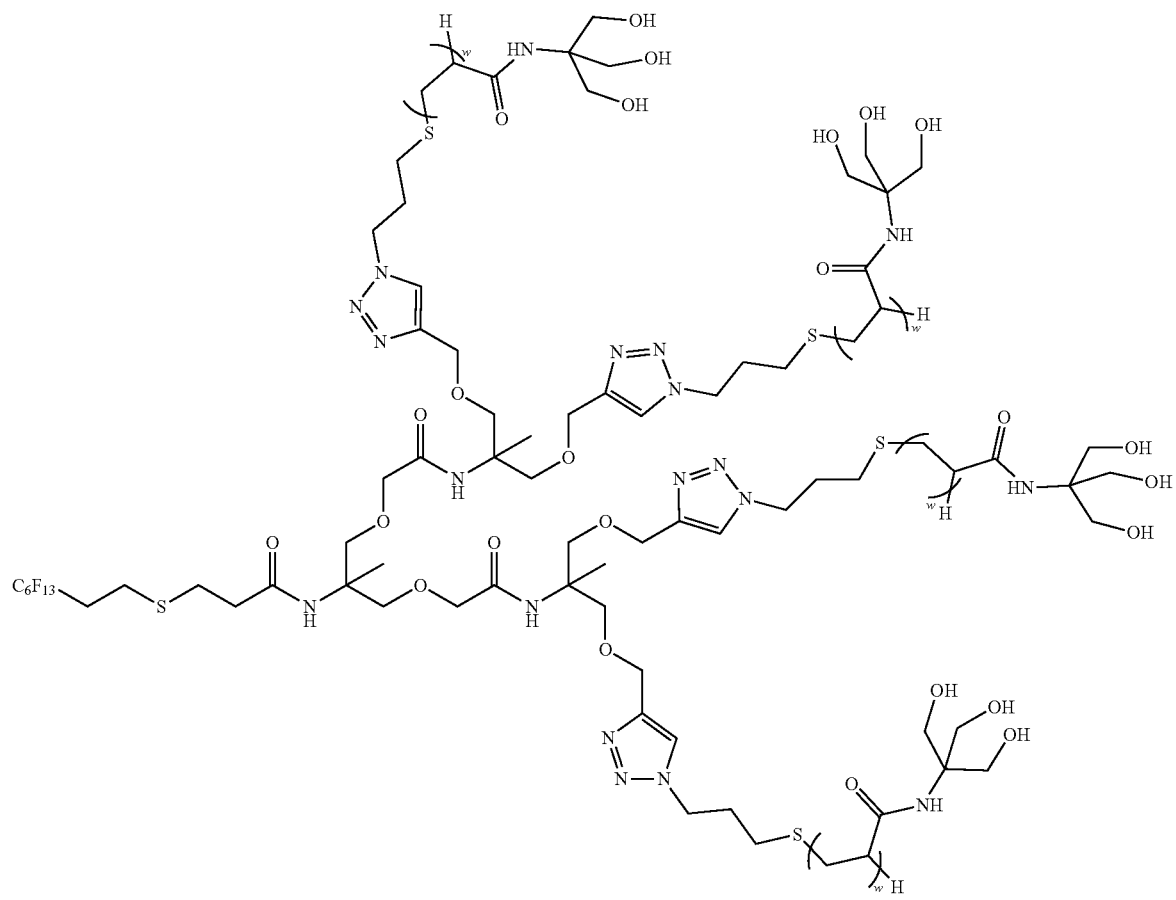
F6G1(amide)tetraTAC

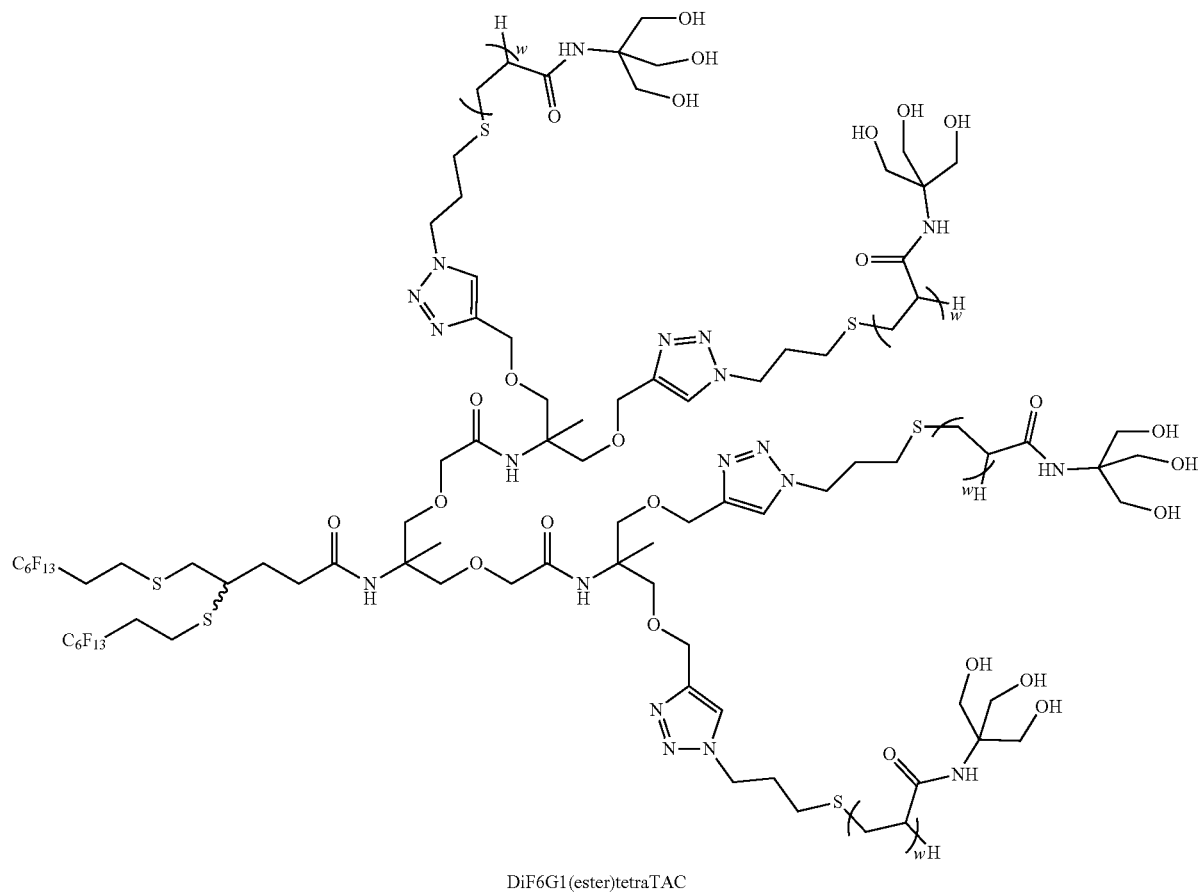
DiF6G1(ester)tetraTAC

-continued
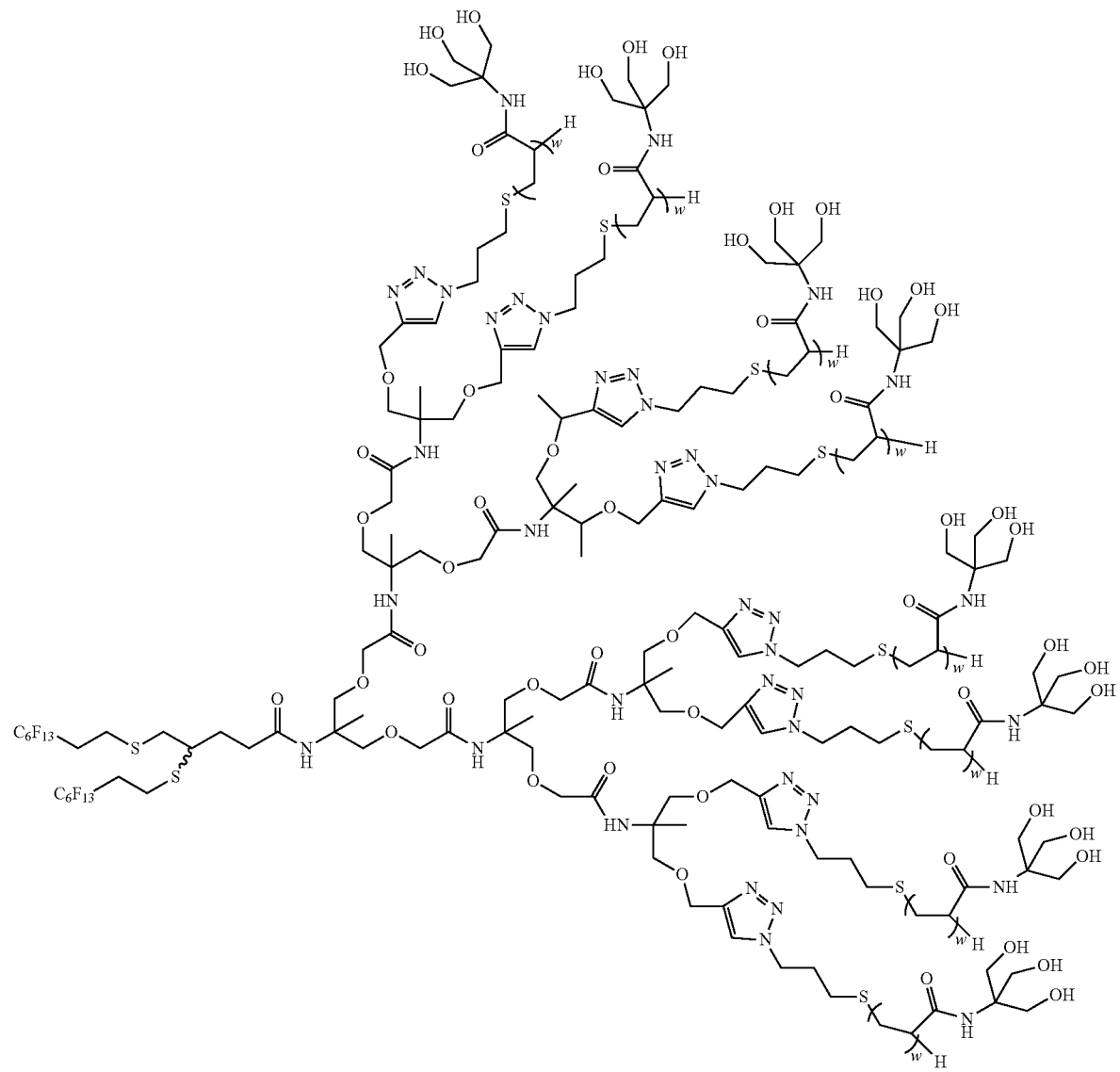
DiF6 G2(amide)octaTAC

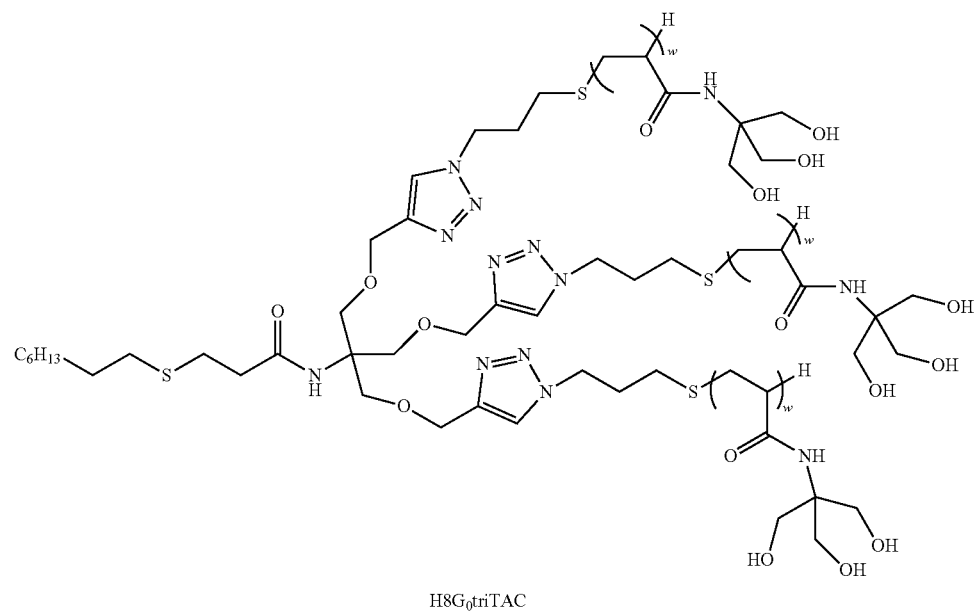
H8G$_0$triTAC
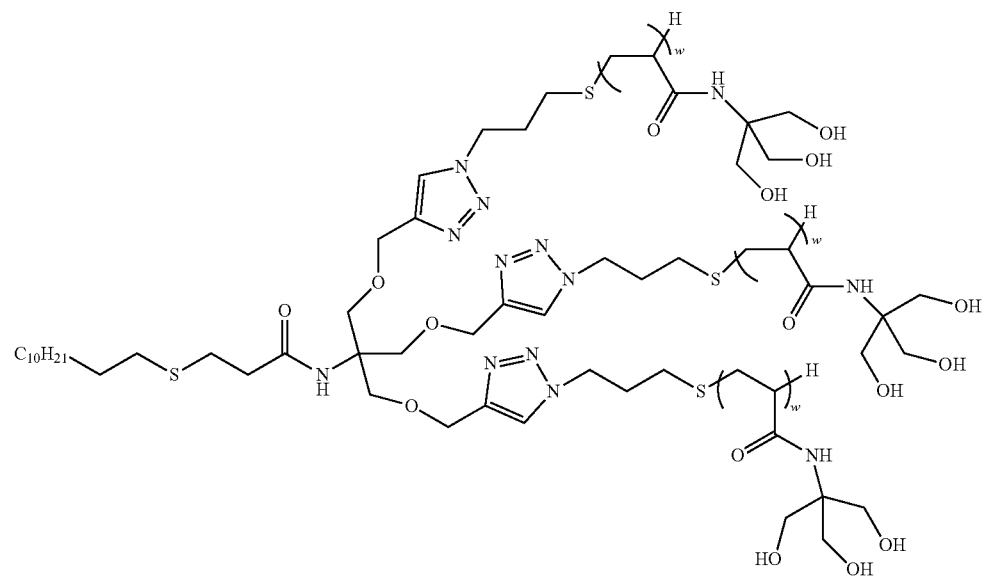
H12G$_0$triTAC

-continued
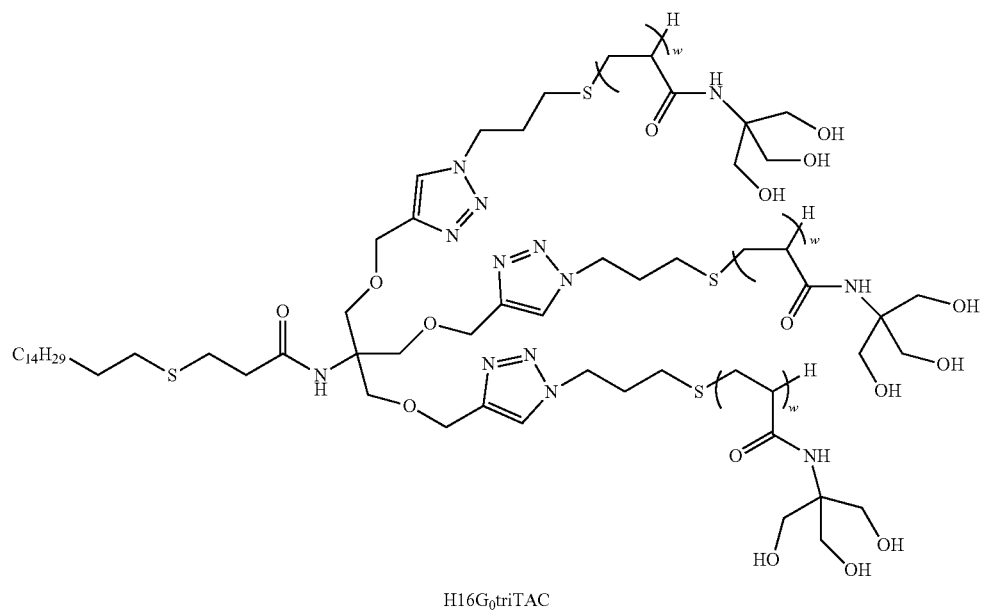
H16G₀triTAC
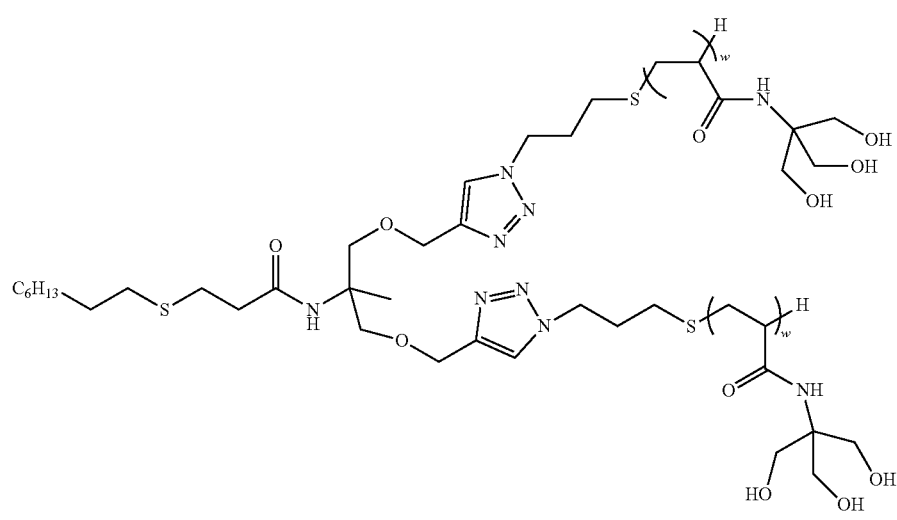
H8G₀diTAC
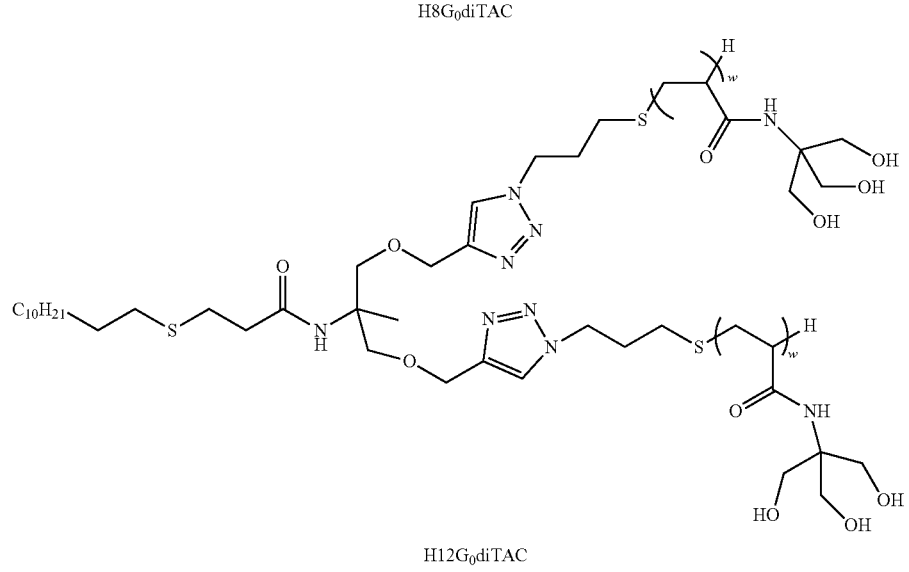
H12G₀diTAC

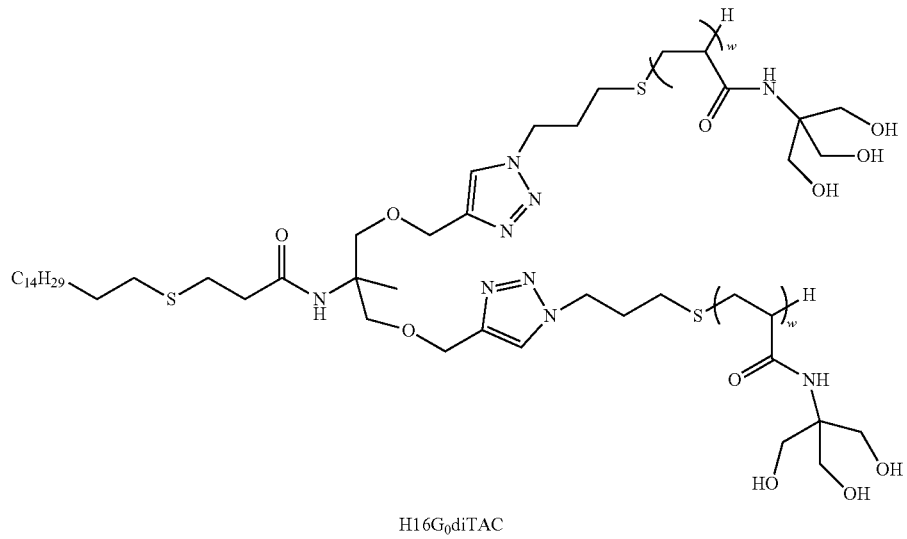

H16G₀diTAC wherein x and w are as defined in claim 1.

7. A nanoemulsion comprising:
as a discontinuous phase, a perfluorocarbon compound,
as a continuous phase, an aqueous phase,
an amphiphilic dendrimer as defined in claim 1 as a surfactant,
optionally a biocompatible hydrocarbon oil.

8. The nanoemulsion of claim 7, wherein the discontinuous phase is loaded with solubilized oxygen.

9. The nanoemulsion of claim 7, wherein the discontinuous phase further comprises a sonosensitive and/or photosensitive agent and/or an active ingredient.

10. The nanoemulsion of claim 7, wherein the discontinuous phase further comprises a sonosensitive and/or photosensitive agent and/or an active ingredient, said nanoemulsion further comprising a biocompatible hydrocarbon oil.

11. The nanoemulsion of claim 10, wherein the sonosensitive and/or photosensitive agent is selected from protoporphyrin IX (PpIX), hematoporphyrin (Hp), photofrin II, hematoporphyrin monomethyl ether (HMME), ATX-70, chlorin e6, chlorin family (dihydroporphyrin), bacteriochlorin family (tetrahydroporphyrin), ATX-S10, sinoporphyrin sodium (called DVDMS) or a chlorophyll-derived porphyrin analogue, and PPIX derivatives of the following formula:

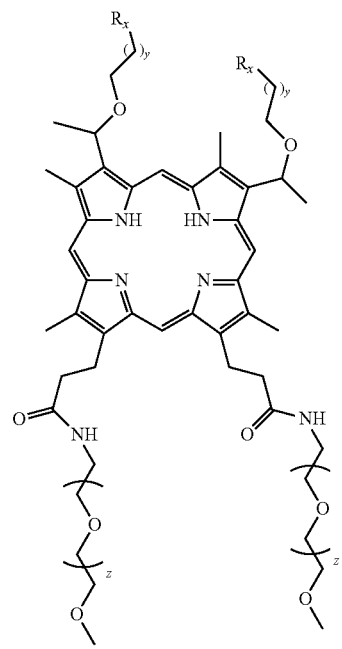

wherein
$R_x$ is a $C_1$-$C_{10}$ perfluoroalkyl or a $C_1$-$C_{24}$ alkyl group,
y is 0, 1, 2, 3 or 4,
z is 1 to 200.

12. A method of diagnosis or treatment comprising a step of administration to a patient in need thereof an effective amount of the nanoemulsion of claim 7.

13. The method of claim 12, in tumor imaging.

14. The method of claim 13, wherein the tumor imaging is selected from contrast echography, near-infrared fluorescence, photoacoustic imaging and Magnetic Resonance Imaging (MRI), in particular from ultrasound echography, and fluorine Nuclear Magnetic Resonance.

15. The method of claim 12, in the treatment of cancer.

16. The method of claim 15, in sonodynamic or photodynamic therapy.

17. The method of claim 12, wherein the terminal group of the dendrimer comprises or is attached to a targeting ligand.

18. The method of claim 17, wherein the targeting ligand is a RGD peptide.

19. A nanoparticle comprising:
a core containing a perfluorocarbon compound, said core being optionally surrounded by a layer of biocompatible hydrocarbon oil,
a shell composed of amphiphilic dendrimers according to claim 1.

20. A process of preparation of a nanoemulsion comprising:
as a discontinuous phase, a perfluorocarbon compound,
as a continuous phase, an aqueous phase,
an amphiphilic dendrimer according to claim 1,
optionally a biocompatible hydrocarbon oil,
said process comprising:
a step of emulsifying a system comprising:
an aqueous phase comprising an amphiphilic dendrimer according to claim 1,
a perfluorocarbon compound,
optionally a biocompatible hydrocarbon oil,
to obtain said nanoemulsion.

21. Process according to claim 20 further comprising a step of storage of the obtained nanoemulsion.

22. Process according to claim 21 further comprising a step of storage of the obtained nanoemulsion by freezing said nanoemulsion to obtain a frozen nanoemulsion.

23. Process according to claim 22 further comprising a step of obtaining a ready-to-use nanoemulsion from the frozen nanoemulsion by defrosting the frozen nanoemulsion.

24. Process according to claim 21 further comprising a step of storage of the obtained nanoemulsion by freeze-drying said nanoemulsion to obtain a lyophilized nanoemulsion.

25. Process according to claim 24 further comprising a step of obtaining a ready-to-use nanoemulsion from the lyophilized nanoemulsion by resuspending the lyophilized nanoemulsion in water.

* * * * *